(12) United States Patent
Jung et al.

(10) Patent No.: US 10,745,396 B2
(45) Date of Patent: *Aug. 18, 2020

(54) PESTICIDALLY ACTIVE POLYCYCLIC DERIVATIVES WITH SULFUR CONTAINING SUBSTITUENTS

(71) Applicant: Syngenta Participations AG, Basel (CH)

(72) Inventors: Pierre Joseph Marcel Jung, Stein (CH); Andrew Edmunds, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/732,803

(22) PCT Filed: Jun. 27, 2016

(86) PCT No.: PCT/EP2016/064784
§ 371 (c)(1),
(2) Date: Dec. 29, 2017

(87) PCT Pub. No.: WO2017/001314
PCT Pub. Date: Jan. 5, 2017

(65) Prior Publication Data
US 2018/0312501 A1 Nov. 1, 2018

(30) Foreign Application Priority Data

Jul. 1, 2015 (EP) .................................... 15174760
Sep. 7, 2015 (EP) .................................... 15184065

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01)

(58) Field of Classification Search
CPC .................................................... C07D 471/04
See application file for complete search history.

(56) References Cited

U.S. PATENT DOCUMENTS 10,005,775 B2 * 6/2018 Jung .................... C07D 471/04
2015/0094329 A1 4/2015 Nokura

FOREIGN PATENT DOCUMENTS

EP 2857397 A1 4/2015

OTHER PUBLICATIONS

Extended European search report for 15174760.7, dated Aug. 19, 2015.
International Search Report and Written Opinion for PCT/EP2016/064784, dated Aug. 25, 2016.

* cited by examiner

*Primary Examiner* — Brian E McDowell
(74) *Attorney, Agent, or Firm* — Baker & Hostetler, LLP; Toni-Junell Herbert

(57) ABSTRACT

Polycyclic derivatives of formula (I), wherein the substituents are as defined in claim 1, and the agrochemically acceptable salts, stereoisomers, enantiomers, tautomers and N-oxides of those compounds, can be used as insecticides and can be prepared in a manner known per se.

8 Claims, No Drawings

PESTICIDALLY ACTIVE POLYCYCLIC DERIVATIVES WITH SULFUR CONTAINING SUBSTITUENTS

RELATED APPLICATION INFORMATION

This application is a 371 of International Application No. PCT/EP2016/064784, filed 27 Jun. 2016, which claims priority to EP 15174760.7, filed 1 Jul. 2015, and EP 15184065.9 filed 7 Sep. 2015, the contents of which are incorporated herein by reference herein.

The present invention relates to pesticidally active, in particular insecticidally active polycyclic derivatives containing sulfur substituents, to compositions comprising those compounds, and to their use for controlling animal pests, including arthropods and in particular insects or representatives of the order Acarina.

Heterocyclic compounds with sulfur containing substituents and pesticidal action are known and described, for example, in WO 2012/086848, WO 2013/018928, WO 2014/142292 and WO2015/000715. There have now been found novel pesticidally active polycyclic ring derivatives with sulphur containing phenyl and pyridyl substituents.

The present invention accordingly relates to compounds of formula I,

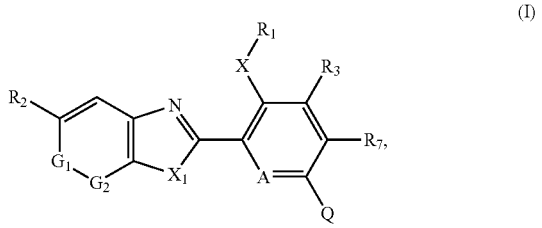

(I)

wherein
A is CH, N or the N-oxide;
$G_1$ is $NR_4$ and $G_2$ is $C(Y)$; or
$G_1$ is $C(Y)$ and $G_2$ is $NR_5$;
Y is O or S;
X is S, SO or $SO_2$;
$X_1$ is $NR_6$, wherein $R_6$ is hydrogen, $C_2$-$C_6$alkenyl, $C_2$-$C_6$alkynyl, $C_1$-$C_4$alkoxy-$C_1$-$C_4$alkyl, $C_3$-$C_6$cycloalkyl or $C_1$-$C_6$alkyl which can be mono- or polysubstituted by substituents selected from the group consisting of halogen and $C_1$-$C_4$alkylsulfinyl; or
$X_1$ is oxygen or sulfur;
Q is a five- to six-membered monocyclic ring system linked via a carbon atom to the ring which contains the group A, said ring system is aromatic, partially saturated or fully saturated and can contain 1 to 4 hetero atoms selected from the group consisting of nitrogen, oxygen and sulfur; with the proviso that each ring system cannot contain more than 2 oxygen atoms and more than 2 sulfur atoms; said five- to six-membered ring system can be mono- to polysubstituted by substituents independently selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; or Q is a five- to six-membered, aromatic, partially saturated or fully saturated ring system containing 1, 2 or 3 nitrogen atoms, said ring system is linked via a nitrogen atom to the ring which contains the group A, said ring system can be mono- or polysubstituted by substituents selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl;
and said ring system can additionally contain 1 or 2 heteroatoms selected from the group consisting of nitrogen, oxygen and sulfur, with the proviso that said ring system cannot contain more than one oxygen atom and more than one sulfur atom; or Q is $C_3$-$C_4$cycloalkyl or $C_3$-$C_4$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and $C_1$-$C_4$haloalkylcarbonyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy or phenyl wherein said phenyl can be mono- or polysubstituted by substituents selected from the group consisting of halogen, cyano, $C_1$-$C_4$alkyl, $C_1$-$C_4$haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy or phenyl wherein said phenyl can be mono- or polysubstituted by substituents selected from the group consisting of halogen, cyano, $C_1$-$C_4$alkyl, $C_1$-$C_4$haloalkyl; or Q is $C_1$-$C_4$alkyl mono- or polysubstituted by substituents selected from the group consisting of $C_3$-$C_6$cycloalkyl, phenyl, pyridine and pyrimidine, wherein said $C_3$-$C_6$cycloalkyl, phenyl, pyridine and pyrimidine can be mono- or polysubstituted by substituents selected from the group consisting of halogen, cyano, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy;

$R_1$ is $C_1$-$C_6$alkyl, $C_1$-$C_6$haloalkyl, $C_3$-$C_6$cycloalkyl or $C_3$-$C_6$cycloalkyl-$C_1$-$C_4$alkyl; or
$R_1$ is $C_3$-$C_6$cycloalkyl-$C_1$-$C_4$alkyl mono- or polysubstituted by substituents selected from the group consisting of halogen, cyano, $C_1$-$C_4$haloalkyl and $C_1$-$C_4$alkyl; or
$R_1$ is $C_2$-$C_6$alkenyl, $C_2$-$C_6$haloalkenyl, $C_2$-$C_6$alkynyl or $C_2$-$C_6$haloalkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_6$haloalkylsulfanyl, $C_1$-$C_6$haloalkylsulfinyl, $C_1$-$C_6$haloalkylsulfonyl, $C_1$-$C_6$haloalkoxy, or $C_1$-$C_6$haloalkylcarbonyl; or
$R_2$ is $C_3$-$C_6$cycloalkyl which can be mono- or polysubstituted by substituents selected from the group consisting of halogen, cyano, $C_1$-$C_4$haloalkyl and $C_1$-$C_4$alkyl;

$R_3$ is hydrogen or $C_1$-$C_2$alkyl;

$R_4$ and $R_5$ are, independently from each other, $C_1$-$C_6$alkyl, $C_1$-$C_6$haloalkyl, or are $C_3$-$C_6$cycloalkyl which can be mono- or polysubstituted by substituents selected from the group consisting of halogen, cyano, $C_1$-$C_4$haloalkyl and $C_1$-$C_4$alkyl; or $R_4$ and $R_5$ are, independently from each other, $C_3$-$C_6$cycloalkyl-$C_1$-$C_4$alkyl which can be mono- or polysubstituted by cyano, $C_1$-$C_4$alkyl, halogen or $C_1$-$C_2$haloalkyl; or $R_4$ and $R_5$ are, independently from each other, $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl; or $R_4$ and $R_5$ are, independently from each other, $C_1$-$C_4$alkyl substituted by $R_8$; or $R_4$ and $R_5$ are, independently from each other, $C_2$-$C_6$alkenyl substituted by $R_8$; or $R_4$ and $R_5$ are, independently from each other, $C_2$-$C_6$alkynyl substituted by $R_8$;

$R_7$ is hydrogen, halogen, $C_1$-$C_6$haloalkyl, $C_1$-$C_6$haloalkylsulfanyl, $C_1$-$C_6$haloalkylsulfonyl, $C_1$-$C_6$haloalkylsulfinyl, $C_3$-$C_6$cycloalkyl or $C_3$-$C_6$cycloalkyl mono or polysubstituted by halogen, cyano, $C_1$-$C_4$alkyl or $C_1$-$C_4$haloalkyl; and $R_8$ is cyano, $C_1$-$C_6$alkylsulfanyl, $C_1$-$C_4$alkylsulfonyl, $C_1$-$C_4$alkylsulfinyl, $C_1$-$C_4$haloalkylsulfanyl, $C_1$-$C_4$haloalkylsulfonyl, $C_1$-$C_6$haloalkylsulfinyl, $C_1$-$C_4$alkoxy, $C_1$-$C_4$alkoxy$C_1$-$C_4$alkoxy, $C_3$-$C_6$cycloalkyl or phenyl; said phenyl and said $C_3$-$C_6$cycloalkyl can be mono- or polysubstituted by substituents selected from the group consisting of halogen, $C_1$-$C_4$alkyl, cyano, $C_1$-$C_4$haloalkyl and $C_1$-$C_4$alkoxy; and agrochemically acceptable salts, stereoisomers, enantiomers, tautomers or N-oxide of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylcarbonyl is for example methylcarbonyl (which is $C_1$alkylcarbonyl), ethylcarbonyl, propylcarbonyl, isopropylcarbonyl, n-butylcarbonyl, tert-butylcarbonyl, n-pentylcarbonyl or hexylcarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

Cycloalkyl is, for example, cyclopropyl, cyclobutyl, cyclopentyl and cyclohexyl.

According to the present invention, in the definition of Q as a five- to six-membered monocyclic ring system linked via a carbon atom to the ring which contains the group A, said ring system is aromatic, partially saturated or fully saturated and can contain 1 to 4 hetero atoms selected from the group consisting of nitrogen, oxygen and sulfur; or as a five- to six-membered aromatic, partially saturated or fully saturated ring system containing 1, 2 or 3 nitrogen atoms, said ring system is linked via a nitrogen atom to the ring which contains the group A; the monocyclic groups Q are preferably selected, as appropriate (for example if the link with the nitrogen atom is chemically possible or not), from the group consisting of cyclohexyl, cyclopentyl, phenyl, pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; pyrrolidinyl, piperidinyl; pyrrolidinyl-2-one; piperidinyl-2-one; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-(1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)- and (furazan-3-yl)-.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

Preferably $R_4$ and $R_5$ are, independently from each other, $C_1$-$C_6$alkyl, $C_1$-$C_6$haloalkyl, or are $C_3$-$C_6$cycloalkyl which can be mono- or polysubstituted by substituents selected from the group consisting of halogen, cyano, $C_1$-$C_4$haloalkyl and $C_1$-$C_4$alkyl; or $R_4$ and $R_5$ are, independently from each other, $C_3$-$C_6$cycloalkyl-$C_1$-$C_4$alkyl which can be mono- or polysubstituted by cyano, halogen or $C_1$-$C_2$haloalkyl; or $R_4$ and $R_5$ are, independently from each other, $C_1$-$C_6$alkyl substituted by cyano or by phenyl which itself can be mono- or polysubstituted by substituents selected from the group consisting of halogen, cyano, $C_1$-$C_4$alkyl, $C_1$-$C_4$haloalkyl and $C_1$-$C_4$alkoxy; or $R_4$ and $R_5$ are, independently from each other, $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl.

In preferred compounds of formula I, Q is selected from the group consisting of J-0 to J-31

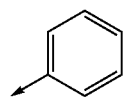
J-0

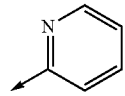
J-1

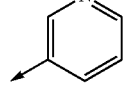
J-2

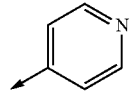
J-3

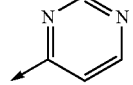
J-4

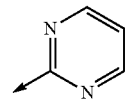
J-5

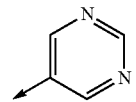
J-6

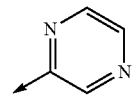
J-7

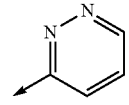
J-8

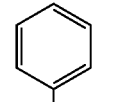
J-9

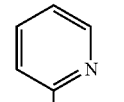
J-10

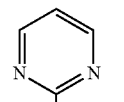
J-11

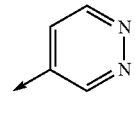
J-12

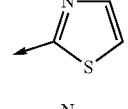
J-13

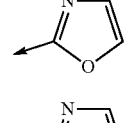
J-14

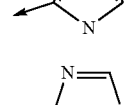
J-15

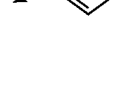
J-16

-continued

J-17 

J-18

J-19

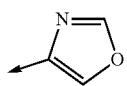 J-16...

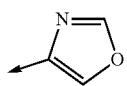
J-17

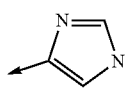
J-18

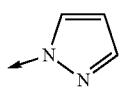
J-19

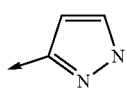
J-20

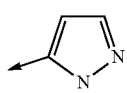
J-21

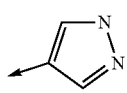
J-22

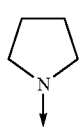
J-23

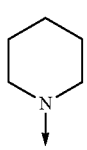
J-24

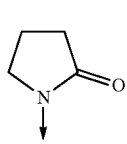
J-25

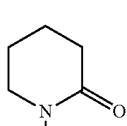
J-26

J-27

J-28

J-29

J-30

J-31

wherein each group J-0 to J-8 and J-12 to J-26 can be mono- di- or trisubstituted with Rx, wherein each Rx, independently from each other, is selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; wherein the group J-27 can be mono- di- or trisubstituted with Rx, wherein each Rx, independently from each other, is halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and $C_1$-$C_4$haloalkylcarbonyl; wherein the aromatic part of the group J-9 to J11 can be mono- di- or trisubstituted with Rx, wherein each Rx, independently from each other, is selected from the group consisting of halogen, cyano, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy.

A preferred group of compounds of formula I is represented by the compounds of formula I-1

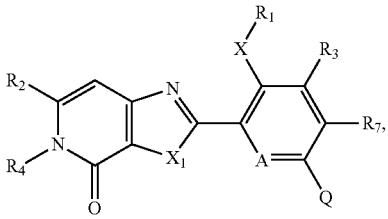

(I-1)

wherein $R_2$, A, X and Q are as defined under formula I above; $R_4$ is as defined under formula I above, preferably $C_1$-$C_4$alkyl; $R_1$ is methyl, ethyl, n-propyl, i-propyl or cyclopropylmethyl; $R_3$ is hydrogen, $R_7$ is hydrogen, halogen or $C_1$-$C_3$haloalkyl; $X_1$ is N-methyl, oxygen or sulfur; and agrochemically acceptable salts, stereoisomers, enantiomers, tautomers and N-oxides of the compounds of formula I-1.

In said preferred group of compounds of formula I-1, $R_2$ is preferably $C_1$-$C_4$haloalkyl, halogen, $C_1$-$C_4$haloalkylsulfanyl, $C_1$-$C_4$haloalkylsulfinyl or $C_1$-$C_4$haloalkylsulfonyl; X is $SO_2$; $R_1$ is preferably ethyl; $X_1$ is preferably N-methyl; $R_3$ is hydrogen and $R_7$ is preferably hydrogen or $C_1$-$C_2$haloalkyl.

In said preferred group of compounds of formula I-1, Q is selected from the group consisting of J-0 to J-31 (where the arrow represents the point of attachment of the heterocycle to the radical Q)
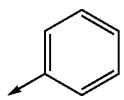 J-0
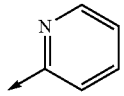 J-1
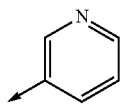 J-2
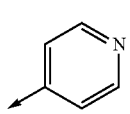 J-3
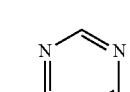 J-4
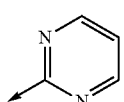 J-5
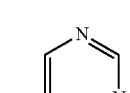 J-6
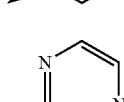 J-7
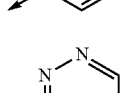 J-8
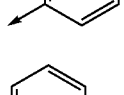 J-9
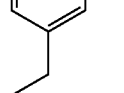 J-10
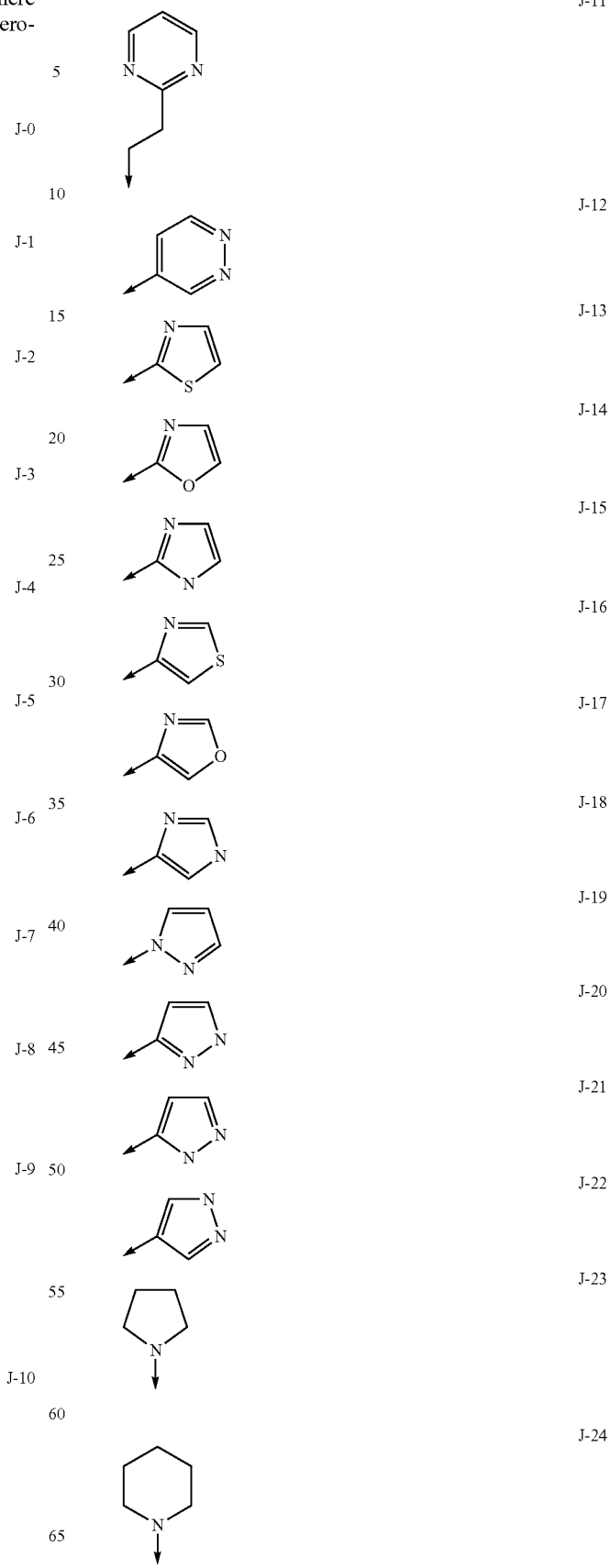

-continued

J-25

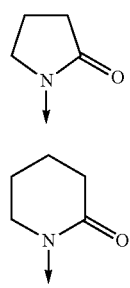

J-26

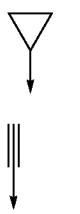

J-27

J-28

J-29

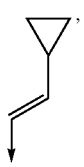

J-30

J-31 wherein each group J-0 to J-8 and J-12 to J-26 can be mono- di- or trisubstituted with Rx, wherein each Rx, independently from each other, is selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; wherein the group J-27 can be mono- di- or trisubstituted with Rx, wherein each Rx, independently from each other, is halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and $C_1$-$C_4$haloalkylcarbonyl; wherein the aromatic part of the group J-9 to J11 can be mono- di- or trisubstituted with Rx, wherein each Rx, independently from each other, is selected from the group consisting of halogen, cyano, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy.

Further preferred compounds of formula I are represented by the compounds of formula I-2

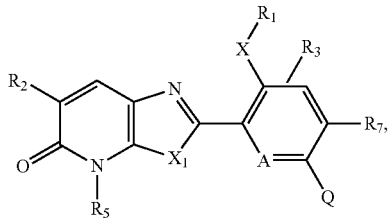

(I-2)

wherein $R_2$, A, X and Q are as defined under formula I above; $R_5$ is as defined under formula I above, preferably $C_1$-$C_4$alkyl; $R_1$ is methyl, ethyl, n-propyl, i-propyl or cyclopropylmethyl; $R_3$ is hydrogen; $R_7$ is hydrogen, halogen or $C_1$-$C_3$haloalkyl; $X_1$ is N-methyl, oxygen or sulfur; and agrochemically acceptable salts, stereoisomers, enantiomers, tautomers and N-oxides of the compounds of formula I-2.

In said preferred group of compounds of formula I-2, $R_2$ is preferably $C_1$-$C_4$haloalkyl, halogen, $C_1$-$C_4$haloalkylsulfanyl, $C_1$-$C_4$haloalkylsulfinyl or $C_1$-$C_4$haloalkylsulfonyl; X is $SO_2$; $R_1$ is preferably ethyl; $X_1$ is preferably N-methyl; $R_3$ is hydrogen and $R_7$ is preferably hydrogen or $C_1$-$C_2$haloalkyl.

In said preferred group of compounds of formula I-2, Q is selected from the group consisting of J-0 to J-31 (where the arrow represents the point of attachment of the heterocycle to the radical Q)

J-0

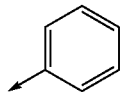

J-1

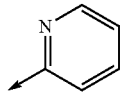

J-2

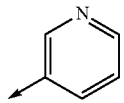

J-3

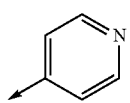

J-4

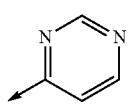

J-5

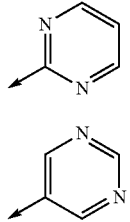

J-6

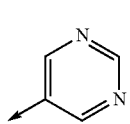

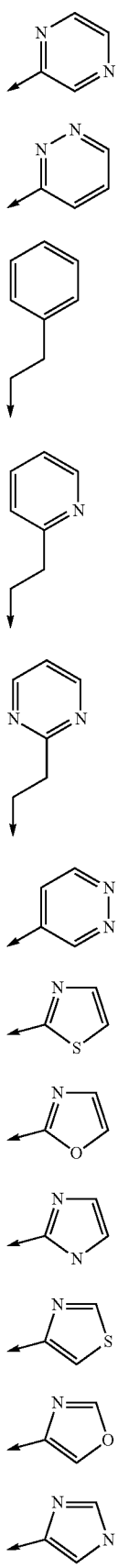
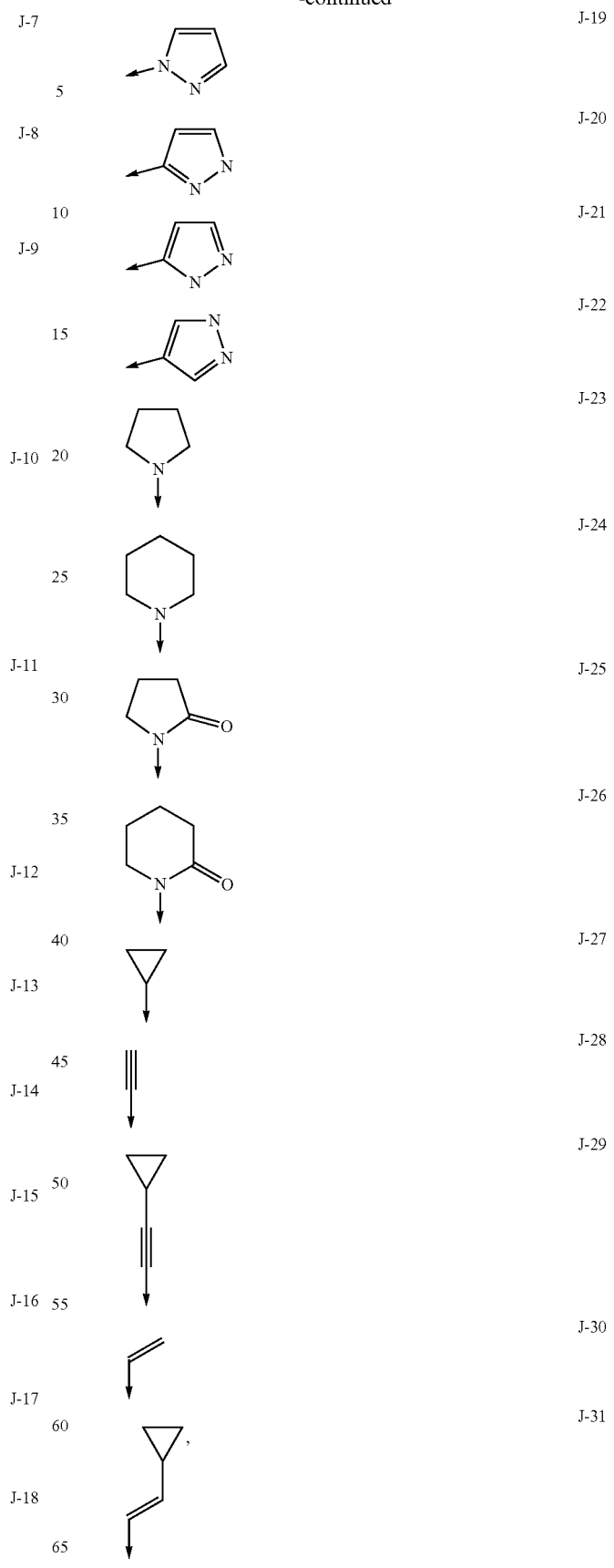

wherein each group J-0 to J-8 and J-12 to J-26 can be mono- di- or trisubstituted with Rx, wherein each Rx, independently from each other, is selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; wherein the group J-27 can be mono- di- or trisubstituted with Rx, wherein each Rx, independently from each other, is halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and $C_1$-$C_4$haloalkylcarbonyl; wherein the aromatic part of the group J-9 to J11 can be mono- di- or trisubstituted with Rx, wherein each Rx, independently from each other, is selected from the group consisting of halogen, cyano, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy.

In particular preferred compounds of formula I-1 are those of formula I-1a

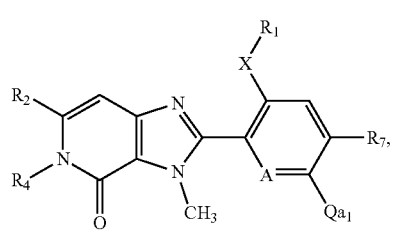
(I-1a)

wherein
A is N or CH;
X is S or $SO_2$;
$R_1$ is $C_1$-$C_4$alkyl;
$R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
$R_4$ is $C_1$-$C_4$alkyl;
$R_7$ is hydrogen or $C_1$-$C_2$haloalkyl; and
$Q_{a1}$ is selected from the group consisting of

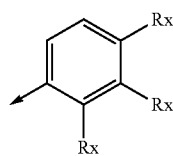
J-0a

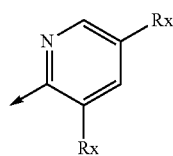
J-1a

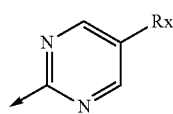
J-5a

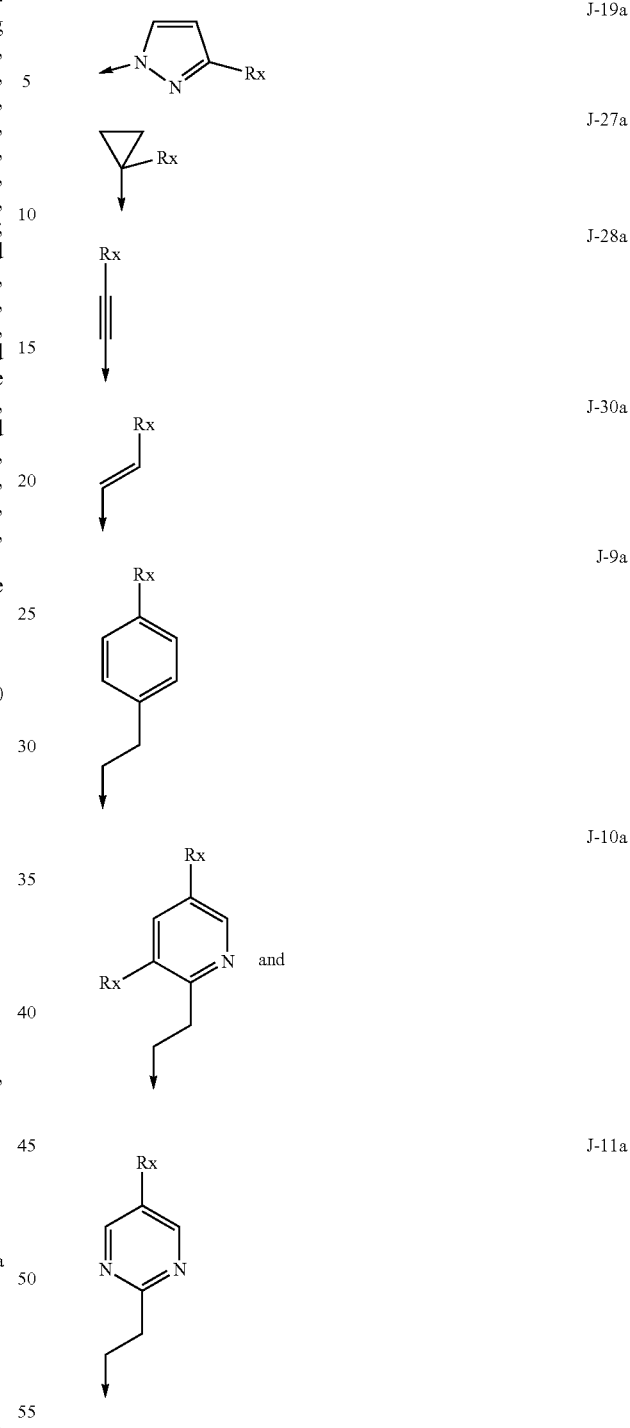

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy and $C_1$-$C_4$alkoxy.

More preferred compounds of formula I-1a are those, in which each Rx is, independently from each other, selected from the group consisting of hydrogen, halogen, cyano, $C_1$-$C_4$alkyl and $C_1$-$C_4$haloalkyl.

An even more preferred group of compounds of formula I-1a is represented by the compounds of formula I-1a1

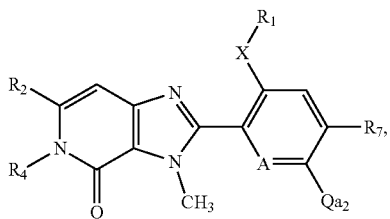
(I-1a1)

wherein
A is N or CH;
X is S or $SO_2$;
$R_2$ is $C_1$-$C_2$haloalkyl, $C_1$-$C_2$haloalkylsulfanyl, $C_1$-$C_2$haloalkylsulfinyl or $C_1$-$C_2$haloalkylsulfonyl;
$R_7$ is hydrogen or $C_1$-$C_2$haloalkyl;
$R_4$ is $C_1$-$C_4$alkyl and
$Q_{a2}$ is selected from the group consisting of

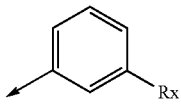
J-0aa

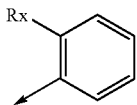
J-1a

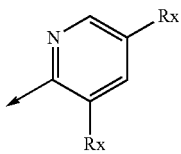
J-5a

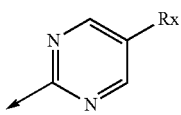
J-19a

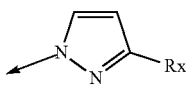
J-27a wherein each Rx, independently from each other, is selected from the group consisting of hydrogen, halogen, $C_1$-$C_4$alkyl and $C_1$-$C_4$haloalkyl.

In said preferred compounds of formula I-1a1, Rx is, independently from each other, preferably selected from the group consisting of halogen, hydrogen and $C_1$-$C_4$haloalkyl; $R_1$ is preferably ethyl; and $R_4$ is preferably methyl or ethyl.

Particular preferred compounds of formula I-1a1 are those, in which $Q_{a2}$ is selected from the following J-0a, J-0b, J-0c, J-1a, J-5a, J-19a and J-27a;

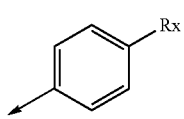
J-0a

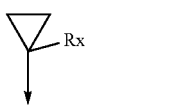
J-0b

J-0c

J-1a

J-5a

J-19a

J-27a wherein each Rx is, independently from each other, selected from the group consisting of hydrogen, halogen and $C_1$-$C_4$haloalkyl.

Particular preferred compounds of formula I-1 are those of formula I-2a

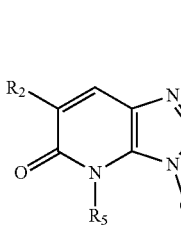
(I-2a)

wherein
A is N or CH;
X is S or $SO_2$;
$R_1$ is $C_1$-$C_4$alkyl;
$R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
$R_5$ is $C_1$-$C_4$alkyl;
$R_7$ is hydrogen or $C_1$-$C_2$haloalkyl; and
$Q_{a1}$ is selected from the group consisting of the substituents

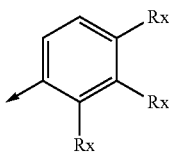
J-0aa

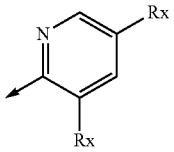
J-1a

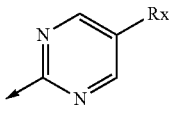
J-5a

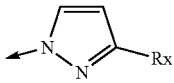
J-19a

J-27a

J-28a

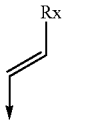
J-30a

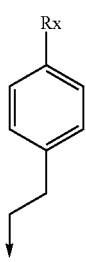
J-9a

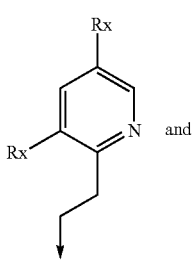
J-10a and

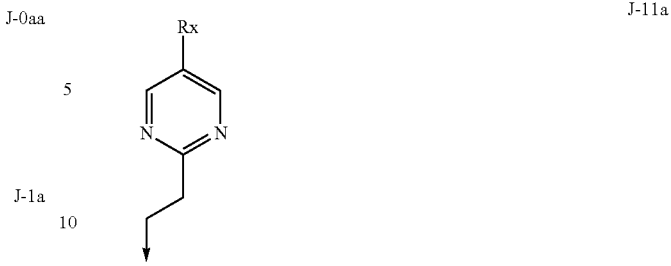
J-11a wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy and $C_1$-$C_4$alkoxy.

More preferred compounds of formula I-2a are those, in which each Rx is, independently from each other, selected from the group consisting of hydrogen, halogen, $C_1$-$C_4$alkyl and $C_1$-$C_4$haloalkyl.

An especially preferred group of compounds of formula I-2a are represented by the compounds of formula I-2a2

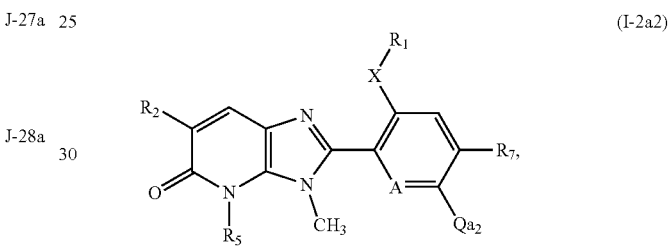
(I-2a2)

wherein
A is N or CH;
$R_2$ is $C_1$-$C_2$haloalkyl, $C_1$-$C_2$haloalkylsulfanyl, $C_1$-$C_2$haloalkylsulfinyl or $C_1$-$C_2$haloalkylsulfonyl;
$R_7$ is hydrogen or $C_1$-$C_2$haloalkyl;
$R_5$ is $C_1$-$C_4$alkyl; and
$Q_{a2}$ is selected from the group consisting of the substituents

J-0aa

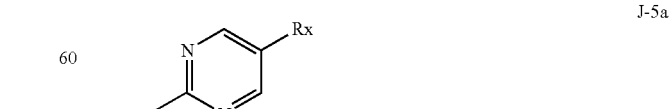
J-1a

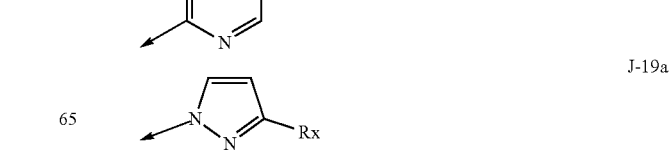
J-5a

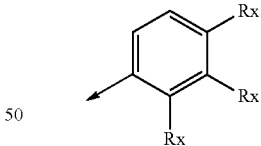
J-19a

-continued

J-27a

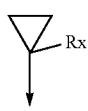

wherein each Rx, independently from each other, is selected from the group consisting of hydrogen, halogen, C₁-C₄alkyl and C₁-C₄haloalkyl.

In said preferred compounds of formula I-2a2, Rx is, independently from each other, preferably selected from the group consisting of halogen, hydrogen or C₁-C₄haloalkyl; R₁ is preferably ethyl; and R₅ is preferably methyl or ethyl.

In particular preferred compounds of formula I-2a2 are those, in which Q$_{a2}$ is selected from the following J-0a, J-0b, J-0c, J-1a, J-5a, J-19a and J-27a;

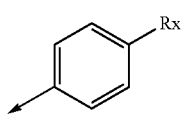  J-0a

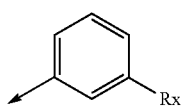  J-0b

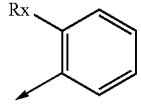  J-0c

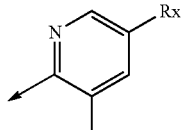  J-1a

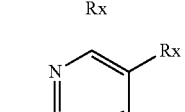  J-5a

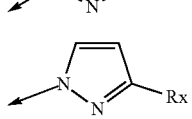  J-19a

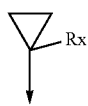  J-27a

In all of the preferred embodiments of the compounds of formula I mentioned above, the substituents Q, Qa₁ and Qa₂ are preferably selected from the group consisting of
a) phenyl, which can be substituted by halogen or C₁-C₄haloalkyl;
b) pyrazole, which can be substituted by C₁-C₄haloalkyl; and
c) C₂-C₆alkenyl, which can be substituted by phenyl, wherein said phenyl can be mono-, di- or trisubstituted by halogen.

A preferred group of compounds of formula I is represented by the compounds of formula I-1

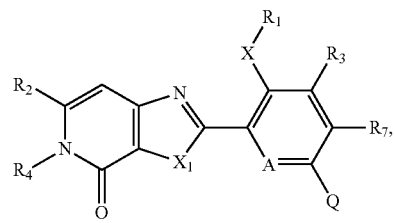  (I-1)

wherein R₃ and R₇ are hydrogen;
A is C or N;
R₄ is C₁-C₃alkyl or cyclopropyl;
R₂ is C₁-C₂haloalkyl;
X₁ is N—CH₃;
X is S, SO or SO₂;
R₁ is C₁-C₃alkyl;
Q is selected from the group consisting of J-0, J-2, J-3, J6, J-19, J-27, K-13, K-14, K-15, K-30, K-31, K-32 and K-33

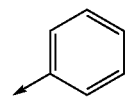  J-0

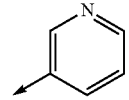  J-2

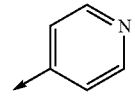  J-3

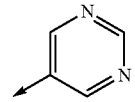  J-6

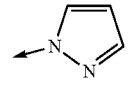  J-19

  J-27

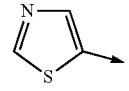  K-13

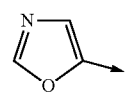  K-14

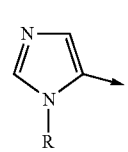  K-15

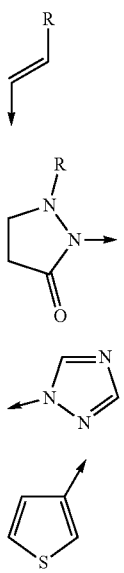

R is $C_1$-$C_2$alkyl;

J-0, J-2, J-3, J6, J-19, K-13, K-14 and K-15 can be mono- or disubstituted by substituents independently selected from the group consisting of halogen, trifluoromethyl, $C_1$-$C_2$alkyl, methoxy, methylsulfanyl, trifluoromethoxy and cyano.

The process according to the invention for preparing compounds of formula (I) is carried out by methods known to those skilled in the art, or/and described, by analogy, for example in WO 2009/131237, WO 2011/043404, WO 2011/040629, WO 2010/125985, WO 2012/086848, WO 2013/018928, WO 2013/191113, WO 2013/180193, WO 2013/180194 and comprises reaction of a compound of formula II,

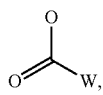
(II)

wherein W is the group

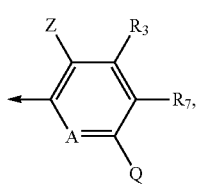
(W)

wherein Z is X—$R_1$ or a leaving group, for example a halogen, and wherein Q, X, $R_1$, $R_3$, $R_7$ and A are as described under formula I above, and wherein the arrow in the radical W shows the point of attachment to the carbon atom of the carboxyl group in the compound of formula II, with a compound of formula III,

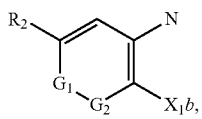
(III)

wherein $R_2$, $G_1$ and $G_2$ are as described under formula I above and $X_{1b}$ is $NHR_6$, OH or SH, in the presence of a dehydrating agent, such as for example polyphosphoric acid at temperature between 150° C. to 250° C., to yield compounds of formula Ia, wherein the substituents are as described above and under formula I.

Such processes are well known and have been described by analogy, for example in WO 2008/128968, WO 2006/003440, Bioorganic & Medicinal Chemistry 2013, 21(15), 4559-4569, Analytica Chimica Acta 2013, 786, 139-145 or Journal of Medicinal Chemistry, 57(3), 828-835; 2014 (and supplementary material). The process is summarized in scheme 1 for compounds of formula Ia Scheme 1

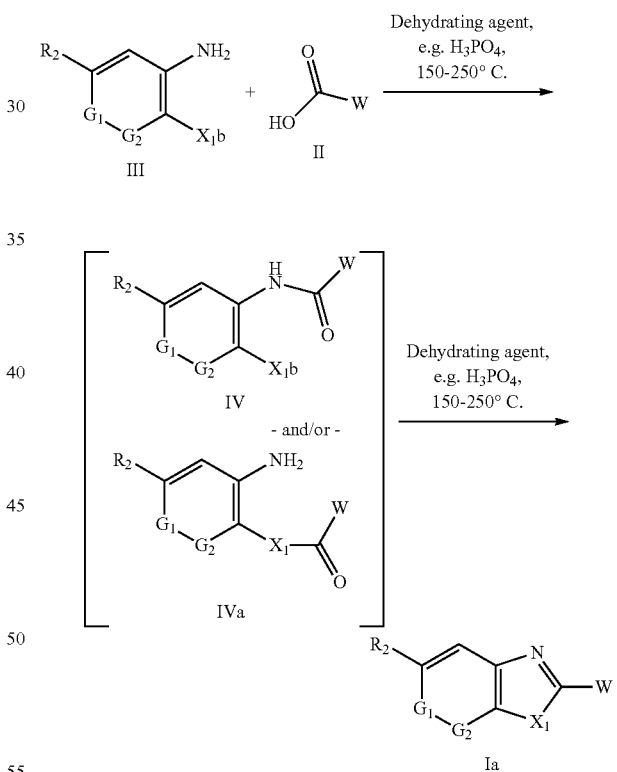

As can be seen in scheme 1, the formation of compounds of formula Ia occurs through the intermediacy of a compound of formula IV (and/or its position isomer IVa). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2

Scheme 2

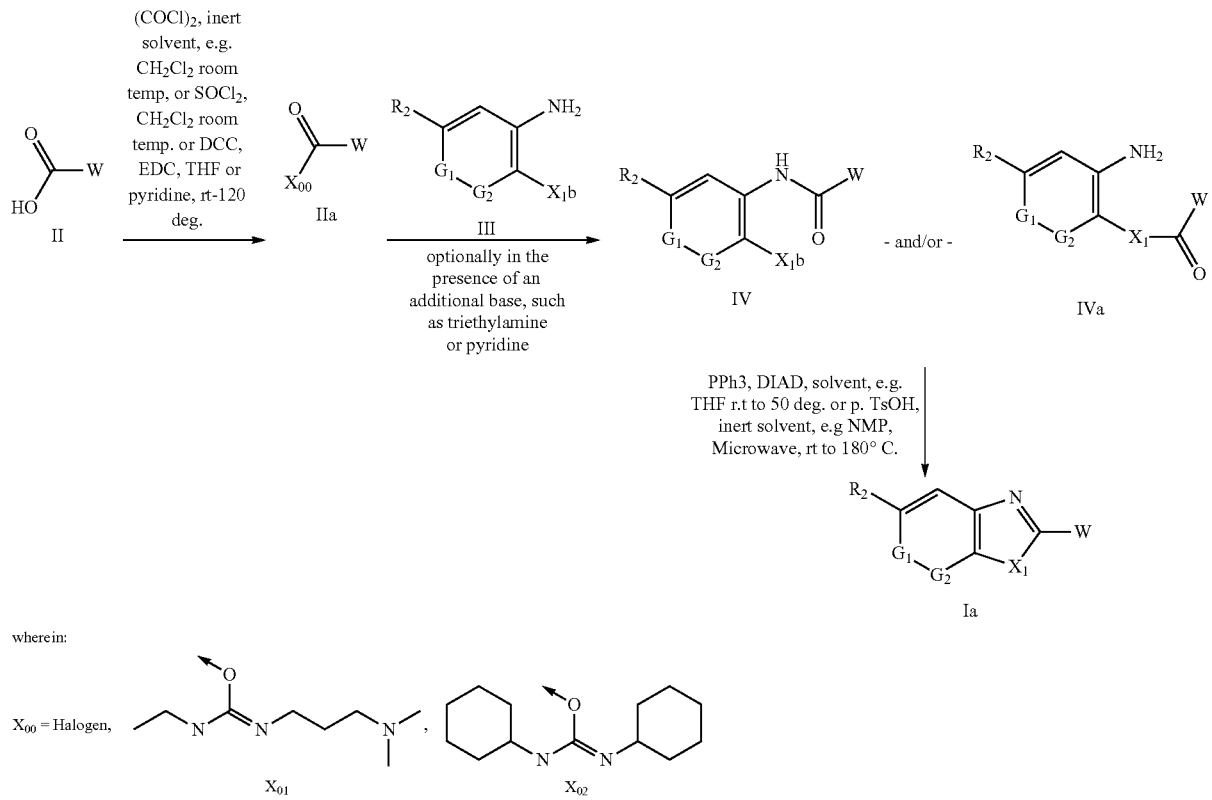

Compounds of the formula IV and/or IVa (or a mixture thereof), or a salt thereof, wherein W is as defined above, and wherein $X_1$, $R_2$, $G_1$ and $G_2$ are as described under formula I above and $X_{1b}$ is $NHR_6$, OH or SH, may be prepared by i) activation of compound of formula II, wherein W is as defined above, by methods known to those skilled in the art and described in, for example, Tetrahedron, 2005, 61 (46), 10827-10852, to form an activated species IIa, wherein W is as defined above. For example, compounds IIa where $X_{00}$ is halogen, preferably chlorine, are formed by treatment of II with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran (THF) at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_2$, $G_1$ and $G_2$ are as described under formula I above and $X_{1b}$ is $NHR_6$, OH or SH, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof) wherein W is as defined above, and wherein $X_1$, $R_2$, $G_1$ and $G_2$ are as described under formula I above and $X_{1b}$ is $NHR_6$, OH or S.

Compounds of formula IV and/or IVa (or a mixture thereof) may further be converted into compounds of formula Ia, wherein W is as defined above, and wherein $X_1$, $R_2$, $G_1$ and $G_2$ are as described under formula I above, by dehydration, eg. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine NMP at temperatures between 25-180° C., preferably 100-170° C., optionally under microwave conditions. Such processes have been described previously, for example, in WO 2010/125985.

Compounds of formula Ia, wherein Z is a leaving group, for example halogen, preferably fluorine or chlorine, and wherein A, $R_2$, $R_3$, $R_7$, $X_1$, $G_1$ and $G_2$ are as described under formula I above, can be reacted with compounds of formula V $$R_1\text{—SH} \quad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which A, $R_7$, $R_3$, $R_2$, $G_1$ and $G_2$ are as described under formula I above and X is sulfur. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO 2013/018928. Examples of salts of the compound of formula V include compounds of the formula Va $$R_1\text{—S-M} \quad (Va),$$

wherein $R_1$ is as defined above and wherein M is, for example, sodium or potassium. This is illustrated for compounds of formula Ib in scheme 3

Scheme 3

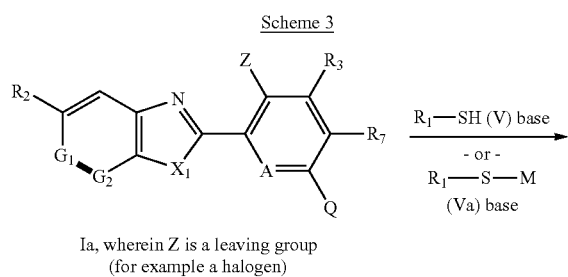

Ia, wherein Z is a leaving group
(for example a halogen)

Ib, that is a compound of
formula I wherein X is sulfur
(a sulfide)

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described, for example by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X is SO), and preferably 2 to 2.2 moles of oxidant, relative to 1 mole of the sulfide compounds Ib to produce the sulfone compounds I (wherein X is $SO_2$). Such oxidation reactions are disclosed, for example, in WO 2013/018928. This reaction could be apply at any intermediates or final compounds to obtain compounds of formula I, wherein X is SO (sulfoxide) and/or $SO_2$ (sulfone) from compounds wherein X is S.

For example, the sequence to prepare compounds of formula IIIa wherein $R_2$, $R_4$ and $R_6$ are as described under formula I above, from compounds of formula VIII, may involve i. alkylation of compound VIII with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula VII, wherein $R_6$, $R_4$ and $R_2$ are as described under formula I above; ii. a reaction of nitration of compound VII in classical conditions, for example, see for example, Advanced Organic Chemistry: Reactions, Mechanisms, and Structure, Fourth Edition by Jerry March, 1992 (Publisher Wiley New York, N.Y.) pages 523-525; and finally iii. a reaction of reduction of compound VI in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 4.

Scheme 4

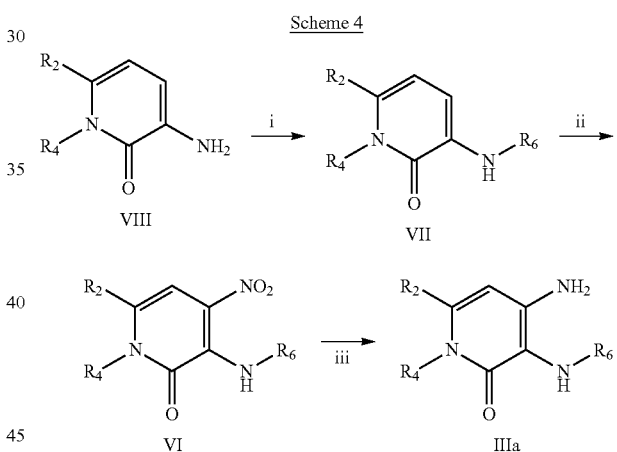

Compounds of formula VIII may be made by methods known to a person skilled in the art, for example Synthesis 2005, No. 8, pp 1269-1278 and Synthesis 2011, No. 7, pp 1149-1156.

Compounds of formula I-1b, wherein Z is X—$R_1$ or a leaving group, for example halogen, and wherein X, $R_1$, $R_4$, $R_6$, A and $R_2$ are as described under formula I above, may be prepared by reaction between compounds of formula IIa (activate form of Compound of formula II, illustrated, for example by $X_{00}$) or compounds of formula II, wherein Z is X—$R_1$ or a leaving group, for example halogen, and wherein X, R, and A are as described under formula I above, and in which $X_{00}$ is as described above, and compounds of formula IIIa, wherein $R_6$ and $R_2$ are as described under formula I above, under similar conditions as for the preparation of compounds of formula Ia from compounds of formula II/IIa and III described above (see scheme 1 and 2). This is illustrated for compounds of formula IIIa in scheme 5: Scheme 5

Scheme 5

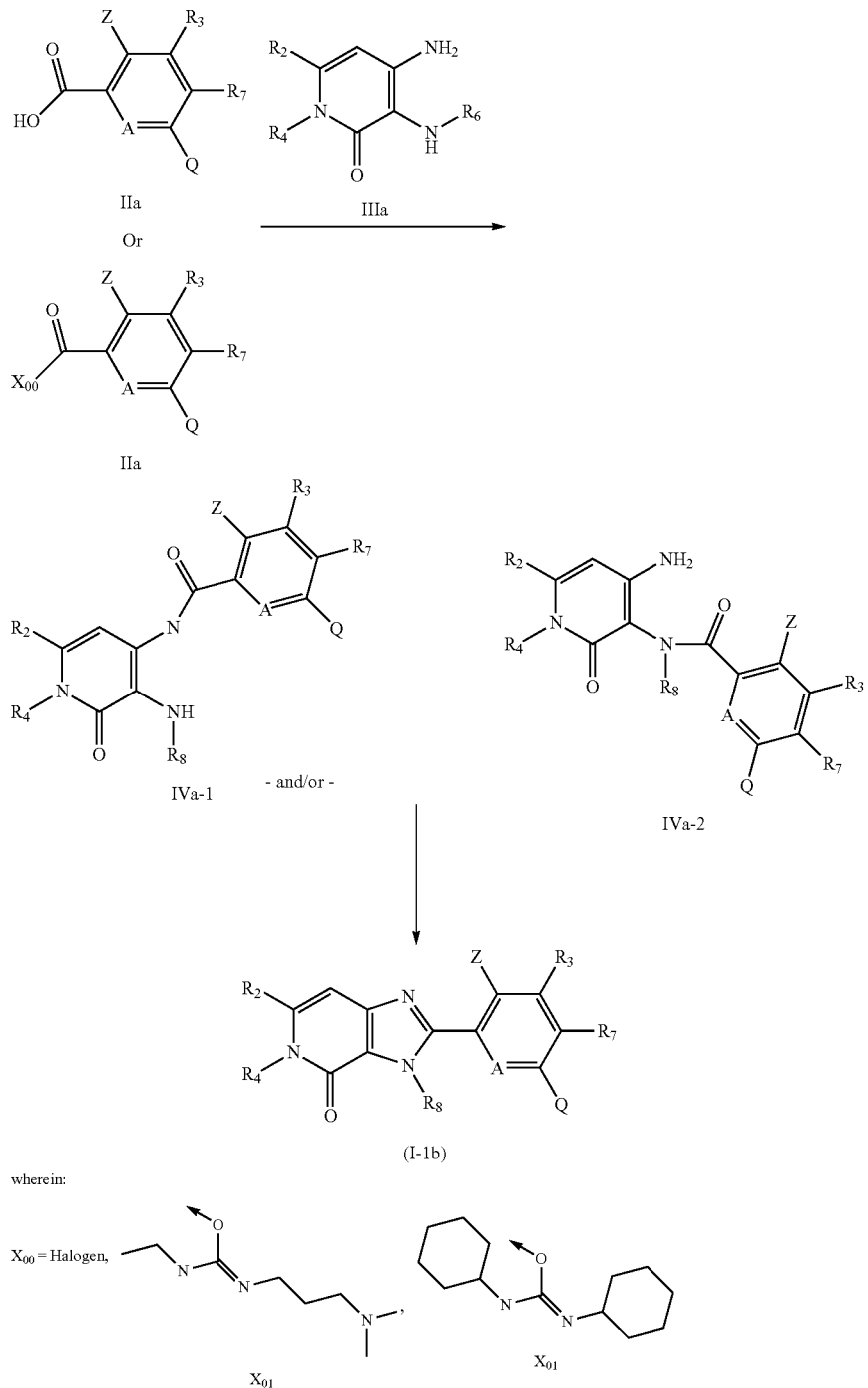

Alternatively, the sequence to prepare compounds of formula IIIb wherein $R_2$, $R_5$ and $R_6$ are as described under formula I above, from compounds of formula XII, may involve i. alkylation of compound XII with $R_5$—$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula XI, wherein $R_6$, $R_5$ and $R_2$ are as described under formula I above; ii. a reaction of Vicarious nucleophilic substitution (VNS) reaction of compound XI in classical conditions, for example, J. Org. Chem., Vol. 61, No. 2, 1996 p 442; iii. alkylation of compound X with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IX, wherein $R_6$, $R_5$ and $R_2$ are as described under formula I above and finally iv. a reaction of reduction of compound IX in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 6.

Compounds of formula I-2b, wherein Z is $X-R_1$ or a leaving group, for example halogen, and wherein Q, X, $R_1$, $R_2$, $R_5$, $R_6$, Q and A are as described under formula I above, may be prepared by reaction between compounds of formula II or IIa, wherein Z is $X-R_1$ or a leaving group, for example halogen, and wherein Q, X, $R_1$, $R_3$, $R_7$ and A are as described under formula I above, and in which $X_{00}$ is as described above, and compounds of formula IIIb, wherein $R_5$, $R_6$ and $R_2$ are as described under formula I above, under similar

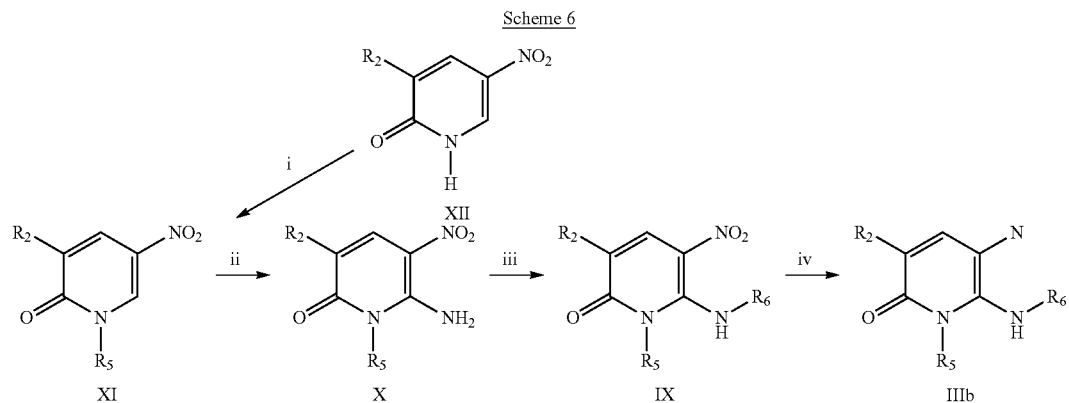

Compounds of formula XII are commercially available or may be made by methods known to a person skilled in the art.

conditions as for the preparation of compounds of formula Ia from compounds of formula II or IIa and III described above (see scheme 1 and 2). This is illustrated in scheme 7

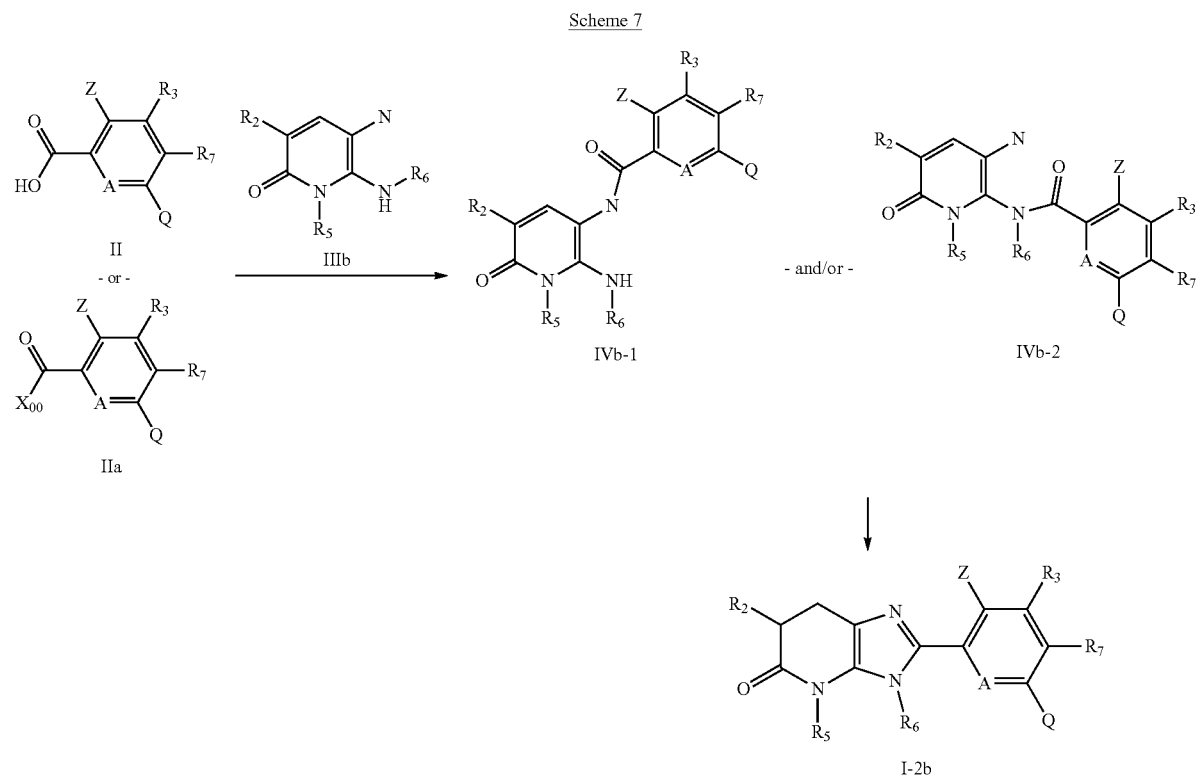

wherein:

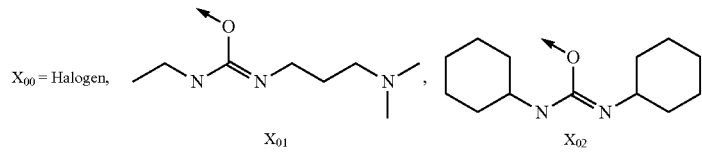

$X_{00}$ = Halogen,

Compounds of formula I, wherein A, $R_1$, $R_2$, $R_3$, $R_7$, $G_1$, $G_2$, X, $X_1$ and Q are as defined in formula I above, can be prepared (as shown in scheme 8) by a Suzuki reaction, which involves for example, reacting compounds of formula XIV, wherein LG is a leaving group, for example, chlorine, bromine or iodine, or an aryl- or alkylsulfonate such as trifluoromethanesulfonate with compounds of formula XIIIa, wherein $Y_{b1}$ can be a boron-derived functional group, as for example B(OH)$_2$ or B(OR$_{b1}$)$_2$ wherein R$_{b1}$ can be a $C_1$-$C_4$alkyl group or the two groups OR$_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, or of dioxane and water, preferably under an inert atmosphere. The reaction temperature can preferentially range from room temperature to the boiling point of the reaction mixture. Such Suzuki reactions are well known to those skilled in the art and have been reviewed, for example *J. Orgmet. Chem.* 576, 1999, 147-168.

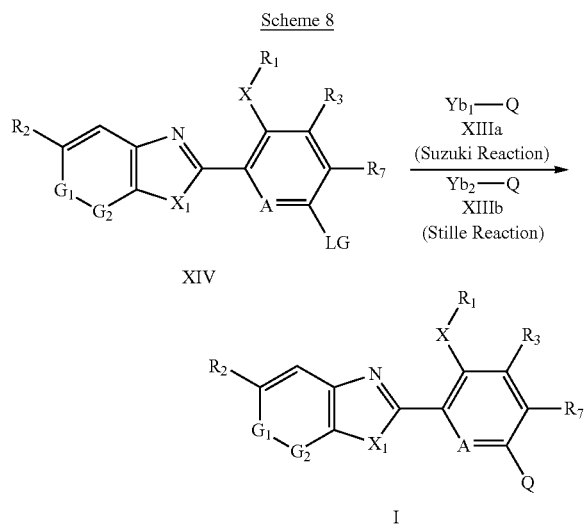

Scheme 8

Alternatively, compounds of formula I can be prepared by a Stille reaction of compounds of formula XIIIb wherein $Y_{b2}$ is a trialkyl tin derivative, preferably tri-n-butyl tin, with compounds of formula XIV. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

In the particular case where compounds of formula I have the group Q attached through a nitrogen atom (i.e. those situations where Q is a nitrogen containing heteroaromatic system), these compounds can be advantageously accessed by reacting a compound of the formula XIV, wherein LG is a leaving group like, for example, chlorine, bromine or iodine with a compound of the formula XV (H-Q), wherein Q is as described in compounds of formula I, with the condition that the attachment point is a nitrogen atom. This reaction is well known in the literature (call Ullmann reaction or variation around this type of reaction), see for example Coord. Chem. Rev. 2004, 248, 2337-2364, Tetrahedron, 67(29), 5282-5288; 2011, Angew. Chem., Int. Ed. 2003, 42, 5400-5449; Synlett 2003, 2428-2439; (d) Manifar, T.; Ind. Eng. Chem. Res. 2005, 44, 789-798. The reaction is commonly performed with one to two equivalents of a base, like potassium phosphate, in presence of a copper catalyst, like for example copper (I) iodine and under an oxygen-containing atmosphere. The reaction can be run in an inert solvent, like dioxane or toluene, usually at temperature between 50 to 150° C. and in presence or not of a additional ligand such as for example diamine ligands (e.g. trans-cyclohexyldiamine.) or, for example, dibenzylideneacetone (dba) and 1,10-phenanthroline. Alternatively compounds of formula I can be prepared from compounds of formula Iaa wherein A, $G_1$, $G_2$, $R_1$, $R_2$, $R_3$, $R_7$, X, $X_1$, and Q are as previously defined and wherein LG is a leaving group like, for example, fluorine or chlorine, by reaction of the heterocycle H-Q (which contains a an appropriate NH functionality), in the presence of a base, for example an alkaline metal hydride such as sodium hydride, or an alkali metal carbonate, for example cesium or potassium carbonate, in an appropriate solvent such as N-methyl pyrollidone or DMF at temperatures between 30-150° C. The reaction is illustrated, for example, when H-Q is the heterocycle J-19 in scheme 9, which gives compounds of formula Iaa.

Scheme 9

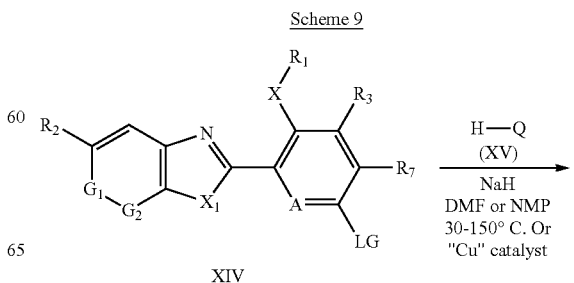

-continued

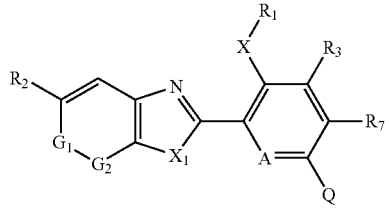

Iaa

For example, H—Q is 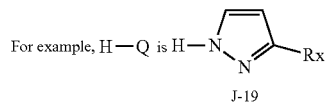

J-19

Compounds of formula XIVa, wherein A is nitrogen and $G_1$, $G_2$, $R_1$, $R_2$, $R_3$, $R_7$, X and $X_1$ are as previously defined in formula I, and LG is chlorine or bromine, can be prepared according to the methods shown in scheme 10

Scheme 10.

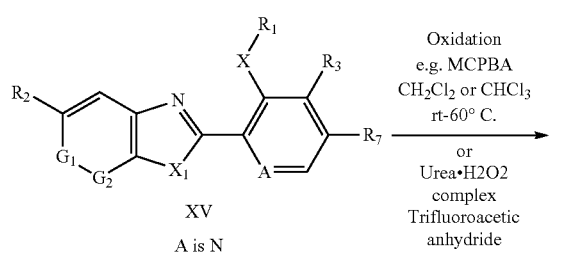

XV
A is N
X is S

Oxidation
e.g. MCPBA
$CH_2Cl_2$ or $CHCl_3$
rt-60° C.
or
Urea•H2O2 complex
Trifluoroacetic anhydride
CH2Cl2, rt

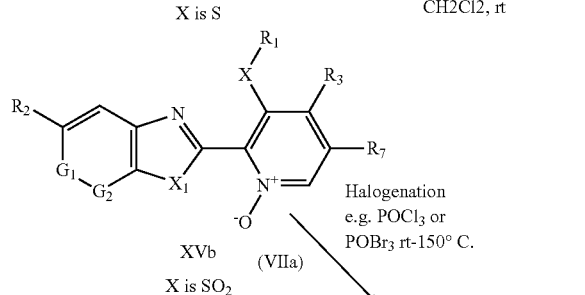

XVb
X is $SO_2$

Halogenation
e.g. $POCl_3$ or
$POBr_3$ rt-150° C.

(VIIa)

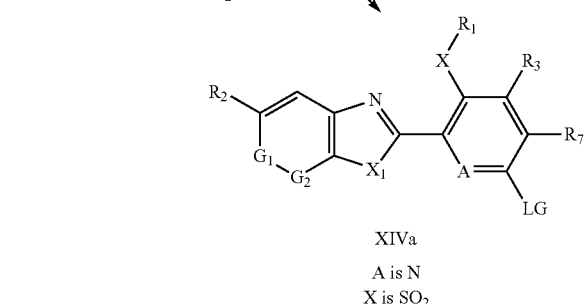

XIVa
A is N
X is $SO_2$

Thus, compounds of formula XV are oxidized by methods known to those skilled in the art and described in for example, in WO 2010/125985, to give compounds of formula XVb, A is nitrogen oxide, X is $SO_2$ and $G_1$, $G_2$, $R_1$, $R_2$, $R_3$, $R_7$ and $X_1$ are as previously defined in formula I. Compounds of formula XVb upon treatment with phosphorus oxychloride or phosphorus oxychloride, optionally in the presence of a base, such as triethylamine, and optionally in a solvents, for example dichloromethane, DMF, or dioxane (see for example *Syn. Comm.*, 31(16), 2507-2511, 2001) can give compounds of formula XIVa wherein A is nitrogen, X is $SO_2$ and $G_1$, $G_2$, $R_1$, $R_2$, $R_3$, $R_7$ and $X_1$ are as previously defined in formula I and LG is chloride or bromide.

Compounds of formula XIV wherein A is CH and $G_1$, $G_2$, $R_1$, $R_2$, $R_3$, $R_7$, X and $X_1$ are as previously defined in formula I, and LG is chlorine or bromine, can be prepared according to the methods shown in scheme 11

Scheme 11

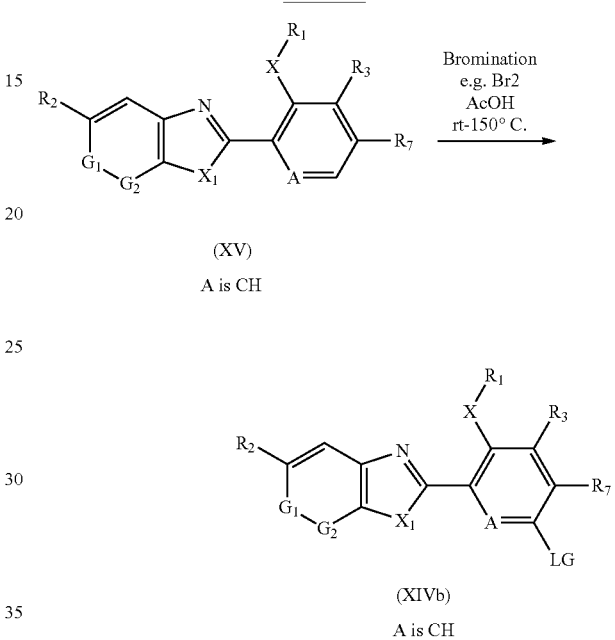

Compounds of formula XV, wherein A is CH and $G_1$, $G_2$, $R_1$, $R_2$, $R_3$, $R_7$, X and $X_1$ are as previously defined in formula I, can be halogenated to compounds of formula XIVb, wherein A is CH and $G_1$, $G_2$, $R_1$, $R_2$, $R_3$, $R_7$, X and $X_1$ are as previously defined in formula I and LG is chloride or bromide, for example with bromine or chlorine in an appropriate solvent, for example glacial acetic acid, at temperatures between 0° C. and 150° C., optionally in a microwave reactor. Alternatively, the reaction may be carried out in the presence of a Lewis acid catalyst, for example iron, or Aluminum trichloride (Friedel-Craft halogenation). Similar reactions have been described I the literature (see for example Ger. Offen., 19840337, 2000, *Med. Chem. Lett.*, 3(6), 450-453; 2012 and Macromolecules, 47(14), 4607-4614; 2014). Alternatively compounds of formula XIV, XIVa or XIVb can be prepared by a similar reaction described in scheme 1 and 2 using the corresponding acid that can be prepared by methods known to those skilled in the art.

Compounds of formula I, wherein Y is S, can be prepared (scheme 12) by reacting compounds of formula I-1 or I-2, wherein Y is O with a reagent that could transfer a sulphur atom such as, for example, the Lawesson's reagent in a solvent such as, for example dimethylformamide or toluene, usually at temperature between 50 to 150° C. This type of transformation is known to a person skilled in the art and are, for example, described in Tetrahedron (2007), 63(48), 11862-11877 or US20120309796.

Scheme 12

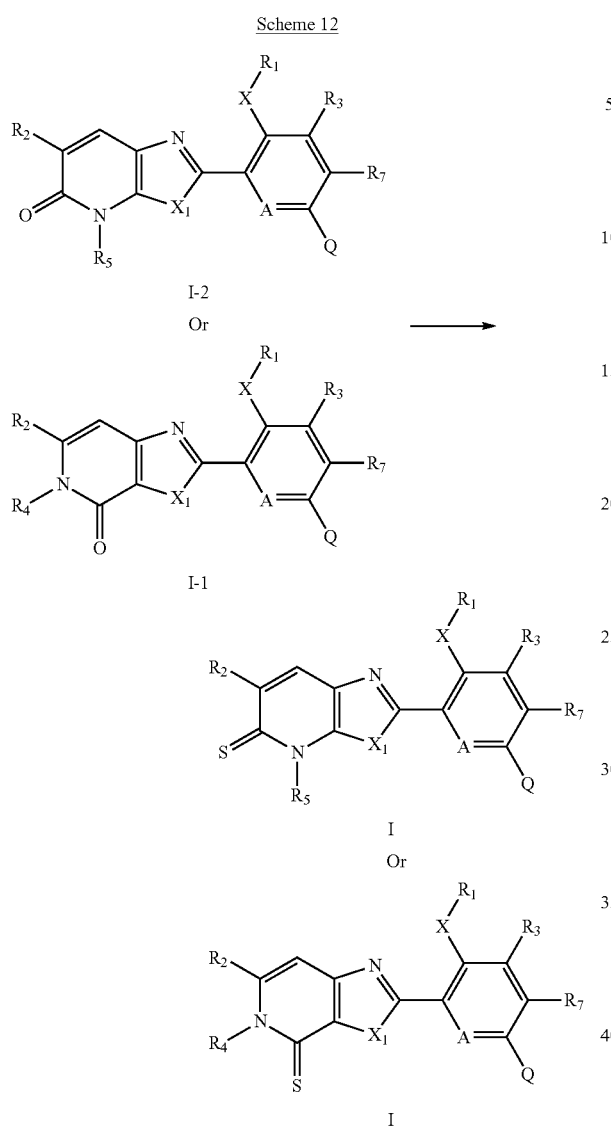

Alternatively, the O of the C(O) can be transformed on S on previews intermediate such as for example, compounds of formula XI, XII, X, IX, VIII, VII, VI, IIb or IIIa.

Compounds of formula I-1, wherein X, $X_1$, $R_1$, $R_2$, $R_3$, $R_6$, $R_7$, A and Q are as described under formula I above, could be prepared from compounds of formula (XVI).

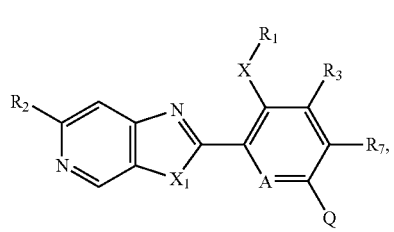

wherein X, $X_1$, $R_1$, $R_2$, $R_3$, $R_6$, $R_7$, A and Q are as described under formula I above, via formation of an N-oxide of formula XVIa, followed by rearrangement to a compound of formula XVII and alkylation of compound XVII with a reagent of formula $R_4$—$X_{LG}$. This is illustrated for compounds of formula I-1, from compounds of formula XVIII, in scheme 13

Scheme 13

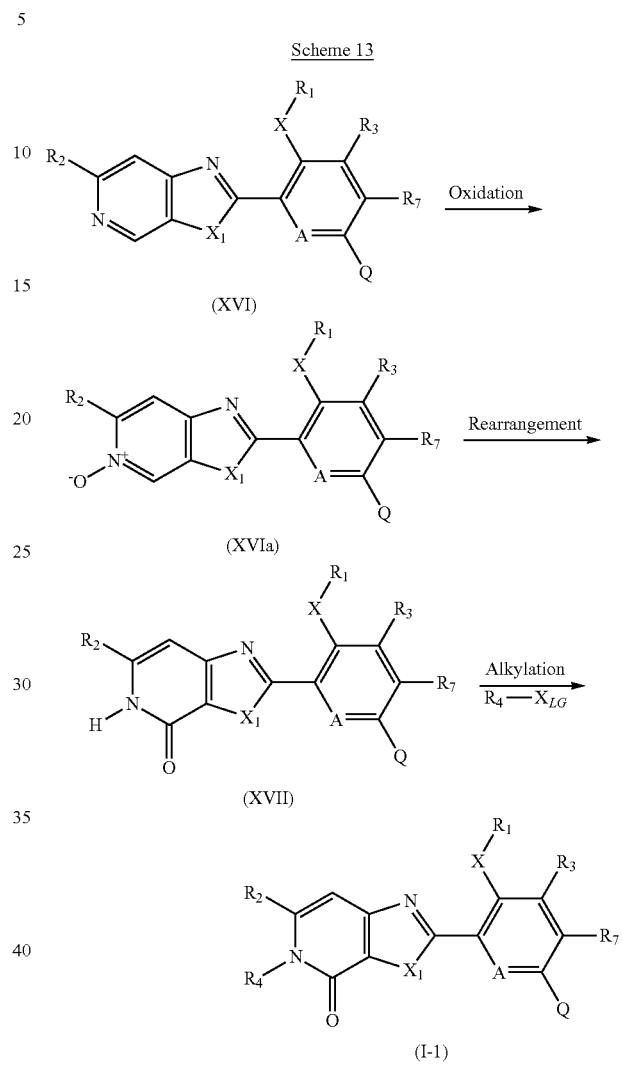

N-oxide compounds of formula (XVIa), wherein X, $X_1$, $R_1$, $R_2$, $R_3$, $R_6$, $R_7$, A and Q are as described under formula I above, may be prepared from a compound of formula (XVI), via oxidation by reaction with a suitable oxidizing agent, such as meta-perbenzoic acid or hydrogen peroxide in the appropriate inert solvent, such as for example dichloromethane or chloroform. Such oxidations are known from the literature, for example from WO 2013/018928, WO 2010/073128 or Synthetic Communications 2013, 43(8), 1092-1100.

Compounds of formula XVII may be prepared from a compound of formula (XVIa), wherein X, $X_1$, $R_1$, $R_2$, $R_3$, $R_6$, $R_7$, A and Q are as described under formula I above, via rearrangement, for example mediated by anhydride reagents, such as trifluoroacetic anhydride, in the appropriate solvent, such as N,N-dimethylformamide. Such rearrangement reactions are well known from the literature, for example from Journal of Organic Chemistry 196), 26, 428-430 or Journal of Heterocyclic Chemistry 1976, 13(6), 1197-2000.

Compounds of formula (XVII), wherein X, $X_1$, $R_1$, $R_2$, $R_3$, $R_6$, $R_7$, A and Q are as described under formula I above, may exist in a tautomeric form (XVIIa), or in a mixture thereof.

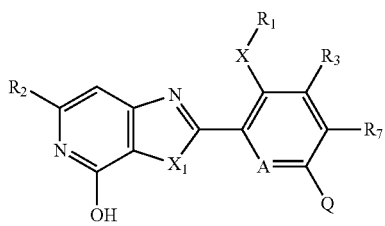

(XVIIa)

Compounds of formula (I-1), wherein X, $X_1$, $R_1$, $R_2$, $R_3$, $R_6$, $R_7$, A and Q are as described under formula I above, and in which $R_4$ is as defined under formula I above, may be prepared from a compound of formula (XVII), via alkylation with a reagent $R_4$—$X_{LG}$, wherein $R_4$ is as described in compounds of formula I and $X_{LG}$ is a leaving group, such as halogen, preferably iodine, bromine or chlorine, in presence of a base, such as cesium carbonate or sodium hydride in a appropriate solvent such as N,N-dimethylformamide, N,N-dimethylacetamide or acetonitrile. Such alkylation is well known from the literature, for example from European Journal of Organic Chemistry 2002 (11), 1763-1769.

Compounds of formula I-2, a subgroup of formula I, X, $X_1$, $R_1$, $R_2$, $R_3$, $R_6$, $R_7$, A and Q are as described under formula I above, can be prepared from compounds of formula (XVIII)

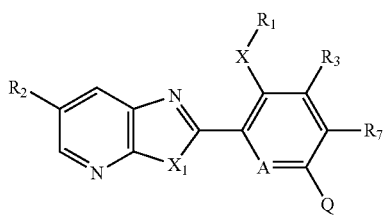

(XVIII)

wherein X, $X_1$, $R_1$, $R_2$, $R_3$, $R_6$, $R_7$, A and Q are as described under formula I above, via formation of an N-oxide of formula XVIIIb, followed by rearrangement to a compound of formula XXI and alkylation of compound XXI with a reagent of formula $R_5$—$X_{LG}$. This is illustrated for compounds of formula I-2, from compounds of formula XVIII in scheme 14

Scheme 14

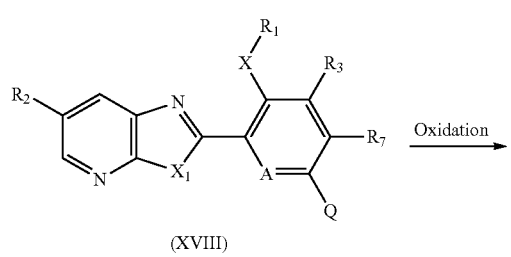

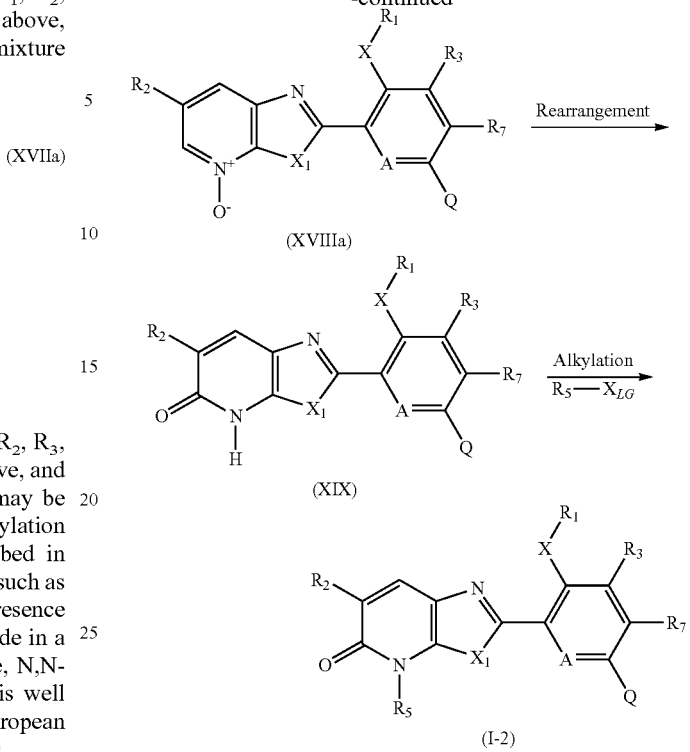

N-oxide compounds of formula (XVIIIa), wherein X, $X_1$, $R_1$, $R_2$, $R_3$, $R_6$, $R_7$, A and Q are as described under formula I above, may be prepared from a compound of formula (XVIII), via oxidation by reaction with a suitable oxidizing agent, such as meta-perbenzoic acid or hydrogen peroxide in the appropriate inert solvent, such as for example dichloromethane or chloroform. Such oxidations are known from the literature, for example from WO 2013/018928, WO 2010/073128 or Synthetic Communications 2013, 43(8), 1092-1100.

Compounds of formula (XIX), wherein X, $X_1$, $R_1$, $R_2$, $R_3$, $R_6$, $R_7$, A and Q are as described under formula I above, may be prepared from a compound of formula (XVIIIa), via rearrangement, for example mediated by anhydride reagents, such as trifluoroacetic anhydride, in the appropriate solvent, such as N,N-dimethylformamide. Such rearrangement reactions are well known from the literature, for example from Journal of Organic Chemistry 196), 26, 428-430 or Journal of Heterocyclic Chemistry 1976, 13(6), 1197-2000.

Compounds of formula (XIX), wherein X, $X_1$, $R_1$, $R_2$, $R_3$, $R_6$, $R_7$, A and Q are as described under formula I above, may exist in a tautomeric form (XIXa), or in a mixture thereof.

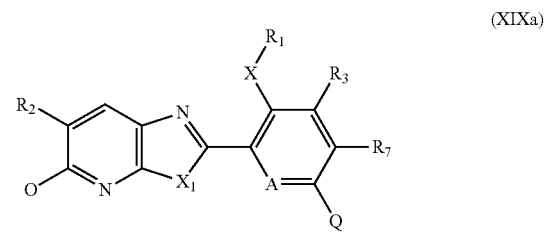

(XIXa)

Compounds of formula (I-2), wherein X, $X_1$, $R_1$, $R_2$, $R_3$, $R_6$, $R_7$, A and Q are as described under formula I above, and in which $R_5$ is as defined under formula I above, may be prepared from a compound of formula (XIX), via alkylation with a reagent $R_5$—$X_{LG}$, wherein $R_5$ is as described in compounds of formula I and $X_{LG}$ is a leaving group, such as halogen, preferably iodine, bromine or chlorine, in presence of a base, such as sodium carbonate, potassium carbonate or cesium carbonate, or sodium hydride in a appropriate solvent such as N,N-dimethylformamide, N,N-dimethylacetamide or acetonitrile. Such alkylation is well known from the literature, for example from European Journal of Organic Chemistry 2002 (11), 1763-1769.

Compounds of formula XVIII, XVIIIa and XIX, wherein X, $X_1$, $R_1$, $R_2$, $R_3$, $R_6$, $R_7$, A and Q are as described under formula I above, have been described previously or could be made by analogy of previous description by the person skilled in the art using literature and/or process described in this patent, for example in, WO 2013/018928.

Compounds of formula XVI, XVIa and XVII, wherein X, $X_1$, $R_1$, $R_2$, $R_3$, $R_6$, $R_7$, A and Q are as described under formula I above, have been described previously or could be made by analogy of previous description by the person skilled in the art using literature and/or process described in this patent, for example in, WO 2015/000715.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an) other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 96 below can be prepared according to the methods described above. The examples which follow are intended to illustrate the invention and show preferred compounds of formula I.

TABLE X

This table discloses the 27 substituent designations X.001 to X.027 for the formulae (Iaa), (Iab), (Iac) and (Iad) which are disclosed after Table X.

| Comp.No | Q |
| --- | --- |
| X.001 | phenyl |
| X.002 | 2-Cl-phenyl |
| X.003 | 3-Cl-phenyl |
| X.004 | 4-Cl-phenyl |
| X.005 | 2-$CF_3$-phenyl |
| X.006 | 3-$CF_3$-phenyl |
| X.007 | 4-$CF_3$-phenyl |
| X.008 | 5-Cl-pyridin-2-yl |
| X.009 | 3-Cl-pyridin-2-yl |
| X.010 | 3,5-di-Cl-pyridin-2-yl |
| X.011 | 5-F-pyridin-2-yl |
| X.012 | 3-F-pyridin-2-yl |
| X.013 | 3,5-di-F-pyridin-2-yl |
| X.014 | 3-F-5-$CF_3$-pyridin-2-yl |
| X.015 | 5-Cl-pyrimidin-2-yl |

TABLE X-continued

This table discloses the 27 substituent designations X.001 to X.027 for the formulae (Iaa), (Iab), (Iac) and (Iad) which are disclosed after Table X.

| Comp.No | Q |
|---|---|
| X.016 | 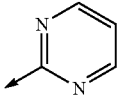 |
| X.017 | 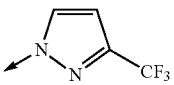 |
| X.018 | 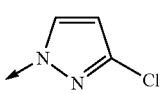 |
| X.019 | 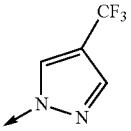 |
| X.020 | 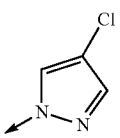 |
| X.021 |  |
| X.022 |  |
| X.023 |  |
| X.024 |  |
| X.025 | 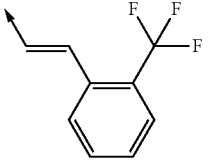 |
| X.026 | 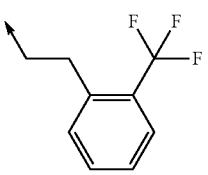 |

TABLE X-continued

This table discloses the 27 substituent designations X.001 to X.027 for the formulae (Iaa), (Iab), (Iac) and (Iad) which are disclosed after Table X.

| Comp.No | Q |
|---|---|
| X.027 | 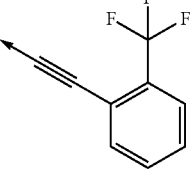 |

Table 1:
This table discloses the 27 compounds 1.001 to 1.027 of the formula (Iaa)

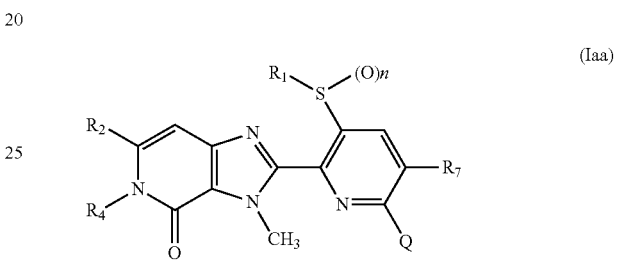

(Iaa)

wherein n is 0, and $R_2$ is $CF_3$, $R_4$ is methyl, $R_1$ is ethyl, $R_7$ is hydrogen and Q is as defined in lines X.001-X.027 in table X. For example, compound 1.004 has the following structure

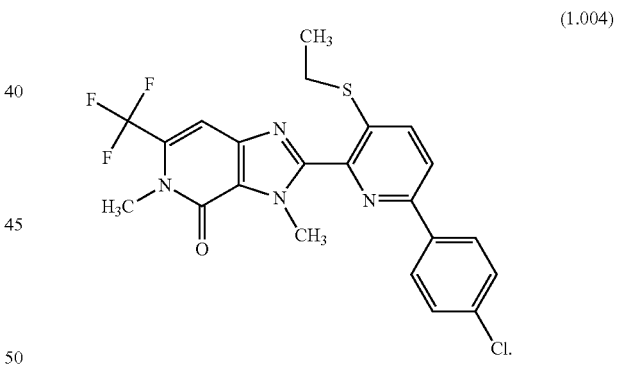

(1.004)

Table 2:
This table discloses the 27 compounds 2.001 to 2.024 of the formula (Iaa) wherein n is 2, and $R_2$ is $CF_3$, $R_1$ is ethyl, $R_4$ is methyl, $R_7$ is hydrogen and Q is as defined in lines X.001-X.027 in table X.

Table 3:
This table discloses the 27 compounds 3.001 to 3.027 of the formula (Iaa) wherein n is 0, and $R_2$ is $CF_2CF_3$, $R_1$ is ethyl, $R_4$ is methyl, $R_7$ is hydrogen and Q is as defined in lines X.001-X.027 in table X.

Table 4:
This table discloses the 27 compounds 4.001 to 4.027 of the formula (Iaa) wherein n is 2, and $R_2$ is $CF_2CF_3$, $R_1$ is ethyl, $R_4$ is methyl, $R_7$ is hydrogen and Q is as defined in lines X.001-X.027 in table X.

Table 5:

This table discloses the 27 compounds 5.001 to 5.027 of the formula (Iaa) wherein n is 0, and $R_2$ is $OCF_3$, $R_1$ is ethyl, $R_4$ is methyl, $R_7$ is hydrogen and Q is as defined in lines X.001-X.027 in table X.

Table 6:

This table discloses the 27 compounds 6.001 to 6.027 of the formula (Iaa) wherein n is 2, and $R_2$ is $OCF_3$, $R_1$ is ethyl, $R_4$ is methyl, $R_7$ is hydrogen and Q is as defined in lines X.001-X.027 in table X.

Table 7:

This table discloses the 27 compounds 7.001 to 7.027 of the formula (Iaa) wherein n is 0, and $R_2$ is $SCF_3$, $R_1$ is ethyl, $R_4$ is methyl, $R_7$ is hydrogen and Q is as defined in lines X.001-X.027 in table X.

Table 8:

This table discloses the 27 compounds 8.001 to 8.027 of the formula (Iaa) wherein n is 2, and $R_2$ is $SCF_3$, $R_1$ is ethyl, $R_4$ is methyl, $R_7$ is hydrogen and Q is as defined in lines X.001-X.027 in table X.

Table 9:

This table discloses the 27 compounds 9.001 to 9.027 of the formula (Iaa) wherein n is 0, and $R_2$ is $SOCF_3$, $R_1$ is ethyl, $R_4$ is methyl, $R_7$ is hydrogen and Q is as defined in lines X.001-X.027 in table X.

Table 10:

This table discloses the 27 compounds 10.001 to 10.027 of the formula (Iaa) wherein n is 2, and $R_2$ is $SOCF_3$, $R_1$ is ethyl, $R_4$ is methyl, $R_7$ is hydrogen and Q is as defined in lines X.001-X.027 in table X.

Table 11:

This table discloses the 27 compounds 11.001 to 11.027 of the formula (Iaa) wherein n is 0, and $R_2$ is $SO_2CF_3$, $R_1$ is ethyl, $R_4$ is methyl, $R_7$ is hydrogen and Q is as defined in lines X.001-X.027 in table X.

Table 12:

This table discloses the 27 compounds 12.001 to 12.027 of the formula (Iaa) wherein n is 2, and $R_2$ is $SO_2CF_3$, $R_1$ is ethyl, $R_4$ is methyl, $R_7$ is hydrogen and Q is as defined in lines X.001-X.027 in table X.

Table 13:

This table discloses the 27 compounds 13.001 to 13.027 of the formula (Iaa), wherein n is 0, and $R_2$ is $CF_3$, $R_4$ is ethyl, $R_1$ is ethyl, $R_7$ is hydrogen and Q is as defined in lines X.001-X.027 in table X.

Table 14:

This table discloses the 27 compounds 14.001 to 14.024 of the formula (Iaa) wherein n is 2, and $R_2$ is $CF_3$, $R_1$ is ethyl, $R_4$ is ethyl, $R_7$ is hydrogen and Q is as defined in lines X.001-X.027 in table X.

Table 15:

This table discloses the 27 compounds 15.001 to 15.027 of the formula (Iaa) wherein n is 0, and $R_2$ is $CF_2CF_3$, $R_1$ is ethyl, $R_4$ is ethyl, $R_7$ is hydrogen and Q is as defined in lines X.001-X.027 in table X.

Table 16:

This table discloses the 27 compounds 16.001 to 16.027 of the formula (Iaa) wherein n is 2, and $R_2$ is $CF_2CF_3$, $R_1$ is ethyl, $R_4$ is ethyl, $R_7$ is hydrogen and Q is as defined in lines X.001-X.027 in table X.

Table 17:

This table discloses the 27 compounds 17.001 to 17.027 of the formula (Iaa) wherein n is 0, and $R_2$ is $OCF_3$, $R_1$ is ethyl, $R_4$ is ethyl, $R_7$ is hydrogen and Q is as defined in lines X.001-X.027 in table X.

Table 18:

This table discloses the 27 compounds 18.001 to 18.027 of the formula (Iaa) wherein n is 2, and $R_2$ is $OCF_3$, $R_1$ is ethyl, $R_4$ is ethyl, $R_7$ is hydrogen and Q is as defined in lines X.001-X.027 in table X.

Table 19:

This table discloses the 27 compounds 19.001 to 19.027 of the formula (Iaa) wherein n is 0, and $R_2$ is $SCF_3$, $R_1$ is ethyl, $R_4$ is ethyl, $R_7$ is hydrogen and Q is as defined in lines X.001-X.027 in table X.

Table 20:

This table discloses the 27 compounds 20.001 to 20.027 of the formula (Iaa) wherein n is 2, and $R_2$ is $SCF_3$, $R_1$ is ethyl, $R_4$ is ethyl, $R_7$ is hydrogen and Q is as defined in lines X.001-X.027 in table X.

Table 21:

This table discloses the 27 compounds 21.001 to 21.027 of the formula (Iaa) wherein n is 0, and $R_2$ is $SOCF_3$, $R_1$ is ethyl, $R_4$ is ethyl, $R_7$ is hydrogen and Q is as defined in lines X.001-X.027 in table X.

Table 22:

This table discloses the 27 compounds 22.001 to 22.027 of the formula (Iaa) wherein n is 2, and $R_2$ is $SOCF_3$, $R_1$ is ethyl, $R_4$ is ethyl, $R_7$ is hydrogen and Q is as defined in lines X.001-X.027 in table X.

Table 23:

This table discloses the 27 compounds 23.001 to 23.027 of the formula (Iaa) wherein n is 0, and $R_2$ is $SO_2CF_3$, $R_1$ is ethyl, $R_4$ is ethyl, $R_7$ is hydrogen and Q is as defined in lines X.001-X.027 in table X.

Table 24:

This table discloses the 27 compounds 24.001 to 24.027 of the formula (Iaa) wherein n is 2, and $R_2$ is $SO_2CF_3$, $R_1$ is ethyl, $R_4$ is ethyl, $R_7$ is hydrogen and Q is as defined in lines X.001-X.027 in table X.

Table 25:

This table discloses the 27 compounds 25.001 to 25.027 of the formula (Iab)

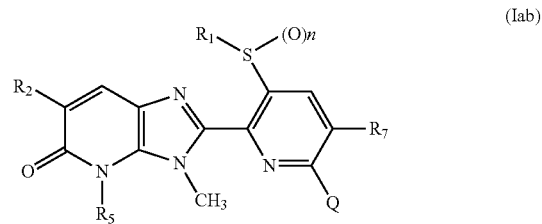

(Iab)

wherein n is 0, and $R_2$ is $CF_3$, $R_1$ is ethyl, $R_5$ is methyl, $R_7$ is hydrogen and Q is as defined in lines X.001-X.027 in table X. For example, compound 25.017 has the following structure (25.017)

[Chemical structure diagram]

Table 26:
This table discloses the 27 compounds 26.001 to 26.024 of the formula (Iab) wherein n is 2, and $R_2$ is $CF_3$, $R_1$ is ethyl, $R_5$ is methyl, $R_7$ is hydrogen and Q is as defined in lines X.001-X.027 in table X.

Table 27:
This table discloses the 27 compounds 27.001 to 27.027 of the formula (Iab) wherein n is 0, and $R_2$ is $CF_2CF_3$, $R_1$ is ethyl, $R_5$ is methyl, $R_7$ is hydrogen and Q is as defined in lines X.001-X.027 in table X.

Table 28:
This table discloses the 27 compounds 28.001 to 28.027 of the formula (Iab) wherein n is 2, and $R_2$ is $CF_2CF_3$, $R_1$ is ethyl, $R_5$ is methyl, $R_7$ is hydrogen and Q is as defined in lines X.001-X.027 in table X.

Table 29:
This table discloses the 27 compounds 29.001 to 29.027 of the formula (Iab) wherein n is 0, and $R_2$ is $OCF_3$, $R_1$ is ethyl, $R_5$ is methyl, $R_7$ is hydrogen and Q is as defined in lines X.001-X.027 in table X.

Table 30:
This table discloses the 27 compounds 30.001 to 30.027 of the formula (Iab) wherein n is 2, and $R_2$ is $OCF_3$, $R_1$ is ethyl, $R_5$ is methyl, $R_7$ is hydrogen and Q is as defined in lines X.001-X.027 in table X.

Table 31:
This table discloses the 27 compounds 31.001 to 31.027 of the formula (Iab) wherein n is 0, and $R_2$ is $SCF_3$, $R_1$ is ethyl, $R_5$ is methyl, $R_7$ is hydrogen and Q is as defined in lines X.001-X.027 in table X.

Table 32:
This table discloses the 27 compounds 32.001 to 32.027 of the formula (Iab) wherein n is 2, and $R_2$ is $SCF_3$, $R_1$ is ethyl, $R_5$ is methyl, $R_7$ is hydrogen and Q is as defined in lines X.001-X.027 in table X.

Table 33:
This table discloses the 27 compounds 33.001 to 33.027 of the formula (Iab) wherein n is 0, and $R_2$ is $SOCF_3$, $R_1$ is ethyl, $R_5$ is methyl, $R_7$ is hydrogen and Q is as defined in lines X.001-X.027 in table X.

Table 34:
This table discloses the 27 compounds 34.001 to 34.027 of the formula (Iab) wherein n is 2, and $R_2$ is $SOCF_3$, $R_1$ is ethyl, $R_5$ is methyl, $R_7$ is hydrogen and Q is as defined in lines X.001-X.027 in table X.

Table 35:
This table discloses the 27 compounds 35.001 to 35.027 of the formula (Iab) wherein n is 0, and $R_2$ is $SO_2CF_3$, $R_1$ is ethyl, $R_5$ is methyl, $R_7$ is hydrogen and Q is as defined in lines X.001-X.027 in table X.

Table 36:
This table discloses the 27 compounds 36.001 to 36.027 of the formula (Iab) wherein n is 2, and $R_2$ is $SO_2CF_3$, $R_1$ is ethyl, $R_5$ is methyl, $R_7$ is hydrogen and Q is as defined in lines X.001-X.027 in table X.

Table 37:
This table discloses the 27 compounds 37.001 to 37.027 of the formula (Iab) wherein n is 0, and $R_2$ is $CF_3$, $R_1$ is ethyl, $R_5$ is ethyl, $R_7$ is hydrogen and Q is as defined in lines X.001-X.027 in table X.

Table 38:
This table discloses the 27 compounds 38.001 to 38.024 of the formula (Iab) wherein n is 2, and $R_2$ is $CF_3$, $R_1$ is ethyl, $R_5$ is ethyl, $R_7$ is hydrogen and Q is as defined in lines X.001-X.027 in table X.

Table 39:
This table discloses the 27 compounds 39.001 to 39.027 of the formula (Iab) wherein n is 0, and $R_2$ is $CF_2CF_3$, $R_1$ is ethyl, $R_5$ is ethyl, $R_7$ is hydrogen and Q is as defined in lines X.001-X.027 in table X.

Table 40:
This table discloses the 27 compounds 40.001 to 40.027 of the formula (Iab) wherein n is 2, and $R_2$ is $CF_2CF_3$, $R_1$ is ethyl, $R_5$ is ethyl, $R_7$ is hydrogen and Q is as defined in lines X.001-X.027 in table X.

Table 41:
This table discloses the 27 compounds 41.001 to 41.027 of the formula (Iab) wherein n is 0, and $R_2$ is $OCF_3$, $R_1$ is ethyl, $R_5$ is ethyl, $R_7$ is hydrogen and Q is as defined in lines X.001-X.027 in table X.

Table 42:
This table discloses the 27 compounds 42.001 to 42.027 of the formula (Iab) wherein n is 2, and $R_2$ is $OCF_3$, $R_1$ is ethyl, $R_5$ is ethyl, $R_7$ is hydrogen and Q is as defined in lines X.001-X.027 in table X.

Table 43:
This table discloses the 27 compounds 43.001 to 43.027 of the formula (Iab) wherein n is 0, and $R_2$ is $SCF_3$, $R_1$ is ethyl, $R_5$ is ethyl, $R_7$ is hydrogen and Q is as defined in lines X.001-X.027 in table X.

Table 44:
This table discloses the 27 compounds 44.001 to 44.027 of the formula (Iab) wherein n is 2, and $R_2$ is $SCF_3$, $R_1$ is ethyl, $R_5$ is ethyl, $R_7$ is hydrogen and Q is as defined in lines X.001-X.027 in table X.

Table 45:
This table discloses the 27 compounds 45.001 to 45.027 of the formula (Iab) wherein n is 0, and $R_2$ is $SOCF_3$, $R_1$ is ethyl, $R_5$ is ethyl, $R_7$ is hydrogen and Q is as defined in lines X.001-X.027 in table X.

Table 46:
This table discloses the 27 compounds 46.001 to 46.027 of the formula (Iab) wherein n is 2, and $R_2$ is $SOCF_3$, $R_1$ is ethyl, $R_5$ is ethyl, $R_7$ is hydrogen and Q is as defined in lines X.001-X.027 in table X.

Table 47:
This table discloses the 27 compounds 47.001 to 47.027 of the formula (Iab) wherein n is 0, and $R_2$ is $SO_2CF_3$, $R_1$ is ethyl, $R_5$ is ethyl, $R_7$ is hydrogen and Q is as defined in lines X.001-X.027 in table X.

Table 48:
This table discloses the 27 compounds 48.001 to 48.027 of the formula (Iab) wherein n is 2, and $R_2$ is $SO_2CF_3$, $R_1$ is ethyl, $R_5$ is ethyl, $R_7$ is hydrogen and Q is as defined in lines X.001-X.027 in table X.

Table 49:
This table discloses the 27 compounds 49.001 to 49.027 of the formula (Iac)

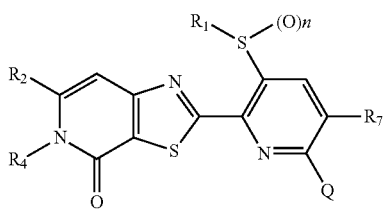

(Iac)

wherein n is 0, and $R_2$ is $CF_3$, $R_4$ is methyl, $R_1$ is ethyl, $R_7$ is hydrogen and Q is as defined in lines X.001-X.027 in table X. For example, compound 49.004 has the following structure

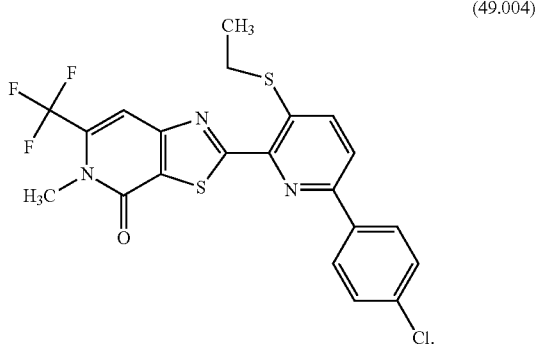 [SMILES: CCSc1ccc(-c2ccc(Cl)cc2)nc1-c1nc2cc(C(F)(F)F)n(C)c(=O)c2s1]

(49.004)

Table 50:
This table discloses the 27 compounds 50.001 to 50.024 of the formula (Iac) wherein n is 2, and $R_2$ is $CF_3$, $R_1$ is ethyl, $R_4$ is methyl, $R_7$ is hydrogen and Q is as defined in lines X.001-X.027 in table X.

Table 51:
This table discloses the 27 compounds 51.001 to 51.027 of the formula (Iac) wherein n is 0, and $R_2$ is $CF_2CF_3$, $R_1$ is ethyl, $R_4$ is methyl, $R_7$ is hydrogen and Q is as defined in lines X.001-X.027 in table X.

Table 52:
This table discloses the 27 compounds 52.001 to 52.027 of the formula (Iac) wherein n is 2, and $R_2$ is $CF_2CF_3$, $R_1$ is ethyl, $R_4$ is methyl, $R_7$ is hydrogen and Q is as defined in lines X.001-X.027 in table X.

Table 53:
This table discloses the 27 compounds 53.001 to 53.027 of the formula (Iac) wherein n is 0, and $R_2$ is $OCF_3$, $R_1$ is ethyl, $R_4$ is methyl, $R_7$ is hydrogen and Q is as defined in lines X.001-X.027 in table X.

Table 54:
This table discloses the 27 compounds 54.001 to 54.027 of the formula (Iac) wherein n is 2, and $R_2$ is $OCF_3$, $R_1$ is ethyl, $R_4$ is methyl, $R_7$ is hydrogen and Q is as defined in lines X.001-X.027 in table X.

Table 55:
This table discloses the 27 compounds 55.001 to 55.027 of the formula (Iac) wherein n is 0, and $R_2$ is $SCF_3$, $R_1$ is ethyl, $R_4$ is methyl, $R_7$ is hydrogen and Q is as defined in lines X.001-X.027 in table X.

Table 56:
This table discloses the 27 compounds 56.001 to 56.027 of the formula (Iac) wherein n is 2, and $R_2$ is $SCF_3$, $R_1$ is ethyl, $R_4$ is methyl, $R_7$ is hydrogen and Q is as defined in lines X.001-X.027 in table X.

Table 57:
This table discloses the 27 compounds 57.001 to 57.027 of the formula (Iac) wherein n is 0, and $R_2$ is $SOCF_3$, $R_1$ is ethyl, $R_4$ is methyl, $R_7$ is hydrogen and Q is as defined in lines X.001-X.027 in table X.

Table 58:
This table discloses the 27 compounds 58.001 to 58.027 of the formula (Iac) wherein n is 2, and $R_2$ is $SOCF_3$, $R_1$ is ethyl, $R_4$ is methyl, $R_7$ is hydrogen and Q is as defined in lines X.001-X.027 in table X.

Table 59:
This table discloses the 27 compounds 59.001 to 59.027 of the formula (Iac) wherein n is 0, and $R_2$ is $SO_2CF_3$, $R_1$ is ethyl, $R_4$ is methyl, $R_7$ is hydrogen and Q is as defined in lines X.001-X.027 in table X.

Table 60:
This table discloses the 27 compounds 60.001 to 60.027 of the formula (Iac) wherein n is 2, and $R_2$ is $SO_2CF_3$, $R_1$ is ethyl, $R_4$ is methyl, $R_7$ is hydrogen and Q is as defined in lines X.001-X.027 in table X.

Table 61:
This table discloses the 27 compounds 61.001 to 61.027 of the formula (Iac), wherein n is 0, and $R_2$ is $CF_3$, $R_4$ is ethyl, $R_1$ is ethyl, $R_7$ is hydrogen and Q is as defined in lines X.001-X.027 in table X.

Table 62:
This table discloses the 27 compounds 62.001 to 62.024 of the formula (Iac) wherein n is 2, and $R_2$ is $CF_3$, $R_1$ is ethyl, $R_4$ is ethyl, $R_7$ is hydrogen and Q is as defined in lines X.001-X.027 in table X.

Table 63:
This table discloses the 27 compounds 63.001 to 63.027 of the formula (Iac) wherein n is 0, and $R_2$ is $CF_2CF_3$, $R_1$ is ethyl, $R_4$ is ethyl, $R_7$ is hydrogen and Q is as defined in lines X.001-X.027 in table X.

Table 64:
This table discloses the 27 compounds 64.001 to 64.027 of the formula (Iac) wherein n is 2, and $R_2$ is $CF_2CF_3$, $R_1$ is ethyl, $R_4$ is ethyl, $R_7$ is hydrogen and Q is as defined in lines X.001-X.027 in table X.

Table 65:
This table discloses the 27 compounds 65.001 to 65.027 of the formula (Iac) wherein n is 0, and $R_2$ is $OCF_3$, $R_1$ is ethyl, $R_4$ is ethyl, $R_7$ is hydrogen and Q is as defined in lines X.001-X.027 in table X.

Table 66:
This table discloses the 27 compounds 66.001 to 66.027 of the formula (Iac) wherein n is 2, and $R_2$ is $OCF_3$, $R_1$ is ethyl, $R_4$ is ethyl, $R_7$ is hydrogen and Q is as defined in lines X.001-X.027 in table X.

Table 67:
This table discloses the 27 compounds 67.001 to 67.027 of the formula (Iac) wherein n is 0, and $R_2$ is $SCF_3$, $R_1$ is ethyl, $R_4$ is ethyl, $R_7$ is hydrogen and Q is as defined in lines X.001-X.027 in table X.

Table 68:
This table discloses the 27 compounds 68.001 to 68.027 of the formula (Iac) wherein n is 2, and $R_2$ is $SCF_3$, $R_1$ is ethyl, $R_4$ is ethyl, $R_7$ is hydrogen and Q is as defined in lines X.001-X.027 in table X.

Table 69:
This table discloses the 27 compounds 69.001 to 69.027 of the formula (Iac) wherein n is 0, and $R_2$ is $SOCF_3$, $R_1$ is ethyl, $R_4$ is ethyl, $R_7$ is hydrogen and Q is as defined in lines X.001-X.027 in table X.

Table 70:

This table discloses the 27 compounds 70.001 to 70.027 of the formula (Iac) wherein n is 2, and $R_2$ is $SOCF_3$, $R_1$ is ethyl, $R_4$ is ethyl, $R_7$ is hydrogen and Q is as defined in lines X.001-X.027 in table X.

Table 71:

This table discloses the 27 compounds 71.001 to 71.027 of the formula (Iac) wherein n is 0, and $R_2$ is $SO_2CF_3$, $R_1$ is ethyl, $R_4$ is ethyl, $R_7$ is hydrogen and Q is as defined in lines X.001-X.027 in table X.

Table 72:

This table discloses the 27 compounds 72.001 to 72.027 of the formula (Iac) wherein n is 2, and $R_2$ is $SO_2CF_3$, $R_1$ is ethyl, $R_4$ is ethyl, $R_7$ is hydrogen and Q is as defined in lines X.001-X.027 in table X.

Table 73:

This table discloses the 27 compounds 73.001 to 73.027 of the formula (Iad)

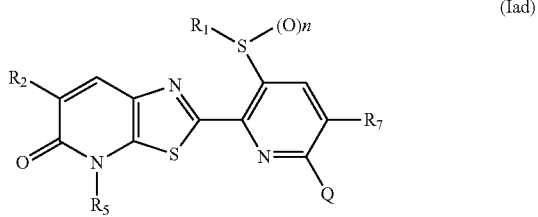

(Iad)

wherein n is 0, and $R_2$ is $CF_3$, $R_1$ is ethyl, $R_5$ is methyl, $R_7$ is hydrogen and Q is as defined in lines X.001-X.027 in table X. For example, compound 73.017 has the following structure:

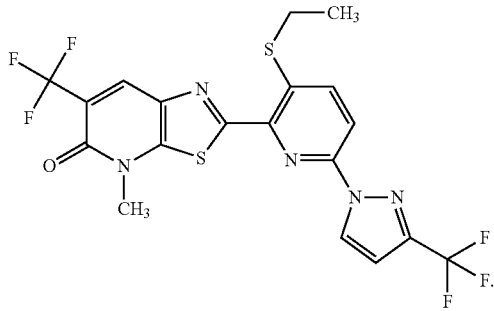

(73.017)

Table 74:

This table discloses the 27 compounds 74.001 to 74.024 of the formula (Iac) wherein n is 2, and $R_2$ is $CF_3$, $R_1$ is ethyl, $R_5$ is methyl, $R_7$ is hydrogen and Q is as defined in lines X.001-X.027 in table X.

Table 75:

This table discloses the 27 compounds 75.001 to 75.027 of the formula (Iac) wherein n is 0, and $R_2$ is $CF_2CF_3$, $R_1$ is ethyl, $R_5$ is methyl, $R_7$ is hydrogen and Q is as defined in lines X.001-X.027 in table X.

Table 76:

This table discloses the 27 compounds 76.001 to 76.027 of the formula (Iac) wherein n is 2, and $R_2$ is $CF_2CF_3$, $R_1$ is ethyl, $R_5$ is methyl, $R_7$ is hydrogen and Q is as defined in lines X.001-X.027 in table X.

Table 77:

This table discloses the 27 compounds 77.001 to 77.027 of the formula (Iac) wherein n is 0, and $R_2$ is $OCF_3$, $R_1$ is ethyl, $R_5$ is methyl, $R_7$ is hydrogen and Q is as defined in lines X.001-X.027 in table X.

Table 78:

This table discloses the 27 compounds 78.001 to 78.027 of the formula (Iac) wherein n is 2, and $R_2$ is $OCF_3$, $R_1$ is ethyl, $R_5$ is methyl, $R_7$ is hydrogen and Q is as defined in lines X.001-X.027 in table X.

Table 79:

This table discloses the 27 compounds 79.001 to 79.027 of the formula (Iac) wherein n is 0, and $R_2$ is $SCF_3$, $R_1$ is ethyl, $R_5$ is methyl, $R_7$ is hydrogen and Q is as defined in lines X.001-X.027 in table X.

Table 80:

This table discloses the 27 compounds 80.001 to 80.027 of the formula (Iac) wherein n is 2, and $R_2$ is $SCF_3$, $R_1$ is ethyl, $R_5$ is methyl, $R_7$ is hydrogen and Q is as defined in lines X.001-X.027 in table X.

Table 81:

This table discloses the 27 compounds 81.001 to 81.027 of the formula (Iac) wherein n is 0, and $R_2$ is $SOCF_3$, $R_1$ is ethyl, $R_5$ is methyl, $R_7$ is hydrogen and Q is as defined in lines X.001-X.027 in table X.

Table 82:

This table discloses the 27 compounds 82.001 to 82.027 of the formula (Iac) wherein n is 2, and $R_2$ is $SOCF_3$, $R_1$ is ethyl, $R_5$ is methyl, $R_7$ is hydrogen and Q is as defined in lines X.001-X.027 in table X.

Table 83:

This table discloses the 27 compounds 83.001 to 83.027 of the formula (Iac) wherein n is 0, and $R_2$ is $SO_2CF_3$, $R_1$ is ethyl, $R_5$ is methyl, $R_7$ is hydrogen and Q is as defined in lines X.001-X.027 in table X.

Table 84:

This table discloses the 27 compounds 84.001 to 84.027 of the formula (Iac) wherein n is 2, and $R_2$ is $SO_2CF_3$, $R_1$ is ethyl, $R_5$ is methyl, $R_7$ is hydrogen and Q is as defined in lines X.001-X.027 in table X.

Table 85:

This table discloses the 27 compounds 85.001 to 85.027 of the formula (Iac) wherein n is 0, and $R_2$ is $CF_3$, $R_1$ is ethyl, $R_5$ is ethyl, $R_7$ is hydrogen and Q is as defined in lines X.001-X.027 in table X.

Table 86:

This table discloses the 27 compounds 86.001 to 86.024 of the formula (Iac) wherein n is 2, and $R_2$ is $CF_3$, $R_1$ is ethyl, $R_5$ is ethyl, $R_7$ is hydrogen and Q is as defined in lines X.001-X.027 in table X.

Table 87:

This table discloses the 27 compounds 87.001 to 87.027 of the formula (Iac) wherein n is 0, and $R_2$ is $CF_2CF_3$, $R_1$ is ethyl, $R_5$ is ethyl, $R_7$ is hydrogen and Q is as defined in lines X.001-X.027 in table X.

Table 88:

This table discloses the 27 compounds 88.001 to 88.027 of the formula (Iac) wherein n is 2, and $R_2$ is $CF_2CF_3$, $R_1$ is ethyl, $R_5$ is ethyl, $R_7$ is hydrogen and Q is as defined in lines X.001-X.027 in table X.

Table 89:

This table discloses the 27 compounds 89.001 to 89.027 of the formula (Iac) wherein n is 0, and $R_2$ is $OCF_3$, $R_1$ is ethyl, $R_5$ is ethyl, $R_7$ is hydrogen and Q is as defined in lines X.001-X.027 in table X.

Table 90:

This table discloses the 27 compounds 90.001 to 90.027 of the formula (Iac) wherein n is 2, and $R_2$ is $OCF_3$, $R_1$ is ethyl, $R_5$ is ethyl, $R_7$ is hydrogen and Q is as defined in lines X.001-X.027 in table X.

Table 91:

This table discloses the 27 compounds 91.001 to 91.027 of the formula (Iac) wherein n is 0, and $R_2$ is $SCF_3$, $R_1$ is ethyl, $R_5$ is ethyl, $R_7$ is hydrogen and Q is as defined in lines X.001-X.027 in table X.

Table 92:

This table discloses the 27 compounds 92.001 to 92.027 of the formula (Iac) wherein n is 2, and $R_2$ is $SCF_3$, $R_1$ is ethyl, $R_5$ is ethyl, $R_7$ is hydrogen and Q is as defined in lines X.001-X.027 in table X.

Table 93:

This table discloses the 27 compounds 93.001 to 93.027 of the formula (Iac) wherein n is 0, and $R_2$ is $SOCF_3$, $R_1$ is ethyl, $R_5$ is ethyl, $R_7$ is hydrogen and Q is as defined in lines X.001-X.027 in table X.

Table 94:

This table discloses the 27 compounds 94.001 to 94.027 of the formula (Iac) wherein n is 2, and $R_2$ is $SOCF_3$, $R_1$ is ethyl, $R_5$ is ethyl, $R_7$ is hydrogen and Q is as defined in lines X.001-X.027 in table X.

Table 95:

This table discloses the 27 compounds 95.001 to 95.027 of the formula (Iac) wherein n is 0, and $R_2$ is $SO_2CF_3$, $R_1$ is ethyl, $R_5$ is ethyl, $R_7$ is hydrogen and Q is as defined in lines X.001-X.027 in table X.

Table 96:

This table discloses the 27 compounds 96.001 to 96.027 of the formula (Iac) wherein n is 2, and $R_2$ is $SO_2CF_3$, $R_1$ is ethyl, $R_5$ is ethyl, $R_7$ is hydrogen and Q is as defined in lines X.001-X.027 in table X.

The compounds of formula I according to the invention are preventively and/or curatively valuable active ingredients in the field of pest control, even at low rates of application, which have a very favourable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotino-phara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudotomoscelis seriatus*, *Psylla* spp., *Pulvinaria aethiopica*, *Quadraspidiotus* spp., *Quesada*

*gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculifera, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica,*

*Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca*(preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; Scutellonema species; Stubby root nematodes, *Trichodorus primitivus* and other *Trichodorus* species; Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp.,
*Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; *Deroceras* (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae Helicigona arbustorum); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins.

Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |
|  | *Oberea tripunctata* | Dogwood, Viburnum, Elm, Sourwood, Blueberry, Rhododendron, Azalea, Laurel, Poplar, Willow, Mulberry |
|  | *Oncideres cingulata* | Hickory, Pecan, Persimmon, Elm, Sourwood, Basswood, Honeylocust, Dogwood, *Eucalyptus*, Oak, Hackberry, Maple, Fruit trees |
|  | *Saperda calcarata* | Poplar |
|  | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
|  | *Dendroctonus frontalis* | Pine |
|  | *Dryocoetes betulae* | Birch, Sweetgum, Wild cherry, Beech, Pear |
|  | *Monarthrum fasciatum* | Oak, Maple, Birch, Chestnut, Sweetgum, Blackgum, Poplar, Hickory, Mimosa, Apple, Peach, Pine |
|  | *Phloeotribus liminaris* | Peach, Cherry, Plum, Black cherry, Elm, Mulberry, Mountain-ash |

TABLE B-continued

Examples of native woodborers of economic importance.

| Family | Species | Host or Crop Infested |
|---|---|---|
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as S. venatus verstitus and *S. parvulus*), and sod webworms (such as *Crambus* spp. and the tropical sod webworm, *Herpetogramma* phaeopteralis).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mpt." means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated.

LCMS Methods:

Method A:

Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+ 0.05% HCOOH, B=Acetonitrile+0.05% HCOOH, gradient: 10-100% B in 1.2 min; Flow (mL/min) 0.85

Example of the Synthesis of Intermediate Compounds

Intermediate 1: Synthesis of 4-amino-1-methyl-3-(methylamino)-6-(trifluoromethyl)pyridin-2-one

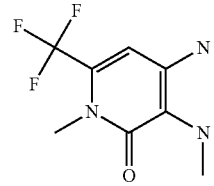

Step A: 1-methyl-3-(methylamino)-6-(trifluoromethyl)pyridin-2-one

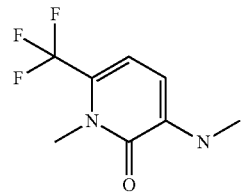

To a solution of 3-amino-1-methyl-6-(trifluoromethyl)pyridin-2-one (1.00 g, 5.20 mmol, Commercially available or synthesised as described for example in Synthesis 2005, No. 8, pp 1269-1278, Synthesis 2011, No. 7, pp 1149-1156) in 1,4-dioxane (62.5 mL, 726 mmol) and pyridine (1.49 mL, 18.2 mmol) under argon was added diacetoxycopper (2.39 g, 13.0 mmol). The mixture was stirred for 15 min before addition of methylboronic acid (0.803 g, 13.0 mmol). The resulting green/blue suspension was refluxed for 5 hours. After cooling, the solution was filtered through a Celite pad. The dark green solution was concentrated under vacuum and was subjected to column chromatography over silica gel, eluting with ethyl acetate/cyclohexane. The selected fractions were evaporated to yield the title compound (0.71 g).

$^1$H NMR (400 MHz, CDCl$_3$) δ ppm 7.27 (s, 1H); 6.72 (d, 1H); 6.04 (d, 2H), 5.46 (bs, 1H), 3.68 (s, 3H), 2.88 (d, 3H).

Step B: 1-methyl-3-(methylamino)-4-nitro-6-(trifluoromethyl)pyridin-2-one

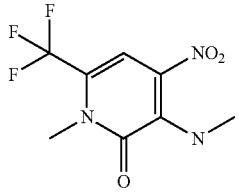 [SMILES: CNc1c([N+](=O)[O-])cc(C(F)(F)F)n(C)c1=O]

A solution of 1-methyl-3-(methylamino)-6-(trifluoromethyl)pyridin-2-one (4.00 g, 19.4 mmol) sulfuric acid (58.2 mL) was cooled with an ice bath at 0° C. Then, Ice (20.0 g) and nitric acid (1.88 g, 1.35 mL, 19.4 mmol) were added. After 15 min at 0-10° C., the brown thick solution was poured into iced water. The orange precipitate was filtrated off, rinsing with water and drying under vacuum to give an orange solid. The water phase was extracted 3 times with ethyl acetate and the orange solid, obtained before, was added to the combinated organic phase. The combinated organic phase was washed with a saturated solution of sodium hydrogenocarbonate, water and brine, dried over magnesium sulfate and concentrated under vacuum to give yield the title compound (4.0 g). The compound was used without extra purification for the next step. LC-MS (Method A): RT 0.91, 252 (M+H$^+$), 250 (M−H$^+$).

Step C: 4-amino-1-methyl-3-(methylamino)-6-(trifluoromethyl)pyridin-2-one

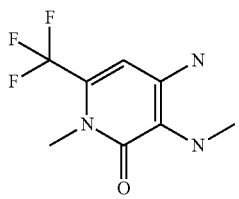

To a solution of 1-methyl-3-(methylamino)-4-nitro-6-(trifluoromethyl)pyridin-2-one (3.0 g, 11.9 mmol) in propan-2-ol (98.1 g, 125 mL, 1620 mmol) was added tin(II) chloride dihydrate (8.24 g, 43.0 mmol) followed by hydrogen chloride (10 mL, 120 mmol, 37%). The resulting solution was stirred at 70° C. for one hour, and, then allowed to cool down to ambient temperature. The reaction mixture was poured into water, and pH was adjusted to 10-12 with a concentrated solution of sodium hydroxide (30%). The aqueous phase was extracted three times with ethyl acetate. The organic phases were combined, dried over magnesium sulfate and concentrated under vacuum. The residue was subjected to column chromatography over silica gel, eluting with ethyl acetate/cyclohexane. The selected fractions were evaporated to yield the title compound (2.15 g). $^1$H NMR (400 MHz, CDCl$_3$) δ ppm 6.30 (s, 1H); 4.15 (bs, 2H), 3.8 (bs, 1H), 3.60 (s, 3H), 2.64 (s, 3H).

Intermediate 2: 4-amino-1-ethyl-3-(methylamino)-6-(trifluoromethyl)pyridin-2-one

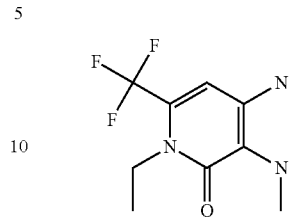

Step A: 1-ethyl-3-(methylamino)-6-(trifluoromethyl)pyridin-2-one

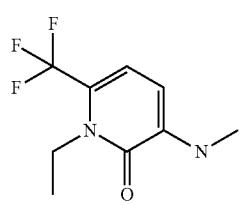

To a solution of 3-amino-1-ethyl-6-(trifluoromethyl)pyridin-2-one (5.00 g, 24.3 mmol, Commercially available or synthesised by analogy with literature, for example, Synthesis 2005, No. 8, pp 1269-1278 and Synthesis 2011, No. 7, pp 1149-1156) in acetonitrile (150 mL) was added formaldehyde (37 mass %) in aqueous solution (14.5 ml, 194 mmol) and acetic acid (6.96 ml, 121 mmol). The resulting suspension stirred for 1 hour, then sodium cyanoborohydride (6.42 g, 97.0 mmol) was added in 5 portions over 3 hours and the mixture was stirred overnight. The solution was diluted with water and extracted with ethyl acetate (3×). The combined organic layer was dried over Na$_2$SO$_4$, filtered, concentrated and purified by column chromatography using cyclohexane-ethyl acetate (100-200 silica gel) to give the desired compound as a white solid. $^1$H NMR (400 MHz, CDCl$_3$) δ ppm 6.70 (d, 1H), 6.04 (d, 1H), 5.44 (sb, 1H), 4.15 (q, 2H), 2.85 (s, 3H), 1.32 (t, 3H).

Step B: 1-ethyl-3-(methylamino)-4-nitro-6-(trifluoromethyl)pyridin-2-one

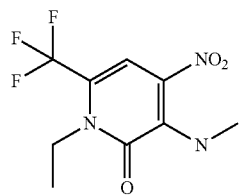 [SMILES: CCn1c(C(F)(F)F)cc([N+](=O)[O-])c(NC)c1=O]

The 1-ethyl-3-(methylamino)-4-nitro-6-(trifluoromethyl)pyridin-2-one was prepared as for Example 3, step B. LC-MS (Method A): RT 0.98, 266 (M+H$^+$), 264 (M−H$^+$).

Step C: 4-amino-1-ethyl-3-(methylamino)-6-(trifluoromethyl)pyridin-2-one

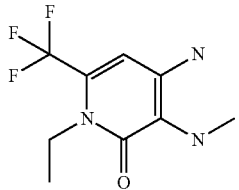 [SMILES: CCn1c(C(F)(F)F)cc(N)c(NC)c1=O]

The 4-amino-1-ethyl-3-(methylamino)-6-(trifluoromethyl)pyridin-2-one was prepared as for Example 3, step C. LC-MS (Method A): RT 0.47, 236 (M+H$^+$).

Intermediate 3: 3-ethylsulfanyl-6-[4-(trifluoromethyl)phenyl]pyridine-2-carboxylic acid

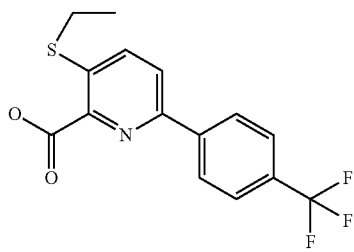 [SMILES: CCSc1ccc(-c2ccc(C(F)(F)F)cc2)nc1C(=O)O]

Step A: methyl 6-chloro-3-ethylsulfanyl-pyridine-2-carboxylate

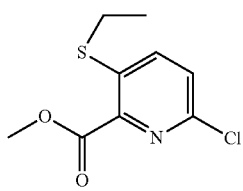

3,6-Dichloro-2-pyridinecarboxylic acid methyl ester (commercially available, 20 g, 97.073 mmol) was solved in tetrahydrofuran (200 mL) and 18-CROWN-6-ETHER (some crystals) was added. Sodium ethanethiolate (9.073 g, 97.073 mmol) was added in 3 portions at room temperature and reaction was stirred for 1 h at room temperature. The reaction mixture was poured on 100 ml saturated ammonium chloride aqueous solution, extracted with 2×100 ml ethyl acetate. The combined organic layers was washed with 2×50 ml saturated ammonium chloride aqueous solution, 3×100 ml water, dried over NaSO4, filtered and evaporated under vacuum. The crude was purified by combi flash chromatography with a column of 220 g and a gradient cyclohexane+ 0-10% ethyl acetate to give the title compound (14.5 g). Other products were obtained are substitution of the two chlorines and the mono substitution of the in position 6. $^1$H NMR (400 MHz, CDCl$_3$) δ ppm 1.42 (t, 3H), 2.96 (q, 2H), 4.02 (s, 3H), 7.45 (d, 1H), 7.70 (d, 1H)

Step B: Methyl 3-ethylsulfanyl-6-[4-(trifluoromethyl)phenyl]pyridine-2-carboxylate

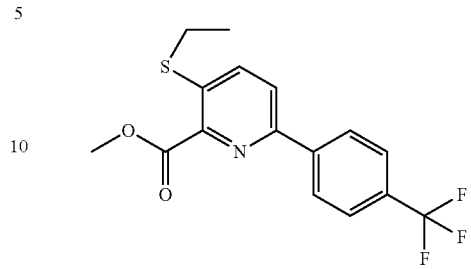

A solution of methyl 6-chloro-3-ethylsulfanyl-pyridine-2-carboxylate (0.3 g, 1.29 mmol) in 1,4-dioxane (7.5 mL) was treated with [4-(trifluoromethyl)phenyl]boronic acid (0.32 g, 1.68 mmol) and anhydrous K$_2$CO$_3$ (0.537 g, 3.88 mmol) and the mixture purged with argon for 10 min. To this mixture was added Tetrakis(triphenylphosphine)palladium (0) (0.149 g, 0.129 mmol) and the solution heated at 95° C. overnight. The reaction mixture was quenched with water at room temperature and ethyl acetate was added. The aqueous layer was extracted 3 times with ethyl acetate. The combined organic layer was washed with NaHCO$_3$ sat sol and brine, dried over sodium sulfate, filtered and evaporated under vacuum at 45° C. The crude product was dissolved in dichloromethane and adsorbed on TEFLON BULK SORBENTS. The crude was purified by Combi flash chromatography with a column of 24 g and a gradient cyclohexane+ 0-50% ethyl acetate to give the title compound (280 mg) as a white solid and use, without extra purification in the next step.

Step C: 3-ethylsulfanyl-6-[4-(trifluoromethyl)phenyl]pyridine-2-carboxylic acid

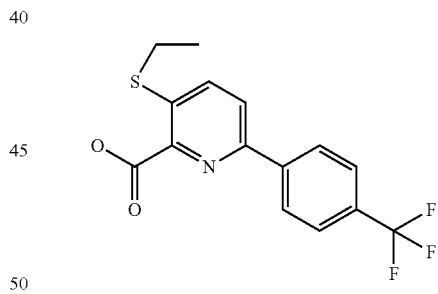

Methyl 3-ethylsulfanyl-6-[4-(trifluoromethyl)phenyl]pyridine-2-carboxylate (870 mg, 2.548 mmol) was dissolved in tetrahydrofuran (10.2 mL) and water (2.55 mL) and treated with lithium hydroxide hydrate (61.03 mg, 2.548 mmol) at ambient temperature overnight. LCMS analysis after overnight stirring showed that the reaction was not finish and) 1 eq of lithium hydroxide hydrate was added, after 1 h at RT the reaction is complete. The reaction mixture was diluted with ethyl acetate and water. The organic phase was remove and the aqueous phase was acidified with HCl concentrated then the acid precipitate and the solid was filtered to give the title compound (0.55 g) as solid that was used in the next step without further purification. $^1$H NMR (400 MHz, DMSO-d6) δ ppm 1.30 (t, 3H), 3.07 (q, 2H), 7.88 (d, 2H), 8.05 (d, 1H), 8.22 (d, 1H), 8.39 (d, 2H), 13.33 (sb, 1H)

Intermediate 4: 3-ethylsulfonyl-6-[3-(trifluoromethyl)pyrazol-1-yl]pyridine-2-carboxylic acid

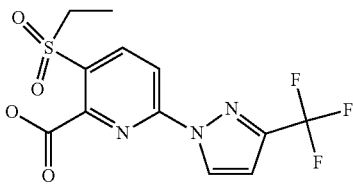 [SMILES: CCS(=O)(=O)c1ccc(-n2ccc(C(F)(F)F)n2)nc1C(=O)O]

Step A: methyl 6-chloro-3-ethylsulfonyl-pyridine-2-carboxylate

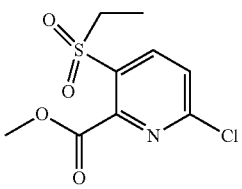 [SMILES: CCS(=O)(=O)c1ccc(Cl)nc1C(=O)OC]

In a three neck flask under argon, methyl 6-chloro-3-ethylsulfanyl-pyridine-2-carboxylate (Intermediate 3, step A, 4 g, 17.264 mmol) was dissolved in dichloromethane (80 mL) and cooled down to 0° C. Then 3-chloroperoxybenzoic acid (8.9374 g, 36.254 mmol) was added and reaction was stirred 30' at 0° C. then warmed up at room temperature and stirred one night. The reaction mixture was quenched with NaOH 1 M (50 ml) and sodium thiosulfate sole (20 ml). The aqueous layer was extracted 3 times with dichloromethane. The combined organic layer was washed with NaOH 1M (2×), brine, dried over Na2S04, filtered and evaporated under vacuum to give the title compound (4.4 g). $^1$H NMR (400 MHz, CDCl$_3$) δ ppm 1.34 (t, 3H), 3.52 (q, 2H), 4.05 (s, CH3), 7.62 (d, 1H), 8.30 (d, 1H).

Step B: methyl 3-ethylsulfonyl-6-[3-(trifluoromethyl)pyrazol-1-yl]pyridine-2-carboxylate

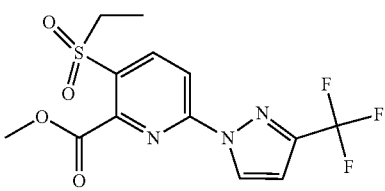 [SMILES: CCS(=O)(=O)c1ccc(-n2ccc(C(F)(F)F)n2)nc1C(=O)OC]

Methyl-6-chloro-3-ethylsulfonyl-pyridine-2-carboxylate (0.102 g, 0.387 mmol), 3-(trifluoromethyl)-1H-pyrazole (0.058 g, 0.426 mmol) and dipotassium carbonate (0.107 g, 0.77 mmol) were dissolved in Dimethylformamide (1.9 g, 2.04 mL, 26 mmol). The resulting mixture was stirred 1 h at 50° C. The reaction mixture was quenched with water and the aqueous layer was extracted 3 times with ter-butylmethylester. The combined organic layer was washed with water and brine, dried over sodium sulfate, filtered and evaporated under vacuum at 45° C. to give the title compound (0.137 mg) as pure product. $^1$H NMR (400 MHz, CDCl$_3$) δ ppm 1.36 (t, 3H), 3.50 (q, 2H), 4.06 (s, CH3), 6.78 (s, 1H), 8.30 (d, 1H), 8.48 (d, 1H), 8.68 (s, 1H).

Step C: 3-ethylsulfonyl-6-[3-(trifluoromethyl)pyrazol-1-yl]pyridine-2-carboxylic acid

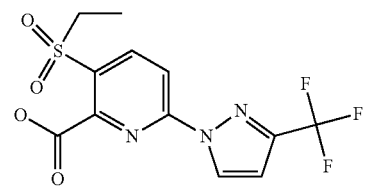 [SMILES: CCS(=O)(=O)c1ccc(-n2ccc(C(F)(F)F)n2)nc1C(=O)O]

Methyl 3-ethylsulfonyl-6-[3-(trifluoromethyl)pyrazol-1-yl]pyridine-2-carboxylate (3.8 g, 10 mmol) was dissolved in tetrahydrofuran (57 mL) and water (19 mL) and treated with lithium hydroxide hydrate (0.46 g, 11 mmol) at ambient temperature for 5 hours. THF was evaporated and 10 mL of HCl 1 N was added (pH 1) to the residue. Then aqueous layer was extracted 3 times with ethyl acetate. The organic layer was dried over Na2SO4, filtered and evaporated under vacuum to give the title compound (3.5 g) as solid that was used in the next step without further purification. $^1$H NMR (400 MHz, DMSO-d6) δ ppm 1.22 (t, 3H), 3.58 (q, 2H), 7.18 (s, 1H), 8.28 (d, 1H), 8.56 (d, 1H), 8.92 (s, 1H), 14.55 (sb, 1H).

Intermediate 5: 4-amino-1-cyclopropyl-3-(methylamino)-6-(trifluoromethyl)pyridin-2-one

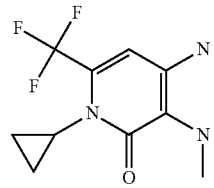 [SMILES: CNc1c(N)cc(C(F)(F)F)n(C2CC2)c1=O]

Step A: 1-cyclopropyl-3-(amino)-6-(trifluoromethyl)pyridin-2-one

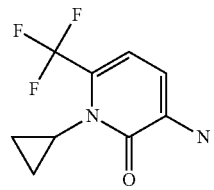 [SMILES: Nc1ccc(C(F)(F)F)n(C2CC2)c1=O]

A sealed bomb was charged with N-[2-oxo-6-(trifluoromethyl)pyran-3-yl]benzamide (commercially available, CAS Registry Number 312615-59-1, 30 g, 105.9 mmol), tetrahydrofuran (132.4 mL, 1620 mmol) and cyclopropylamine (8.24 mL, 116.5 mmol). The mixture was stirred for overnight at 70° C. The sealed vial was cooled and the reaction mixture was dissolved with water and ethyl acetate (250 ml/250 ml). The aqueous phase was extracted with ethyl acetate (3×) and the combined organic layer was dried over sodium sulfate, filtered, concentrated under vaccum. The residue was purified by column chromatography using cyclohexane-ethyl acetate to give the starting material and 23 g of N-[1-cyclopropyl-2-hydroxy-6-oxo-2-(trifluoromethyl)-3H-pyridin-5-yl]benzamide. The N-[1-cyclopropyl-2-hydroxy-6-oxo-2-(trifluoromethyl)-3H-pyridin-5-yl]benzamide was dissolved in hydrogen chloride (563 g, 473.1 mL, 5710 mmol) and the mixture was stirred at 100° C. for Over Night. The precipitate of Benzoic acid was filtered off and the filtrate was basified to pH 7-8 with a solution of sodium hydroxyl conc. Then the water phase was extracted (3x) with AcOEt and the combined organic layers were dried over sodium sulfate, filtered and concentrated under vacuum. The residue was purified by column chromatography using cyclohexane-ethyl acetate to give 12 g of 1-cyclopropyl-3-(amino)-6-(trifluoromethyl)pyridin-2-one. LC-MS (Method A): RT 0.79, 219 (M$^+$H$^+$). $^1$H NMR (400 MHz, CDCl$_3$) δ ppm 6.59 (d, 1H), 6.33 (d, 1H), 4.60 (sb, 2H), 3.07 (m, 1H), 1.24 (m, 2H), 1.02 (m, 2H).

Step B: 1-cyclopropyl-3-(methylamino)-6-(trifluoromethyl)pyridin-2-one

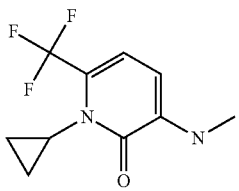 [SMILES: CNc1ccc(C(F)(F)F)n(C2CC2)c1=O]

The 1-cyclopropyl-3-(methylamino)-4-nitro-6-(trifluoromethyl)pyridin-2-one was prepared as for Example 14, step A. LC-MS (Method A): RT 0.93, 233 (M+H$^+$).

Step C: 1-cyclopropyl-3-(methylamino)-4-nitro-6-(trifluoromethyl)pyridin-2-one

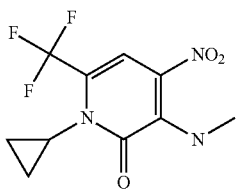 [SMILES: CNc1c([N+](=O)[O-])cc(C(F)(F)F)n(C2CC2)c1=O]

The 1-cyclopropyl-3-(methylamino)-4-nitro-6-(trifluoromethyl)pyridin-2-one was prepared as for Example 12, step C. LC-MS (Method A): RT 0.98, 278 (M+H$^+$).

Step D: 4-amino-1-cyclopropyl-3-(methylamino)-6-(trifluoromethyl)pyridin-2-one

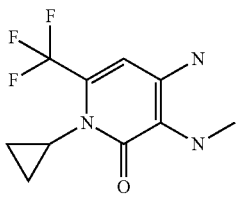 [SMILES: CNc1c(N)cc(C(F)(F)F)n(C2CC2)c1=O]

The 4-amino-1-cyclopropyl-3-(methylamino)-6-(trifluoromethyl)pyridin-2-one was prepared as for Example 12, step D. LC-MS (Method A): RT 0.52, 247 (M$^+$H$^+$). Alternatively, the 4-amino-1-cyclopropyl-3-(methylamino)-6-(trifluoromethyl)pyridin-2-one could be prepared via hydrogenation in presence of Pd/C in ethanol using classical reaction. 1H NMR (400 MHz, CDCl3) δ ppm 6.28 (s, 1H), 4.08 (sb, 2H), 3.81 (sb, 1H), 2.97 (m, 1H), 2.63 (s, 3H), 1.18 (m, 2H), 0.98 (m, 2H).

Intermediate 6:
6-chloro-3-ethylsulfanyl-pyridine-2-carboxylic acid

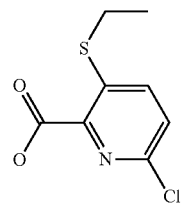

A solution of methyl 6-chloro-3-ethylsulfanyl-pyridine-2-carboxylate (3.900 g, 14.12 mmol) (preparation described here above) in a mixture of methyl alcohol (75 ml) and water (20 ml) stirred at 20° C. was treated with 2N aqueous sodium hydroxide solution (7.04 ml, 1.05 equiv.). The mixture was stirred for two hours, and then most of the alcohol was eliminated under reduced pressure. The residue was then treated with 2N aqueous hydrochloric acid solution and the resulting precipitate was filtered off, washed with water and dried under vacuum. The title compound was obtained as a colorless solid. $^1$H NMR (400 MHz, DMSO) δ ppm 1.23 (d, 3H) 2.99 (q, 2H) 7.64 (d, 1H) 7.95 (d, 1H).

Intermediate 7: 2-(6-chloro-3-ethylsulfonyl-2-pyridyl)-5-ethyl-3-methyl-6-(trifluoromethyl)imidazo[4,5-c]pyridin-4-one

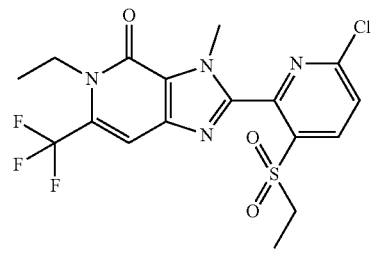 [SMILES: CCn1c(C(F)(F)F)cc2nc(-c3nc(Cl)ccc3S(=O)(=O)CC)n(C)c2c1=O]

Step A: 6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide

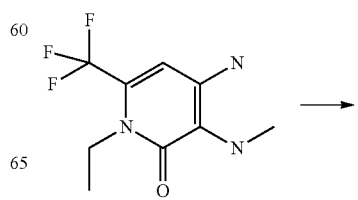

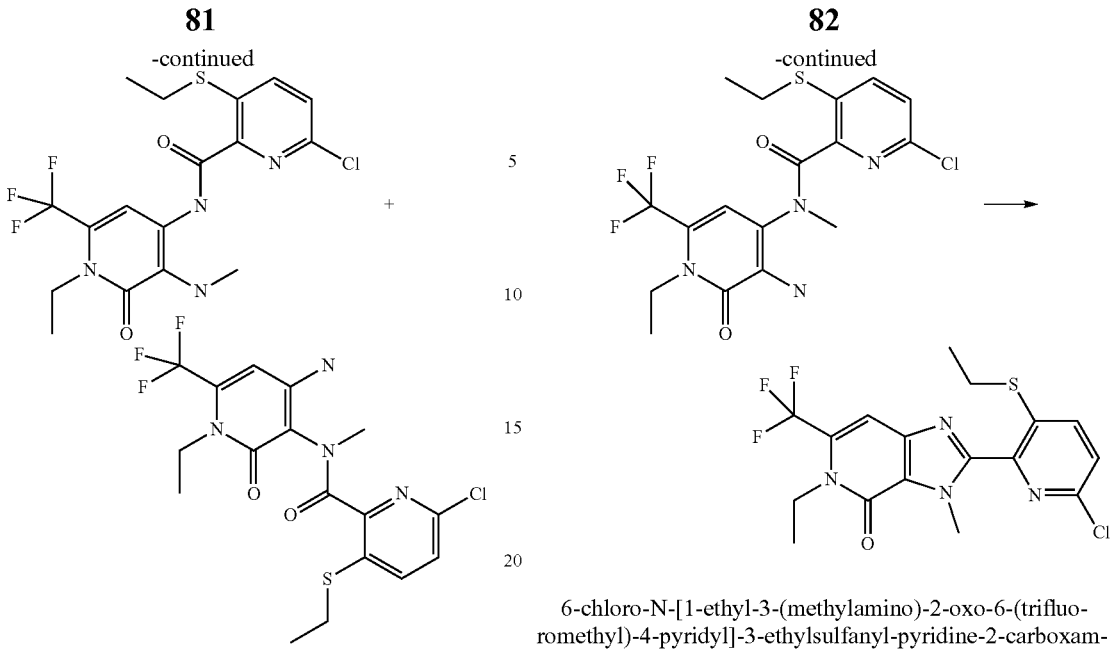

Under Argon, 6-chloro-3-ethylsulfanyl-pyridine-2-carboxylic acid (as prepared in Example 15, Step A, B, C) (4.2 g, 19 mmol) is dissolved in dichloromethane (39 mL) with oxalyl dichloride (5.0 g, 39 mmol) and N,N-dimethylformamide (1 drop). The mixture was stirred for 30 min at room temperature then at reflux for 30 min. Then the solvent was removed and dried by vacuum, 6-chloro-3-ethylsulfanyl-pyridine-2-carbonyl chloride (4.2 g, 18 mmol) was diluted with 5 ml of tetrahydrofuran and to this a solution of 4-amino-1-ethyl-3-(methylamino)-6-(trifluoromethyl)pyridin-2-one (4.6 g, 20 mmol) in tetrahydrofuran (36 mL) and pyridine (4.2 g, 4.3 mL) was added under Ar.

The mixture was stirred at reflux for 3 hours, then the brown suspension was poured into NaHCO$_3$, extracted with ethyl acetate, organic phase was washed with a solution of hydrogen chloride (1 N), brine, dried over MgSO$_4$ and concentrated under vacuum to give a mixture of 6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide (7 g, 90%) as a brown solid.

$^1$H NMR (400 MHz, CDCl$_3$) δ=7.76 (d, J=8.4 Hz, 1H), 7.57 (d, J=8.3 Hz, 3H), 7.34 (d, J=8.3 Hz, 1H), 7.14 (d, J=8.4 Hz, 3H), 6.32 (br. s., 1H), 6.14 (br. s., 3H), 5.00-4.74 (m, 8H), 4.09-4.00 (m, 4H), 3.89-3.76 (m, 3H), 3.26 (s, 9H), 3.12-3.07 (m, 4H), 3.03-2.88 (m, 9H), 1.37-1.28 (m, 17H), 1.13 (t, J=6.9 Hz, 10H).

Step E: 2-(6-chloro-3-ethylsulfanyl-2-pyridyl)-5-ethyl-3-methyl-6-(trifluoromethyl)imidazo[4,5-c]pyridin-4-one

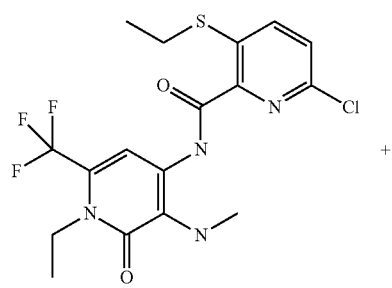

6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide (7.0 g, 16 mmol) were dissolved in acetic acid (50 mL) and refluxed for 24 hours. Reaction mass was concentrated under reduced pressure to remove all acetic acid, this was dissolved in dichloromethane and purified by combiflash to give 2-(6-chloro-3-ethylsulfanyl-2-pyridyl)-5-ethyl-3-methyl-6-(trifluoromethyl)imidazo[4,5-c]pyridin-4-one (5 g, 75%) as an slightly yellow solid. $^1$H NMR (400 MHz, CDCl$_3$) δ=7.72 (d, 1H), 7.40 (d, 1H), 7.34-7.29 (m, 1H), 4.29-4.21 (m, 5H), 2.93 (q, 2H), 1.42-1.28 (m, 6H).

Step F: 2-(6-chloro-3-ethylsulfonyl-2-pyridyl)-5-ethyl-3-methyl-6-(trifluoromethyl)imidazo[4,5-c]pyridin-4-one

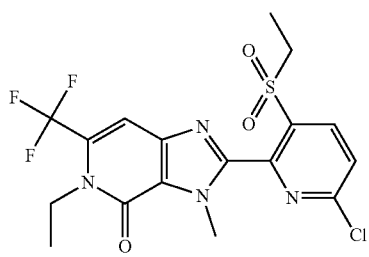 [SMILES: CCn1c(C(F)(F)F)cc2nc(-c3nc(Cl)ccc3S(=O)(=O)CC)n(C)c2c1=O]

To a solution of 2-(6-chloro-3-ethylsulfanyl-2-pyridyl)-5-ethyl-3-methyl-6-(trifluoromethyl)imidazo[4,5-c]pyridin-4-one (4.6 g, 11 mmol) in dichloromethane (50 mL) was added 3-chlorobenzenecarboperoxoic acid (5.2 g, 23 mmol). The mixture was allowed to stand over night at room temperature. It was quenched with a solution of sodium thiosulfate (100 ml) and reaction mass was diluted with 1N NaOH (100 ml), extracted with dichloromethane (3*50 ml). Combined organic layer was dried over sodium sulfate, filtered and concentrated under reduced pressure to give 2-(6-chloro-3-ethylsulfonyl-2-pyridyl)-5-ethyl-3-methyl-6-(trifluoromethyl)imidazo[4,5-c]pyridin-4-one (4.6 g, 93%).

$^1$H NMR (400 MHz, CDCl$_3$) δ=8.49-8.41 (m, 1H), 7.76-7.65 (m, 1H), 7.24-7.18 (m, 1H), 4.25 (q, 2H), 4.13 (s, 3H), 3.84-3.73 (m, 2H), 1.45-1.31 (m, 6H).

Intermediate 8: 2-(6-chloro-3-ethylsulfonyl-2-pyridyl)-3,5-dimethyl-6-(trifluoromethyl)imidazo[4,5-c]pyridin-4-one

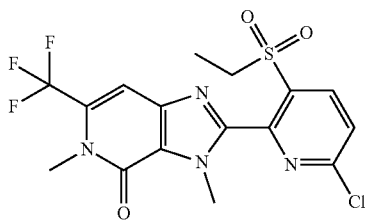 [SMILES: CCS(=O)(=O)c1ccc(Cl)nc1-c1nc2cc(C(F)(F)F)n(C)c(=O)c2n1C]

Prepared from intermediate 2-(6-chloro-3-ethylsulfonyl-2-pyridyl)-3,5-dimethyl-6-(trifluoromethyl)imidazo[4,5-c]pyridin-4-one, using a similar protocol as described for Intermediate 7 using the appropriate intermediates.

2-(6-chloro-3-ethylsulfanyl-2-pyridyl)-3,5-dimethyl-6-(trifluoromethyl)imidazo[4,5-c]pyridin-4-one. $^1$H NMR (400 MHz, CDCl$_3$) δ ppm 1.32 (t, 3H), 2.92 (q, 2H), 3.73 (d, 3H), 4.23 (s, 3H), 7.31 (s, 1H), 7.40 (d, 1H), 7.72 (d, 1H).

2-(6-chloro-3-ethylsulfonyl-2-pyridyl)-3,5-dimethyl-6-(trifluoromethyl)imidazo[4,5-c]pyridin-4-one: $^1$H NMR (400 MHz, CDCl$_3$) δ ppm 1.34 (t, 3H), 3.75 (s, 3H), 3.78 (q, 2H), 4.12 (s, 3H), 7.20 (s, 1H), 7.70 (d, 1H), 8.44 (d, 1H).

Intermediate 9: 2-(6-chloro-3-ethylsulfonyl-2-pyridyl)-5-cyclopropyl-3-methyl-6-(trifluoromethyl)imidazo[4,5-c]pyridin-4-one

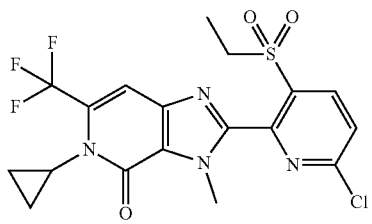 [SMILES: CCS(=O)(=O)c1ccc(Cl)nc1-c1nc2cc(C(F)(F)F)n(C3CC3)c(=O)c2n1C]

2-(6-chloro-3-ethylsulfonyl-2-pyridyl)-5-cyclopropyl-3-methyl-6-(trifluoromethyl)imidazo[4,5-c]pyridin-4-one was prepared as described for Intermediate 7 using the appropriate intermediates.

2-(6-chloro-3-ethylsulfanyl-2-pyridyl)-5-cyclopropyl-3-methyl-6-(trifluoromethyl)imidazo[4,5-c]pyridin-4-one: $^1$H NMR (400 MHz, DMSO) δ ppm 8.08 (d, 1H), 7.70 (d, 1H), 7.34 (s, 1H), 4.02 (s, 3H), 3.08 (m, 1H), 3.04 (q, 2H), 1.18 (m, 5H), 0.96 (m, 2H).

2-(6-chloro-3-ethylsulfonyl-2-pyridyl)-5-cyclopropyl-3-methyl-6-(trifluoromethyl)imidazo[4,5-c]pyridin-4-one: $^1$H NMR (400 MHz, DMSO) δ ppm 8.52 (d, 1H), 8.08 (d, 1H), 7.38 (s, 1H), 3.91 (s, 3H), 3.74 (q, 2H), 3.08 (m, 1H), 1.18 (m, 5H), 0.98 (m, 2H).

Intermediate 10: 3-ethylsulfonyl-6-(1,2,4-triazol-1-yl)pyridine-2-carboxylic acid

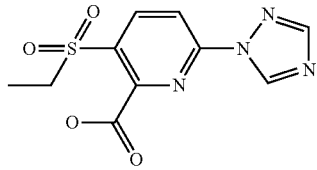 [SMILES: CCS(=O)(=O)c1ccc(-n2cncn2)nc1C(=O)O]

Step A: methyl 3-ethylsulfonyl-6-(1,2,4-triazol-1-yl)pyridine-2-carboxylate

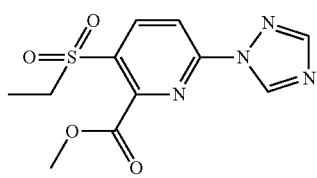 [SMILES: CCS(=O)(=O)c1ccc(-n2cncn2)nc1C(=O)OC]

A 20 mL flask, flushed with argon, was added 4H-1,2,4-triazole (0.962 g, 13.7 mmol) and NMP (10 mL). Then, sodium hydride (60 mass %) in paraffin oil (0.455 g, 11.4 mmol) was added and after 30 min methyl 6-chloro-3-ethylsulfonyl-pyridine-2-carboxylate (1.00 g, 3.79 mmol) was added. The reaction mixture was stirred for 10 minutes at room temperature. The mixture was poured gently in cold water (200 mL) and the white solid formed was filtered. The solid was used, after be dried under vacuum, without any extra purification—0.526 g, 46.8% Yield. $^1$H NMR (400 MHz, CDCl$_3$) δ ppm 9.24 (s, 1H), 8.50 (d, 1H), 8.18 (m, 2H), 4.07 (s, 3H), 3.50 (q, 2H), 1.36 (t, 3H).

Step B: 3-ethylsulfonyl-6-(1,2,4-triazol-1-yl)pyridine-2-carboxylic acid

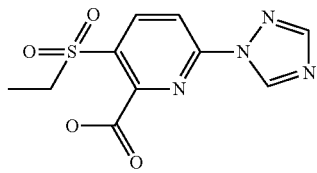

The 3-ethylsulfonyl-6-(1,2,4-triazol-1-yl)pyridine-2-carboxylic acid was obtained by hydrolysis of the methyl ester via a protocol identical that Step C-Intermediate 4. LC-MS (Method A) RT: 0.26 (283, M+H$^+$).

Example of the Preparation of Compounds of Formula I

Example E1: Preparation of 5-ethyl-2-[3-ethylsulfanyl-6-[4-(trifluoromethyl)phenyl]-2-pyridyl]-3-methyl-6-(trifluoromethyl)imidazo[4,5-c]pyridin-4-one (Compound 13.007, Example P1, Table P) and 5-ethyl-2-[3-ethylsulfonyl-6-[4-(trifluoromethyl)phenyl]-2-pyridyl]-3-methyl-6-(trifluoromethyl)imidazo[4,5-c]pyridin-4-one (Compound 14.007, Example P2, Table P)

Step A: N-[1-ethyl-3-(methylamino)-2-oxo-6-(trifluoromethyl)-4-pyridyl]-3-ethylsulfanyl-6-[4-(trifluoromethyl)phenyl]pyridine-2-carboxamide and N-[4-amino-1-ethyl-2-oxo-6-(trifluoromethyl)-3-pyridyl]-3-ethylsulfanyl-N-methyl-6-[4-(trifluoromethyl)phenyl]pyridine-2-carboxamide

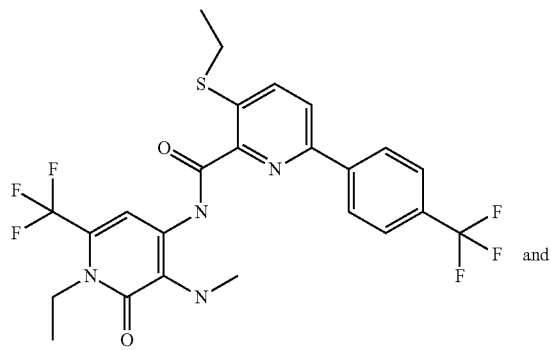

and

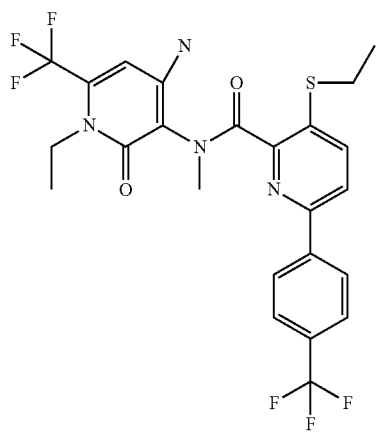

To a suspension of 3-ethylsulfanyl-6-[4-(trifluoromethyl)phenyl]pyridine-2-carboxylic acid (153 mg, 0.467 mmol) in dichloromethane (0.9 ml) was added one drop of N,N-dimethylformamide, followed by oxalyl chloride (121 mg, 0.0831 mL, 0.934 mmol). After the end of gas evolution, the reaction mixture was stirred 30 minutes at reflux. The solvent was evaporated under reduced pressure at a bath temperature of 60° C. The residue was redissolved 0.5 ml of THF.

To a solution of 4-amino-1-ethyl-3-(methylamino)-6-(trifluoromethyl)pyridin-2-one (prepared in intermediate preparation 2: step C, 100 mg, 0.42515 mmol) in THF (0.85 ml) was added pyridine (100.89 mg, 0.10 mL, 1.2755 mmol). The solution was cooled at 0° C. and the previous acyl chloride solution was slowly added. The resulting mixture was stirred 3 hours at reflux. The solution was neutralized by addition of a saturated aqueous solution of sodium bicarbonate and the product was extracted twice with ethyl acetate. The organic solution was dried over sodium sulfate and evaporated under reduced pressure to yield the crude product. A mixture of N-[1-ethyl-3-(methylamino)-2-oxo-6-(trifluoromethyl)-4-pyridyl]-3-ethylsulfanyl-6-[4-(trifluoromethyl)phenyl]pyridine-2-carboxamide and N-[4-amino-1-ethyl-2-oxo-6-(trifluoromethyl)-3-pyridyl]-3-ethylsulfanyl-N-methyl-6-[4-(trifluoromethyl)phenyl]pyridine-2-carboxamide was obtained and used without extra purification for the next step. LC-MS (Method A): RT 1.11, 545 (M+H$^+$), 543 (M−H$^+$).

Step B: 5-ethyl-2-[3-ethylsulfanyl-6-[4-(trifluoromethyl)phenyl]-2-pyridyl]-3-methyl-6-(trifluoromethyl)imidazo[4,5-c]pyridin-4-one (compound 13.007, example P1, table P)

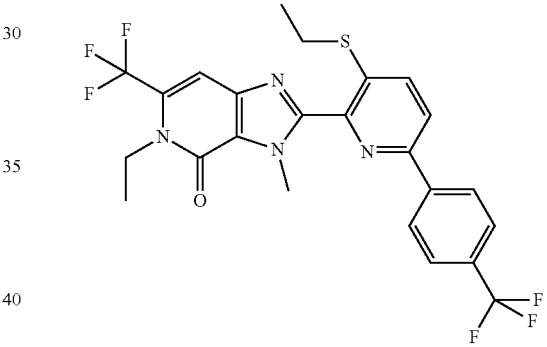

(Compound 13.007, example P1, table P)

A mixture of N-[1-ethyl-3-(methylamino)-2-oxo-6-(trifluoromethyl)-4-pyridyl]-3-ethylsulfanyl-6-[4-(trifluoromethyl)phenyl]pyridine-2-carboxamide and N-[4-amino-1-ethyl-2-oxo-6-(trifluoromethyl)-3-pyridyl]-3-ethylsulfanyl-N-methyl-6-[4-(trifluoromethyl)phenyl]pyridine-2-carboxamide (0.175 g, 0.3214 mmol, the product of step C) in 1.6 ml of acetic acid was heated at 150° C. for 30 minutes under MW. The dark brown solution was poured into a mixture of ethyl acetate and water. The phases were separated and the aqueous phase was extracted with dichloromethane. The organic layers were combined, dried over sodium sulfate and evaporated to yield the title compound as colorless solid. The crude product was dissolved in dichloromethane and adsorbed on TEFLON BULK SORBENTS. Purification over a silica gel cartridge (Rf200), eluting with cyclohexane/ethyl acetate Gradient gave a mixture of the title compounds as a yellow solid. $^1$H NMR (400 MHz, CDCl$_3$) δ ppm 1.35-1.44 (m, 6H), 3.00 (q, 2H), 4.22-4.30 (m, 5H), 7.35 (s, 1H), 7.73 (d, 2H), 7.85 (s, 2H), 8.14 (d, 2H).

Step C: 5-ethyl-2-[3-ethylsulfonyl-6-[4-(trifluoromethyl)phenyl]-2-pyridyl]-3-methyl-6-(trifluoromethyl)imidazo[4,5-c]pyridin-4-one (compound 14.007, example P2, table P)

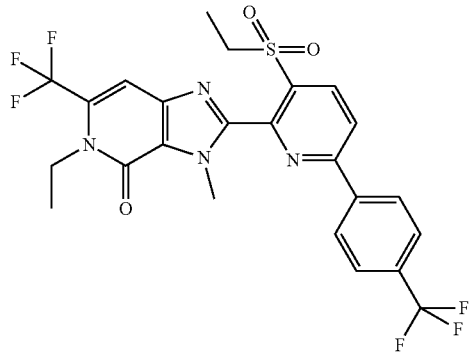

(Compound 14.007, example P2, table P)

A solution of 5-ethyl-2-[3-ethylsulfanyl-6-[4-(trifluoromethyl)phenyl]-2-pyridyl]-3-methyl-6-(trifluoromethyl) imidazo[4,5-c]pyridin-4-one (compound 13.007, example P1, table P) (0.115 g, 0.2184 mmol) in dichloromethane (4.4 ml) was stirred in an ice bath and meta-chloroperbenzoic acid (0.1292 g, 0.5242 mmol, 70% purity) was added in portions, in such a way that the temperature of the reaction mixture was kept below 10° C. The bath was then removed and the mixture was stirred 2 further hours at 20° C. After completion of the reaction, the mixture was stirred with saturated aqueous sodium bicarbonate solution. The phases were separated and the aqueous phase was extracted with dichloromethane. The organic layers were combined, washed 3× with 5 ml 10% $NaHSO_3$ solution in water then with a solution of NaOH 1N to remove meta-Chloroperoxybenzoic acid, dried over sodium sulfate and evaporated to yield the title compound as colorless solid. $^1$H NMR (400 MHz, $CDCl_3$) δ ppm 1.39 (m, 6H), 3.81 (q, 2H), 4.14 (s, 3H), 4.26 (q, 2H), 7.23 (s, 1H), 7.79 (d, 2H), 8.12 (d, 1H), 8.22 (d, 2H), 8.58 (d, 1H).

Example E2: Preparation of 5-ethyl-2-[3-ethylsulfonyl-6-[3-(trifluoromethyl)pyrazol-1-yl]-2-pyridyl]-3-methyl-6-(trifluoromethyl)imidazo[4,5-c]pyridin-4-one (compound 14.017, example P3, table P)

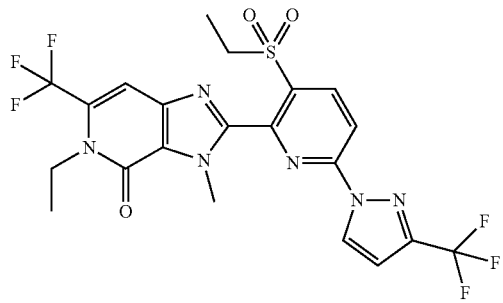 [SMILES: CCn1c(C(F)(F)F)cc2nc(-c3nc(-n4ccc(C(F)(F)F)n4)ccc3S(=O)(=O)CC)n(C)c2c1=O]

Step A: N-[1-ethyl-3-(methylamino)-2-oxo-6-(trifluoromethyl)-4-pyridyl]-3-ethylsulfonyl-6-[3-(trifluoromethyl)pyrazol-1-yl]pyridine-2-carboxamide and N-[4-amino-1-ethyl-2-oxo-6-(trifluoromethyl)-3-pyridyl]-3-ethylsulfonyl-N-methyl-6-[3-(trifluoromethyl)pyrazol-1-yl]pyridine-2-carboxamide

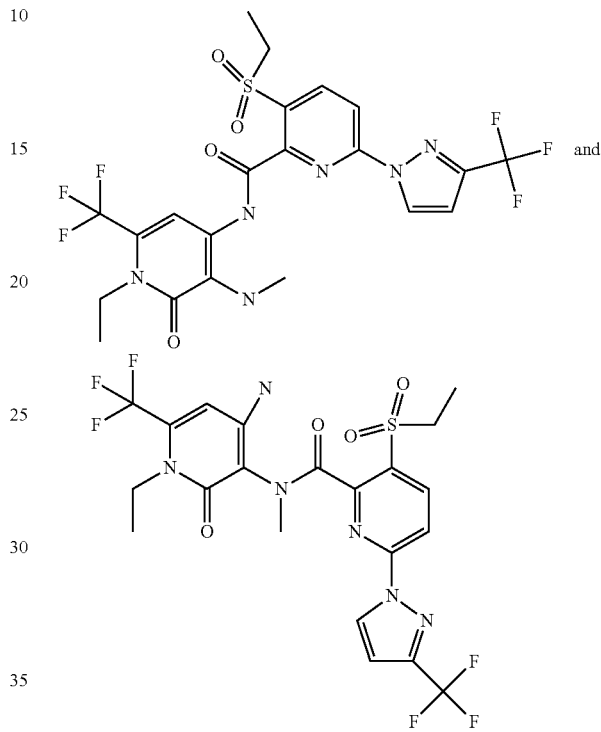

To a suspension of 3-ethylsulfonyl-6-[3-(trifluoromethyl)pyrazol-1-yl]pyridine-2-carboxylic acid (Intermediate 4, 297.0 mg, 0.8503 mmol) in dichloromethane (1.7 ml) was added one drop of N,N-dimethylformamide, followed by oxalyl chloride (220.3 mg, 0.1514 mL, 1.701 mmol). After the end of gas evolution, the reaction mixture was stirred 30 minutes at reflux. The solvent was evaporated under reduced pressure at a bath temperature of 60° C. The residue was redissolved 0.5 ml of THF.

To a solution of 4-amino-1-ethyl-3-(methylamino)-6-(trifluoromethyl)pyridin-2-one (prepared in Intermediate 2: step C, 100 mg, 0.425 mmol) in THF (1.7 ml) was added pyridine (201.78 mg, 0.21 mL, 2.55 mmol). The solution was cooled at 0° C. and the previous acyl chloride solution was slowly added. Then the resulting solution was cooled with an ice bath, before slow addition of the previous acyl chloride solution. The resulting mixture was stirred 3 hour at reflux. The solution was neutralized by addition of a saturated aqueous solution of sodium hydrogenocarbonate and the product was extracted twice with ethyl acetate. The organic solution was dried over sodium sulfate and evaporated under reduced pressure to yield the crude product. The crude product was dissolved in dichloromethane and adsorbed on TEFLON BULK SORBENTS. Purification over a silica gel cartridge (Rf200), eluting with cyclohexane/ethyl acetate Gradient gave a mixture of the title compounds as a solid._LC-MS (Method A): RT 1.09, 567 (M+H$^+$), 565 (M−H$^+$).

Step B: 5-ethyl-2-[3-ethylsulfonyl-6-[3-(trifluoromethyl)pyrazol-1-yl]-2-pyridyl]-3-methyl-6-(trifluoromethyl)imidazo[4,5-c]pyridin-4-one (Compound 14.017, Example P3, Table p)

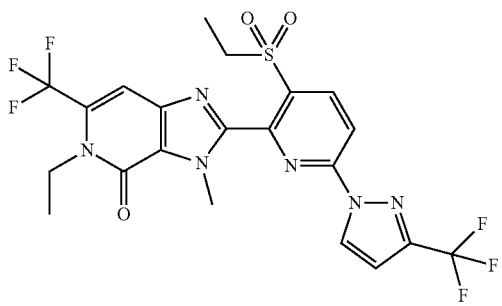 [SMILES: CCn1c(C(F)(F)F)cc2nc(-c3nc(-n4ccc(C(F)(F)F)n4)ccc3S(=O)(=O)CC)n(C)c2c1=O]

A mixture of N-[1-ethyl-3-(methylamino)-2-oxo-6-(trifluoromethyl)-4-pyridyl]-3-ethylsulfonyl-6-[3-(trifluoromethyl)pyrazol-1-yl]pyridine-2-carboxamide and N-[4-amino-1-ethyl-2-oxo-6-(trifluoromethyl)-3-pyridyl]-3-ethylsulfonyl-N-methyl-6-[3-(trifluoromethyl)pyrazol-1-yl]pyridine-2-carboxamide (0.455 g, 0.8032 mmol, the product of step A) in 4.02 ml of acetic acid was heated at 150° C. for 90 minutes under MW. The dark brown solution was poured into a mixture of ethyl acetate and water. The phases were separated and the aqueous phase was extracted with dichloromethane. The organic layers were combined, dried over sodium sulfate and evaporated to yield the title compound as colorless solid. The crude product was dissolved in dichloromethane and adsorbed on TEFLON BULK SORBENTS. Purification over a silica gel cartridge (Rf200), eluting with cyclohexane/ethyl acetate Gradient gave a mixture of the title compounds as a solid. $^1$H NMR (400 MHz, CDCl$_3$) δ ppm 1.35-1.44 (m, 6H), 3.74 (q, 2H), 4.02 (s, CH3), 4.26 (q, 2H), 6.78 (d, 1H), 7.23 (s, 1H), 8.39 (d, 1H), 8.57 (d, 1H), 8.64 (d, 1H).

Example E3: Preparation of Compounds P10 to P38

1. Boronic acids (2 eq.) are weighed manually into a conical microwave vial. 0.2 mL DME is added with a multipipette.
2. A stock solution of 2-(6-chloro-3-ethylsulfonyl-2-pyridyl)-5-ethyl-3-methyl-6-(trifluoromethyl)imidazo[4,5-c]pyridin-4-one (preparation described before) was prepared by mixing 458 mg in 10.2 mL DME.
3. A stock suspension of Pd(PPh$_3$)$_2$Cl$_2$ (0.17 eq.) is done by mixing 143 mg in 8 mL. 0.3 mL of solution 2. was added into vials. followed by 0.3 mL water, 40 uL of a solution of sodium carbonate (2 M) and 0.2 mL of solution 3. The vials were flushed with argon and capped. Then, the vials were heat in a microwave oven at 110° C. for 10 min. The solvents were evaporated and a mixture of water and ethyl acetate were added to the vial. The aqueous phase was extracted 3× with ethyl acetate. The combined organic layers were dried on magnesium sulfate and concentrated under vacuum. The residue was purified by reverse phase preparative system.

Spectra were recorded on a Mass Spectrometer (AC-QUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75

| P number | RT | M (calculated) | (M + H)$^+$ (measured) |
|---|---|---|---|
| P10 | 2.11 | 558.05 | 559.09 |
| P11 | 1.7 | 454.13 | 455.33 |
| P12 | 1.93 | 526.11 | 527.35 |
| P13 | 1.37 | 491.12 | 492.4 |
| P14 | 1.87 | 508.12 | 509.39 |
| P15 | 1.74 | 515.12 | 516.13 |
| P16 | 1.82 | 559.11 | 560.34 |
| P17 | 1.99 | 524.09 | 525.1 |
| P18 | 1.85 | 490.13 | 491.32 |
| P19 | 2.04 | 542.08 | 543.11 |
| P20 | 1.55 | 522.13 | 523.34 |
| P21 | 1.41 | 492.12 | 493.22 |
| P22 | 2.04 | 574.11 | 575.35 |
| P23 | 1.85 | 538.13 | 539.35 |
| P24 | 2.1 | 538.11 | 539.13 |
| P25 | 1.72 | 454.13 | 455.33 |
| P26 | 1.87 | 508.12 | 509.33 |
| P27 | 1.79 | 496.09 | 497.28 |
| P28 | 1.06 | 494.13 | 495.42 |
| P29 | 1.96 | 536.12 | 537.36 |
| P30 | 1.43 | 491.12 | 492.37 |
| P31 | 1.53 | 497.08 | 498.23 |
| P32 | 2.03 | 558.05 | 559.07 |
| P33 | 2.03 | 576.11 | 577.41 |
| P34 | 1.91 | 526.11 | 527.26 |
| P35 | 1.97 | 544.10 | 545.38 |
| P36 | 2.14 | 626.10 | 627.4 |
| P37 | 1.88 | 526.11 | 527.4 |
| P38 | 1.45 | 481.10 | 482.24 |

Example E4: Preparation of 2-[6-(cyclopropylamino)-3-ethylsulfonyl-2-pyridyl]-5-ethyl-3-methyl-6-(trifluoromethyl)imidazo[4,5-c]pyridin-4-one P40

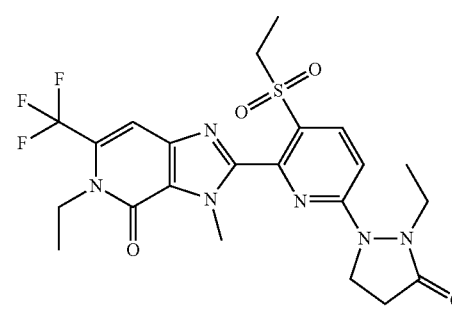

In a reaction vessel, 2-(6-chloro-3-ethylsulfonyl-2-pyridyl)-5-ethyl-3-methyl-6-(trifluoromethyl)imidazo[4,5-c]pyridin-4-one (100 mg, 0.2228 mmol) was dissolved in anhydrous N,N-dimethylacetamide (1.5 ml) and to it dipotassium carbonate (3.342 mmol, 0.4619 g) and 2-ethylpyrazolidin-1-ium-3-one chloride (0.3342 mmol, 0.05034 g) was added under mixture was heated in preheated oil bath at 110° C. for 3 hours. Reaction mixture was quenched in 10 ml of water and extracted in 20 ml of ethyl acetate three times, combined organic layer was evaporated and crude was purified by column chromatography to give 5-ethyl-2-[6-(2-ethyl-3-oxo-pyrazolidin-1-yl)-3-ethylsulfonyl-2-pyridyl]-3-methyl-6-(trifluoromethyl)imidazo[4,5-c]pyridin-4-one (30 mg, 25%). Mp=202-204° C. H NMR (400 MHz, CDCl$_3$) δ ppm 8.31 (d, 1H), 7.21 (s, 1H), 6.98 (d, 1H), 4.34 (t, 2H), 4.25 (d, 2H), 4.09 (s, 3H), 3.72 (d, 2H), 3.63 (q, 2H), 2.60 (t, 2H), 1.40 (t, 3H), 1.33 (t, 3H), 1.24 (t, 3H).

Example E5: Preparation of 5-cyclopropyl-2-[3-ethylsulfonyl-6-(1,2,4-triazol-1-yl)-2-pyridyl]-3-methyl-6-(trifluoromethyl)imidazo[4,5-c]pyridin-4-one P4

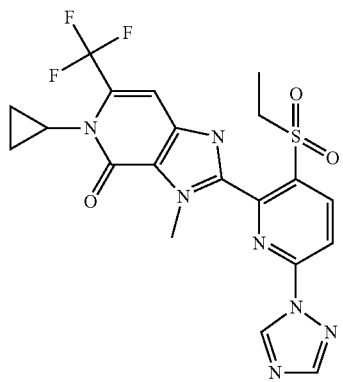

A 50 mL flask, flushed with argon, was added 4H-1,2,4-triazole (0.55 g, 7.8 mmol) and NMP (10 mL). Then, sodium hydride (60 mass %) in paraffin oil (0.2603 g, 6.509 mmol, 3.000) was added and after 30 min, a solution of 2-(6-chloro-3-ethylsulfonyl-2-pyridyl)-5-cyclopropyl-3-methyl-6-(trifluoromethyl) imidazo [4,5-c]pyridin-4-one (Intermediate 9, 1 g, 2.17 mmol) beforehand dissolved in NMP (10 mL) was added. The reaction mixture was stirred for 10 minutes at room temperature. The mixture was poured gently in cold water (200 mL) and the white solid formed was filtered. The crude was purified by column chromatography to give 5-cyclopropyl-2-[3-ethylsulfonyl-6-(1,2,4-triazol-1-yl)-2-pyridyl]-3-methyl-6-(trifluoromethyl)imidazo [4,5-c]pyridin-4-one P4 (831 mg, 77.6%). $^1$H NMR (400 MHz, CDCl$_3$) δ ppm 9.14 (s, 1H), 8.68 (d, 1H), 8.28 (d, 1H), 8.20 (s, 1H), 7.20 (s, 1H), 4.07 (s, 3H), 3.74 (q, 2H), 3.12 (m, 1H), 1.38 (t, 3H), 1.30 (m, 2H), 1.08 (m, 2H).

Example E6: Preparation of 2-[6-(4-chloropyrazol-1-yl)-3-ethylsulfanyl-2-pyridyl]-3,5-dimethyl-6-(trifluoromethyl)imidazo[4,5-c]pyridin-4-one P6

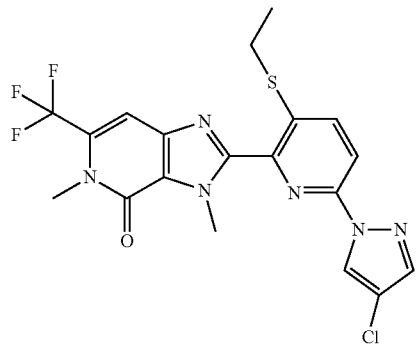 [SMILES: CCSc1ccc(-n2cc(Cl)cn2)nc1-c1nc2cc(C(F)(F)F)n(C)c(=O)c2n1C]

A mixture of 2-(6-chloro-3-ethylsulfanyl-2-pyridyl)-3,5-dimethyl-6-(trifluoromethyl)imidazo[4,5-c]pyridin-4-one (See Intermediate 8: 0.1 g, 0.2483 mmol) and dipotassium carbonate (0.069 g, 0.497 mmol) were dissolved in dimethylformamide (2 mL) and the suspension was stirred 1 h at 50° C. The reaction mixture was quenched with water and the aqueous layer was extracted 3 times with ethyl acetate. The combined organic layer was washed with water and brine, dried over sodium sulfate, filtered and evaporated under vacuum. Purification over a silica gel cartridge (Rf200), eluting with cyclohexane/ethyl acetate Gradient gave the title compound as a solid (in addition with starting material). The mixture was used without purification for the next step. LC-MS (Method A): RT 1.22, 469 (M+H$^+$).

Example E7: Preparation of 2-[6-(4-chloropyrazol-1-yl)-3-ethylsulfonyl-2-pyridyl]-3,5-dimethyl-6-(trifluoromethyl)imidazo[4,5-c]pyridin-4-one P7

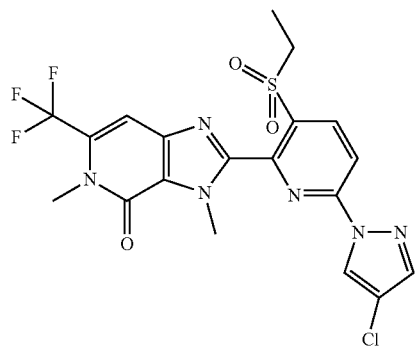 [SMILES: CCS(=O)(=O)c1ccc(-n2cc(Cl)cn2)nc1-c1nc2cc(C(F)(F)F)n(C)c(=O)c2n1C]

The sulfur of 2-[6-(4-chloropyrazol-1-yl)-3-ethylsulfanyl-2-pyridyl]-3,5-dimethyl-6-(trifluoromethyl)imidazo[4,5-c]pyridin-4-one P6 was oxidaze using the same protocol as described in Step C (Example E1). 2-[6-(4-chloropyrazol-1-yl)-3-ethylsulfonyl-2-pyridyl]-3,5-dimethyl-6-(trifluoromethyl)imidazo[4,5-c]pyridin-4-one P7. $^1$H NMR (400 MHz, CDCl$_3$) δ ppm 1.35 (t, 3H), 3.68-3.75 (m, 5H), 4.10 (s, 3H), 7.23 (s, 1H), 7.76 (s, 1H), 8.28 (d, 1H), 8.49 (d, 1H), 8.58 (d, 1H).

TABLE P

| Compounds of formula (I): | | | |
|---|---|---|---|
| Compound No. | Compound | Melting Point | MS/NMR/LC-MS |
| P1 | [structure] | — | See preparatory examples |
| P2 | [structure] | 201-202 | See preparatory examples |
| P3 | [structure] | — | See preparatory examples |
| P4 | [structure] | | See preparatory examples |

TABLE P-continued

Compounds of formula (I):

| Compound No. | Compound | Melting Point | MS/NMR/LC-MS |
|---|---|---|---|
| P5 | | | P5 was prpared using the intermediate 10 and protocols described in Example E2. LC-MS(Method A): RT 0.95, 482(M + H$^+$). |
| P6 | | | See preparatory examples |
| P7 | | | See preparatory examples |
| P8 | | | Prepared as described for E6: LC-MS(Method A): RT 1.22, 503(M + H$^+$). |

TABLE P-continued

Compounds of formula (I):

| Compound No. | Compound | Melting Point | MS/NMR/LC-MS |
|---|---|---|---|
| P9 | | | Prepared as described for E7: LC-MS(Method A): RT 1.15, 535(M + H⁺). |
| P10 | | | See preparatory examples |
| P11 | | | See preparatory examples |
| P12 | | | See preparatory examples |

TABLE P-continued

Compounds of formula (I):

| Compound No. | Compound | Melting Point | MS/NMR/LC-MS |
|---|---|---|---|
| P13 | | | See preparatory examples |
| P14 | | | See preparatory examples |
| P15 | | | See preparatory examples |
| P16 | | | See preparatory examples |

TABLE P-continued

Compounds of formula (I):

| Compound No. | Compound | Melting Point | MS/NMR/LC-MS |
|---|---|---|---|
| P17 | | | See preparatory examples |
| P18 | | | See preparatory examples |
| P19 | | | See preparatory examples |
| P20 | | | See preparatory examples |
| P21 | | | See preparatory examples |

TABLE P-continued

Compounds of formula (I):

| Compound No. | Compound | Melting Point | MS/NMR/LC-MS |
|---|---|---|---|
| P22 | | | See preparatory examples |
| P23 | | | See preparatory examples |
| P24 | | | See preparatory examples |
| P25 | | | See preparatory examples |

TABLE P-continued

Compounds of formula (I):

| Compound No. | Compound | Melting Point | MS/NMR/LC-MS |
|---|---|---|---|
| P26 | | | See preparatory examples |
| P27 | | | See preparatory examples |
| P28 | | | See preparatory examples |
| P29 | | | See preparatory examples |
| P30 | | | See preparatory examples |

TABLE P-continued

Compounds of formula (I):

| Compound No. | Compound | Melting Point | MS/NMR/LC-MS |
|---|---|---|---|
| P31 | | | See preparatory examples |
| P32 | | | See preparatory examples |
| P33 | | | See preparatory examples |
| P34 | | | See preparatory examples |

TABLE P-continued

Compounds of formula (I):

| Compound No. | Compound | Melting Point | MS/NMR/LC-MS |
|---|---|---|---|
| P35 | | | See preparatory examples |
| P36 | | | See preparatory examples |
| P37 | | | See preparatory examples |
| P38 | | | See preparatory examples |

TABLE P-continued

Compounds of formula (I):

| Compound No. | Compound | Melting Point | MS/NMR/LC-MS |
|---|---|---|---|
| P39 | | | Prepared via "Pd" coupling via intermediate 8. $^1$H NMR (400 MHz, CDCl$_3$) δ = 8.29 (d, 1H), 7.48 (d, 1H), 7.20 (s, 1H), 4.02 (s, 3H), 3.72 (s, 3H), 3.68 (q, 2H), 2.20 (m, 1H), 1.32 (t, 3H), 1.12 (m, 4H). |
| P40 | | | See preparatory examples |
| P41 | | | Prepared via "Pd" coupling with the (3,5-difluorophenyl)boronic acid and the intermediate 9 as described in Step B for the coupling of the intermediate 3.: LC-MS(Method A): RT 1.17, 539 (M + H$^+$). |
| P42 | | | Prepared via "Pd" coupling with the (3-fluorophenyl)boronic acid and the intermediate 9 as described in Step B for the coupling of the intermediate 3. $^1$H NMR (400 MHz, CDCl$_3$) δ = 8.54 (d, 1H), 8.08 (d, 1H), 7.88 (d, 1H), 7.82 (d, 1H), 7.52 (m, 1H), 7.23(m, 2H), 4.10 (s, 3H), 3.78 (q, 2H), 3.12(m, 1H), 1.38 (t, 3H), 1.30 (m, 2H), 1.08 (m, 2H). |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 96 and P of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis (dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, Anagrapha falcifera NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium xlecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B$_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, diclifos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox(1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, E1 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, fluenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex(1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, 0-5-dichloro-4-iodophenyl O-ethyl ethylphosphonothioate (IUPAC name) (1057)+TX, O,O-diethyl 0-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex(1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox

[88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ®+TX, TAZO B®)+TX, Azotobacter+TX, Azotobacter chroocuccum (Azotomeal®)+TX, Azotobacter cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®, BioNem-WP®, VOTVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus sphaericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1 Ab+TX, *Bacillus thuringiensis aizawai* GC 91 (Agree®)+

TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of Clavipacter *michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis* tenebrionis (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, Cellulomonas flavigena+TX, *Chaetomium* cochliodes (Nova-Cide®)+TX, *Chaetomium globosum* (Nova-Cide®)+TX, Chromobacterium subtsugae strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, Clonostachys *rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus* infirmo-miniatus+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex+TX, Madex Plus®+TX, Madex Max/Carpovirusine®)+TX, Cylindrobasidium laeve (Stumpout®)+TX, Cylindrocladium+TX, Debaryomyces *hansenii*+TX, *Drechslera hawaiinensis*+TX, *Enterobacter cloacae*+TX, Enterobacteriaceae+TX, Entomophtora virulenta (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, Galactomyces *geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, Muscodorroseus strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia* onychis+TX, *Pichia stipites*+TX, *Pseudomonas aeruginosa*+TX, *Pseudomonas* aureofasciens (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia* minor (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma* atroviride (Plantmate®)+TX, *Trichoderma hamatum* TH 382+TX, *Trichoderma harzianum* rifai (Mycostar®)+TX, *Trichoderma harzianum* T-22 (Trianum-P®+

TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, Trichothecium spp.+TX, Trichothecium *roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®)+TX; and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, Tetradecatrienyl acetate+TX, 13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, CheckMate®+TX, Lavandulyl senecioate; and Macrobials including: *Aphelinus abdominalis*+TX, *Aphidius ervi* (Aphelinus-System®)+TX, Acerophagus *papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, *Andersoni*-System®)+TX, *Amblyseius californicus* (Amblyline®+TX, Spical®)+TX, *Amblyseius cucumeris* (Thripex+TX, Bugline *cucumeris*®)+TX, *Amblyseius fallacis* (*Fallacis*®)+TX, *Amblyseius swirskii* (Bugline *swirskii*®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla camea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®)+TX, Macroline c®®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, SciaRid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, Tetrastichus setifer+TX, *Thripobius semiluteus*+TX, *Torymus sinensis*+TX, *Trichogramma brassicae* (Tricholine b®)+TX, *Trichogramma brassicae* (TrichoStrip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; under the internet address "http://www.alanwood.net/pesticides/".

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 96 and P with active ingredients described above comprises a compound selected from Tables 1 to 96 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 96 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 96 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention. The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm:
P3, P4, P5, P11, P14, P16, P21, P28, P29 and P37.

Example B2: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
P2, P3, P4, P5, P9, P10, P11, P12, P13, P14, P15, P16, P17, P18, P19, P20, P21, P22, P23, P24, P25, P28, P29, P30, P31, P32, P33, P34, P35, P36, P37, P38, P39, P40 and P41.

Example B3: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P2, P3, P4, P5, P9, P12, P14, P15, P16, P17, P18, P20, P21, P22, P23, P29, P30, P35, P37 and P39.

Example B4: *Frankliniella occidentalis* (Western Flower *Thrips*): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:
P13, P16 and P20.

Example B5: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:

P4, P5, P11, P12, P14, P16, P17, P18, P20, P21, P23, P25, P29, P30, P31, P38 and P39.

Example B6: *Myzus persicae* (Green Peach Aphid): Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm:

P4, P5, P38 and P40.

Example B7: *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

P2, P3, P4, P5, P9, P10, P11, P12, P13, P14, P15, P16, P17, P18, P19, P20, P21, P22, P23, P24, P26, P28, P29, P30, P31, P32, P33, P34, P35, P36, P37, P38, P39, P40 and P41.

Example B8: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:

P2, P3, P4, P5, P7, P9, P10, P11, P12, P13, P14, P15, P16, P17, P18, P19, P20, P21, P22, P23, P24, P25, P26, P27, P28, P29, P30, P31, P32, P33, P34, P35, P36, P37, P38, P39 and P41.

Example B9: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:

P4, P5, P11, P12, P14, P15, P18, P20, P21, P22, P37, P39 and P41.

Example B10: *Tetranychus urticae* (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compound resulted in at least 80% mortality at an application rate of 200 ppm:

P4.

Example B11: *Thrips tabaci* (Onion *Thrips*) Feeding/Contact Activity

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:

P4 and P5.

Example B12: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:

P2, P3 and P39.

Example B13: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles* st. after 48 h and/or 24 h: P2 and P3.

The invention claimed is:
1. A compound of formula I,

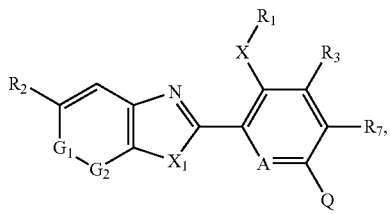

wherein
A is CH, N or the N-oxide;
$G_1$ is $NR_4$ and $G_2$ is $C(Y)$;
Y is O or S;
X is S, SO or $SO_2$;
$X_1$ is $NR_6$, wherein $R_6$ is hydrogen, $C_2$-$C_6$alkenyl, $C_2$-$C_6$alkynyl, $C_1$-$C_4$alkoxy-$C_1$-$C_4$alkyl, $C_3$-$C_6$cycloalkyl or $C_1$-$C_6$alkyl which can be mono- or polysubstituted by substituents selected from the group consisting of halogen and $C_1$-$C_4$alkylsulfinyl;
Q is a five- to six-membered monocyclic ring system linked via a carbon atom to the ring which contains the group A, said ring system is aromatic, partially saturated or fully saturated and can contain 1 to 4 hetero atoms selected from the group consisting of nitrogen, oxygen and sulfur; with the proviso that each ring system cannot contain more than 2 oxygen atoms and more than 2 sulfur atoms; said five- to six-membered ring system can be mono- to polysubstituted by substituents independently selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; or
Q is a five- to six-membered, aromatic, partially saturated or fully saturated ring system containing 1, 2 or 3 nitrogen atoms, said ring system is linked via a nitrogen atom to the ring which contains the group A, said ring system can be mono- or polysubstituted by substituents selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$di-alkylamino, formyl, $C_2$-$C_6$alkenyl, $C_2$-$C_6$alkynyl and $C_1$-$C_6$haloalkylcarbonyl; and said ring system can additionally contain 1 or 2 heteroatoms selected from the group consisting of nitrogen, oxygen and sulfur, with the proviso that said ring system cannot contain more than one oxygen atom and more than one sulfur atom; or
Q is $C_3$-$C_4$cycloalkyl, or $C_3$-$C_4$cycloalkyl mono- or poly substituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and $C_1$-$C_4$haloalkylcarbonyl; or
Q is $C_2$-$C_6$alkenyl, or $C_2$-$C_6$alkenyl mono- or polysubstituted by substituents selected from the group consisting of halogen, cyano, $C_1$-$C_4$alkyl, cyclopropyl, $C_1$-$C_4$haloalkyl, $C_1$-$C_4$haloalkoxy, $C_1$-$C_4$alkoxy or phenyl wherein said phenyl can be mono- or polysubstituted by substituents selected from the group consisting of halogen, cyano, $C_1$-$C_4$alkyl, $C_1$-$C_4$haloalkyl; or
Q is $C_2$-$C_6$alkynyl, or $C_2$-$C_6$alkynyl mono- or polysubstituted by substituents selected from the group consisting of halogen, cyano, $C_1$-$C_4$alkyl, cyclopropyl, $C_1$-$C_4$haloalkyl, $C_1$-$C_4$haloalkoxy, $C_1$-$C_4$alkoxy or phenyl wherein said phenyl can be mono- or polysubstituted by substituents selected from the group consisting of halogen, cyano, $C_1$-$C_4$alkyl, $C_1$-$C_4$haloalkyl; or
Q is $C_1$-$C_4$alkyl mono- or polysubstituted by substituents selected from the group consisting of $C_3$-$C_6$cycloalkyl, phenyl, pyridine and pyrimidine, wherein said $C_3$-$C_6$cycloalkyl, phenyl, pyridine and pyrimidine can be mono- or polysubstituted by substituents selected from the group consisting of halogen, cyano, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy;
$R_1$ is $C_1$-$C_6$alkyl, $C_1$-$C_6$haloalkyl, $C_3$-$C_6$cycloalkyl or $C_3$-$C_6$cycloalkyl-$C_1$-$C_4$alkyl; or
$R_1$ is $C_3$-$C_6$cycloalkyl-$C_1$-$C_4$alkyl mono- or polysubstituted by substituents selected from the group consisting of halogen, cyano, $C_1$-$C_4$ haloalkyl and $C_1$-$C_4$alkyl; or
$R_1$ is $C_2$-$C_6$alkenyl, $C_2$-$C_6$haloalkenyl, $C_2$-$C_6$alkynyl or $C_2$-$C_6$haloalkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_6$haloalkylsulfanyl, $C_1$-$C_6$haloalkylsulfinyl, $C_1$-$C_6$haloalkylsulfonyl, $C_1$-$C_6$haloalkoxy, or $C_1$-$C_6$haloalkylcarbonyl; or
$R_2$ is $C_3$-$C_6$cycloalkyl which can be mono- or polysubstituted by substituents selected from the group consisting of halogen, cyano, $C_1$-$C_4$haloalkyl and $C_1$-$C_4$alkyl;
$R_3$ is hydrogen or $C_1$-$C_2$alkyl;
$R_4$ is $C_1$-$C_6$alkyl, $C_1$-$C_6$haloalkyl, or are $C_3$-$C_6$cycloalkyl which can be mono- or polysubstituted by substituents selected from the group consisting of halogen, cyano, $C_1$-$C_4$haloalkyl and $C_1$-$C_4$alkyl; or
$R_4$ is, independently from each other, $C_3$-$C_6$cycloalkyl-$C_1$-$C_4$alkyl which can be mono- or polysubstituted by cyano, $C_1$-$C_4$alkyl, halogen or $C_1$-$C_2$haloalkyl; or
$R_4$ is, independently from each other, $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amino or hydroxyl; or
$R_4$ is $C_1$-$C_4$alkyl substituted by $R_8$; or $R_4$ is $C_2$-$C_6$alkenyl substituted by $R_8$; or $R_4$ is $C_2$-$C_6$alkynyl substituted by $R_8$;

$R_7$ is hydrogen, halogen, $C_1$-$C_6$haloalkyl, $C_1$-$C_6$haloalkylsulfanyl, $C_1$-$C_6$haloalkylsulfonyl, $C_1$-$C_6$haloalkylsulfinyl, $C_3$-$C_6$cycloalkyl or $C_3$-$C_6$cycloalkyl mono or polysubstituted by halogen, cyano, $C_1$-$C_4$alkyl or $C_1$-$C_4$haloalkyl; and $R_8$ is cyano, $C_1$-$C_4$alkylsulfanyl, $C_1$-$C_4$alkylsulfonyl, $C_1$-$C_4$alkylsulfinyl, $C_1$-$C_4$haloalkylsulfanyl, $C_1$-$C_4$haloalkylsulfonyl, $C_1$-$C_6$haloalkylsulfinyl, $C_1$-$C_4$alkoxy, $C_1$-$C_4$alkoxy$C_1$-$C_4$alkoxy, $C_3$-$C_6$cycloalkyl or phenyl; said phenyl and said $C_3$-$C_6$cycloalkyl can be mono- or polysubstituted by substituents selected from the group consisting of halogen, $C_1$-$C_4$alkyl, cyano, $C_1$-$C_4$haloalkyl and $C_1$-$C_4$alkoxy; and agrochemically acceptable salts, stereoisomers, enantiomers, tautomers or N-oxide of the compounds of formula I.

2. The compound of formula I according to claim 1, wherein

Q is selected from the group consisting of J-0 to J-31:

J-0
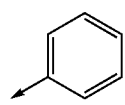

J-1
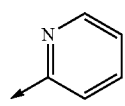

J-2
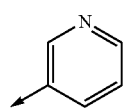

J-3
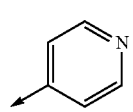

J-4
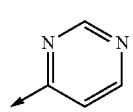

J-5
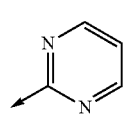

J-6
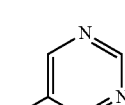

J-7
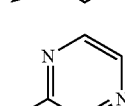

J-8
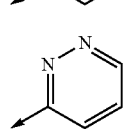

-continued

J-9
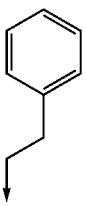

J-10
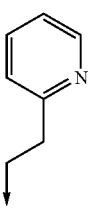

J-11
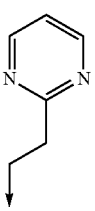

J-12
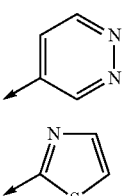

J-13
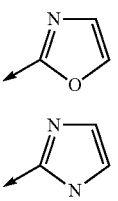

J-14
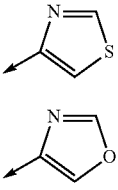

J-15
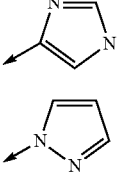

J-16
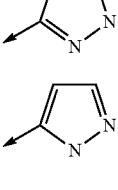

J-17
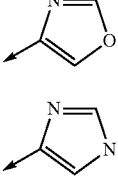

J-18
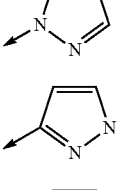

J-19
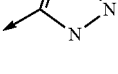

J-20
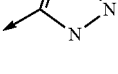

J-21
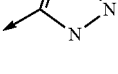

-continued

J-22 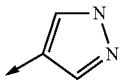

J-23 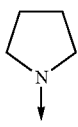

J-24 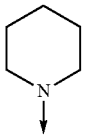

J-25 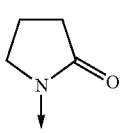

J-26 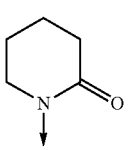

J-27 

J-28 

J-29

J-30 

J-31 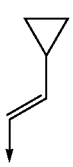

wherein each group J-0 to J-8 and J-12 to J-26 can be mono- di- or trisubstituted with Rx, wherein each Rx, independently from each other, is selected from the group consisting of halogen, cyano, $C_1$-$C_6$alkyl, nitro, hydroxyl, $C_1$-$C_6$haloalkyl, $C_1$-$C_6$haloalkoxy, $C_1$-$C_6$alkoxy, $C_1$-$C_6$alkylsulfanyl, $C_1$-$C_6$alkylsulfinyl, $C_1$-$C_6$alkylsulfonyl, $C_1$-$C_6$alkylcarbonyl, $C_1$-$C_6$alkoxycarbonyl, $C_1$-$C_6$haloalkylsulfanyl, $C_1$-$C_6$haloalkylsulfinyl, $C_1$-$C_6$haloalkylsulfonyl, $C_1$-$C_6$alkylamino, $C_3$-$C_6$cycloalkylamino, $C_1$-$C_6$dialkylamino, formyl, $C_2$-$C_6$alkenyl, $C_2$-$C_6$alkynyl and $C_1$-$C_6$haloalkylcarbonyl; wherein the group J-27 can be mono- di- or trisubstituted with Rx, wherein each Rx, independently from each other, is halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and $C_1$-$C_4$haloalkylcarbonyl; wherein the aromatic part of the group J-9 to J11 can be mono- di- or trisubstituted with Rx, wherein each Rx, independently from each other, is selected from the group consisting of halogen, cyano, $C_1$-$C_4$alkylsulfanyl, $C_1$-$C_4$alkylsulfinyl, $C_1$-$C_4$alkyl sulfonyl, $C_1$-$C_4$haloalkylsulfanyl, $C_1$-$C_4$haloalkylsulfinyl, $C_1$-$C_4$haloalkylsulfonyl, $C_1$-$C_4$alkyl, $C_1$-$C_4$haloalkyl, $C_1$-$C_6$haloalkoxy and $C_1$-$C_4$alkoxy.

3. The compound of formula I according to claim 1 represented by the compounds of formula I-1

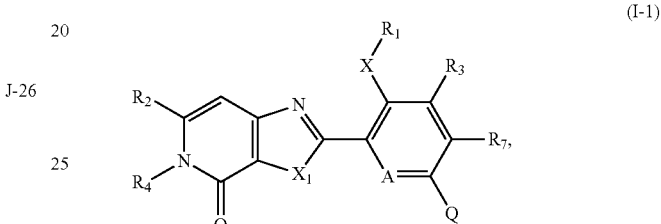

(I-1)

$R_1$ is methyl, ethyl, n-propyl, i-propyl or cyclopropylmethyl;
$R_3$ is hydrogen;
$R_7$ is hydrogen, halogen or $C_1$-$C_3$haloalkyl; and
$X_1$ is N-methyl.

4. The compound of formula I-1 according to claim 3, wherein
$R_2$ is $C_1$-$C_4$haloalkyl, halogen, $C_1$-$C_4$haloalkylsulfanyl, $C_1$-$C_4$haloalkylsulfinyl or $C_1$-$C_4$haloalkyl sulfonyl;
X is $SO_2$;
$R_1$ is ethyl;
$X_1$ is N-methyl;
$R_3$ is hydrogen; and
$R_7$ is hydrogen or $C_1$-$C_2$haloalkyl.

5. The compound of formula I according to claim 1 represented by the compounds of formula I-1

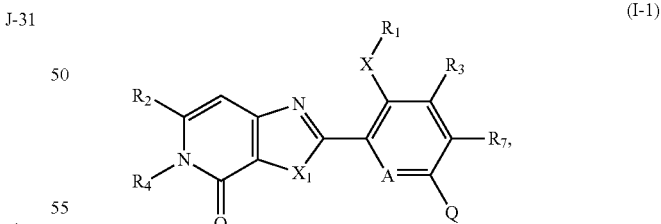

(I-1)

wherein $R_3$ and $R_7$ are hydrogen;
A is CH or N;
$R_4$ is $C_1$-$C_3$alkyl or cyclopropyl;
$R_2$ is $C_1$-$C_2$haloalkyl;
$X_1$ is N—$CH_3$;
X is S, SO or $SO_2$;
$R_1$ is $C_1$-$C_3$alkyl;
Q is selected from the group consisting of J-0, J-2, J-3, J6, J-19, J-27, K-13, K-14, K-15, K-30, K-31, K-32 and K-33:

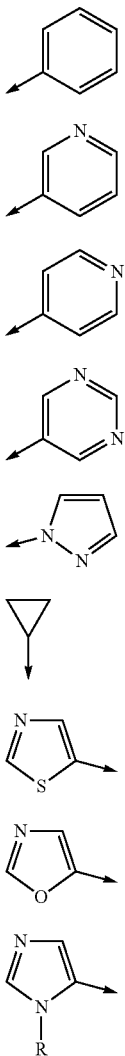
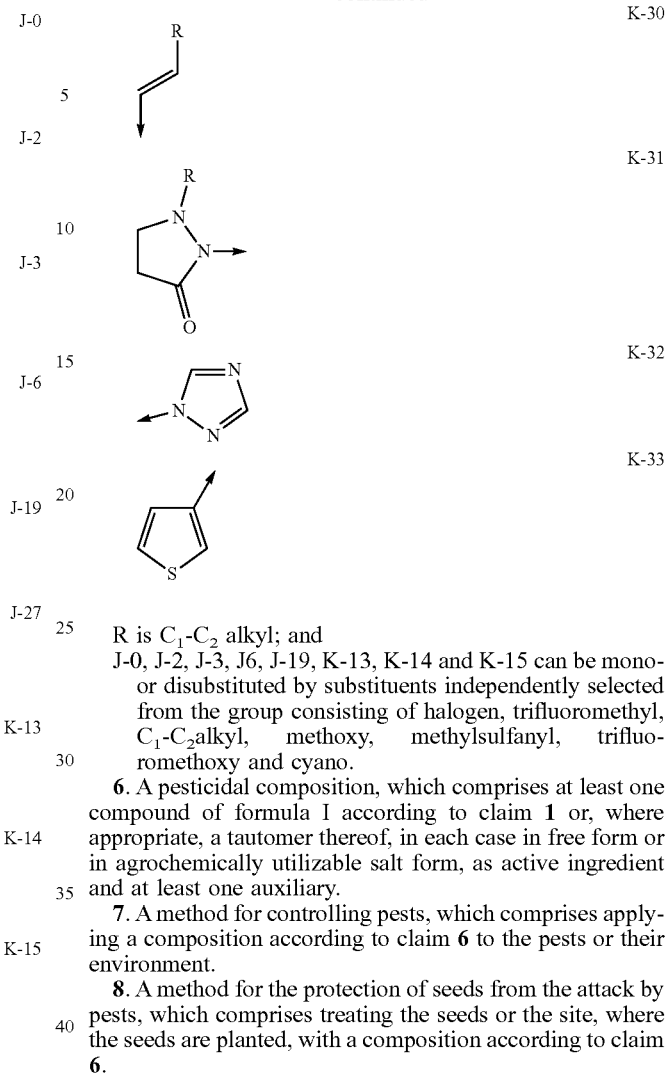

R is $C_1$-$C_2$ alkyl; and

J-0, J-2, J-3, J6, J-19, K-13, K-14 and K-15 can be mono- or disubstituted by substituents independently selected from the group consisting of halogen, trifluoromethyl, $C_1$-$C_2$alkyl, methoxy, methylsulfanyl, trifluoromethoxy and cyano.

6. A pesticidal composition, which comprises at least one compound of formula I according to claim 1 or, where appropriate, a tautomer thereof, in each case in free form or in agrochemically utilizable salt form, as active ingredient and at least one auxiliary.

7. A method for controlling pests, which comprises applying a composition according to claim 6 to the pests or their environment.

8. A method for the protection of seeds from the attack by pests, which comprises treating the seeds or the site, where the seeds are planted, with a composition according to claim 6.

* * * * *